(12) United States Patent
Grotz

(10) Patent No.: US 10,045,851 B2
(45) Date of Patent: Aug. 14, 2018

(54) RESILIENT INTERPOSITIONAL ARTHROPLASTY DEVICE

(71) Applicant: iOrthopedics, Inc., Las Vegas, NV (US)

(72) Inventor: Robert Thomas Grotz, Las Vegas, NV (US)

(73) Assignee: IORTHOPEDICS, INC., Las Vegas, NV (US)

( * ) Notice: Subject to any disclaimer, the term of this patent is extended or adjusted under 35 U.S.C. 154(b) by 0 days.

(21) Appl. No.: 15/651,958

(22) Filed: Jul. 17, 2017

(65) Prior Publication Data

US 2017/0312088 A1  Nov. 2, 2017

Related U.S. Application Data

(63) Continuation of application No. 14/239,992, filed as application No. PCT/US2012/053207 on Aug. 30, 2012, now Pat. No. 9,757,241.

(Continued)

(51) Int. Cl.
*A61F 2/38* (2006.01)
*A61L 27/54* (2006.01)
(Continued)

(52) U.S. Cl.
CPC ........ *A61F 2/3859* (2013.01); *A61F 2/30756* (2013.01); *A61L 27/18* (2013.01);
(Continued)

(58) Field of Classification Search
CPC ............... A61F 2/3872; A61F 2/389; A61F 2002/3895; A61F 2/3859;
(Continued)

(56) References Cited

U.S. PATENT DOCUMENTS 3,864,758 A  2/1975  Yakich
3,867,728 A  2/1975  Stubstad et al.
(Continued)

FOREIGN PATENT DOCUMENTS

DE  2501080 A1  7/1976
DE  10339605 A1  4/2005
(Continued)

OTHER PUBLICATIONS

Co-pending U.S. Appl. No. 14/846,651, filed Sep. 4, 2015.
(Continued)

*Primary Examiner* — Alvin Stewart
(74) *Attorney, Agent, or Firm* — Michel Graffeo

(57) ABSTRACT

This disclosure is directed to restoring joints by deploying a resilient interpositional arthroplasty implant. Such implants function to pad cartilage defects, cushion, and replace or restore the articular surface, which may preserve joint integrity, reduce pain and improve function. The implant may endure variable joint compressive and shear forces and cyclic loads. The implant may repair, reconstruct, and regenerate joint anatomy, and thereby improve upon joint replacement alternatives. The walls of this invention may capture, distribute and hold living cells until aggregation and hyaline cartilage regrowth occurs. The implant may be deployed into debrided joint spaces, molding and conforming to surrounding structures with sufficient stability so as to enable immediate limb use after outpatient surgery. Appendages of the implant may repair or reconstruct tendons or ligaments, and menisci by interpositional inflatable or compliant polymer arthroplasties that promote anatomic joint motion.

20 Claims, 14 Drawing Sheets

Related U.S. Application Data

(60) Provisional application No. 61/530,324, filed on Sep. 1, 2011.

(51) Int. Cl.
*A61L 27/58* (2006.01)
*A61L 27/34* (2006.01)
*A61L 27/38* (2006.01)
*A61L 27/56* (2006.01)
*A61L 27/18* (2006.01)
*A61F 2/30* (2006.01)
*A61B 17/064* (2006.01)

(52) U.S. Cl.
CPC ........... *A61L 27/34* (2013.01); *A61L 27/3817* (2013.01); *A61L 27/3834* (2013.01); *A61L 27/3852* (2013.01); *A61L 27/54* (2013.01); *A61L 27/56* (2013.01); *A61L 27/58* (2013.01); *A61B 17/0642* (2013.01); *A61F 2/3872* (2013.01); *A61F 2002/30062* (2013.01); *A61F 2002/30563* (2013.01); *A61F 2002/30578* (2013.01); *A61F 2002/30581* (2013.01); *A61F 2002/30688* (2013.01); *A61F 2002/30754* (2013.01); *A61F 2002/3863* (2013.01); *A61L 2300/406* (2013.01); *A61L 2300/41* (2013.01); *A61L 2300/414* (2013.01); *A61L 2300/602* (2013.01); *A61L 2300/64* (2013.01); *A61L 2400/10* (2013.01); *A61L 2430/06* (2013.01); *A61L 2430/24* (2013.01)

(58) Field of Classification Search
CPC .. A61F 2002/30069; A61F 2002/30075; A61F 2002/30563; A61F 2002/30581; A61F 2002/30586; A61F 2002/30757; A61F 2002/30761; A61F 2002/30764; A61F 2002/30766; A61F 2/30756; A61F 2002/30751
See application file for complete search history.

(56) References Cited

U.S. PATENT DOCUMENTS

| | | | | |
|---|---|---|---|---|
| 4,052,753 A * | 10/1977 | Dedo | ................ | A61F 2/38 623/14.12 |
| 4,219,892 A | 9/1980 | Rigdon | | |
| 4,344,193 A | 8/1982 | Kenny | | |
| 4,467,479 A * | 8/1984 | Brody | ................ | A61B 17/562 128/898 |
| 4,502,161 A * | 3/1985 | Wall | ................ | A61F 2/30756 606/286 |
| 4,919,667 A | 4/1990 | Richmond | | |
| 4,919,668 A * | 4/1990 | Rosenbaum | ......... | A61F 2/3099 623/17.17 |
| 4,932,969 A | 6/1990 | Frey et al. | | |
| 5,171,282 A * | 12/1992 | Pequignot | ........... | A61F 2/30907 623/20.35 |
| 5,195,542 A | 3/1993 | Gazielly et al. | | |
| 5,344,459 A * | 9/1994 | Swartz | ................ | A61F 2/3872 623/14.12 |
| 5,383,456 A | 1/1995 | Arnold et al. | | |
| 5,441,508 A | 8/1995 | Gazielly et al. | | |
| 6,056,777 A * | 5/2000 | McDowell | ......... | A61F 2/30724 623/18.11 |
| 6,110,211 A | 8/2000 | Weiss | | |
| 6,132,468 A * | 10/2000 | Mansmann | ............. | A61F 2/38 623/18.11 |
| 6,193,761 B1 | 2/2001 | Treacy | | |
| 6,248,110 B1 | 6/2001 | Reiley et al. | | |
| 6,258,126 B1 * | 7/2001 | Colleran | ................ | A61F 2/38 623/20.29 |
| 6,423,083 B2 | 7/2002 | Reiley et al. | | |
| 6,482,209 B1 | 11/2002 | Engh et al. | | |
| 6,783,546 B2 | 9/2004 | Zucherman et al. | | |
| 6,875,235 B2 * | 4/2005 | Ferree | ................ | A61F 2/34 623/17.11 |
| 7,001,385 B2 | 2/2006 | Bonutti | | |
| 7,291,169 B2 * | 11/2007 | Hodorek | ............. | A61F 2/30756 623/14.12 |
| 7,338,524 B2 | 3/2008 | Fell et al. | | |
| 7,491,235 B2 * | 2/2009 | Fell | ................ | A61F 2/30767 623/14.12 |
| 7,531,000 B2 | 5/2009 | Hodorek | | |
| 7,611,653 B1 | 11/2009 | Elsner et al. | | |
| 7,670,381 B2 * | 3/2010 | Schwartz | ............. | A61B 17/562 623/14.12 |
| 7,803,193 B2 | 9/2010 | Steinberg | | |
| 7,850,983 B2 | 12/2010 | Sevrain et al. | | |
| 7,972,380 B2 | 7/2011 | Linares | | |
| 7,976,578 B2 | 7/2011 | Marvel | | |
| 8,192,491 B2 | 6/2012 | Fox | | |
| 8,257,444 B2 * | 9/2012 | Linares | ................ | A61F 2/38 623/18.11 |
| 8,287,594 B2 * | 10/2012 | Cragg | ................ | A61F 2/3872 623/14.12 |
| 8,292,954 B2 | 10/2012 | Robinson et al. | | |
| 8,292,955 B2 | 10/2012 | Robinson et al. | | |
| 8,333,805 B2 * | 12/2012 | Williams, III | ........ | A61L 27/425 623/20.35 |
| 8,357,203 B2 | 1/2013 | White et al. | | |
| 8,361,147 B2 * | 1/2013 | Shterling | ............. | A61F 2/38 623/14.12 |
| 8,403,985 B2 * | 3/2013 | Hodorek | ................ | A61L 27/52 623/13.12 |
| 8,617,242 B2 * | 12/2013 | Philipp | ............. | A61F 2/30756 623/18.11 |
| 8,623,085 B2 * | 1/2014 | Gatt | ............. | A61F 2/30756 623/14.12 |
| 8,636,806 B2 | 1/2014 | Osman | | |
| 8,679,190 B2 * | 3/2014 | Myung | ............. | A61F 2/30756 623/13.11 |
| 8,709,089 B2 * | 4/2014 | Lang | ............. | A61F 2/30756 29/592 |
| 8,734,523 B2 * | 5/2014 | Trimmer | ............. | A61F 2/3868 623/20.33 |
| 8,747,479 B2 * | 6/2014 | McShane | ............. | A61F 2/389 623/20.31 |
| 8,764,830 B2 * | 7/2014 | Robinson | ............. | A61F 2/4606 623/14.12 |
| 8,771,363 B2 * | 7/2014 | Grotz | ............. | A61B 17/0642 623/18.11 |
| 8,834,568 B2 | 9/2014 | Shapiro | | |
| 8,882,847 B2 * | 11/2014 | Burdulis, Jr. | ........ | A61F 2/30942 623/20.32 |
| 8,945,222 B2 * | 2/2015 | Linares | ................ | A61F 2/30 623/17.11 |
| 8,979,938 B2 * | 3/2015 | Linares | ................ | A61F 2/38 623/14.12 |
| 8,999,000 B2 | 4/2015 | Hodorek et al. | | |
| 9,326,863 B2 * | 5/2016 | Linder-Ganz | ......... | A61F 2/4684 |
| 9,345,577 B2 * | 5/2016 | Vanleeuwen | ....... | A61F 2/30756 |
| 9,498,335 B2 * | 11/2016 | McCullen | ........... | A61F 2/30756 |
| 9,603,711 B2 * | 3/2017 | Bojarski | ............. | A61F 2/30942 |
| 9,662,218 B2 * | 5/2017 | Grotz | ................ | A61F 2/3859 |
| 9,700,971 B2 * | 7/2017 | Lang | ................ | B23P 19/04 |
| 9,737,406 B2 * | 8/2017 | Robichaud | .......... | A61F 2/30942 |
| 9,757,241 B2 * | 9/2017 | Grotz | ................ | A61L 27/54 |
| 9,808,345 B2 * | 11/2017 | Grotz | ................ | A61F 2/30721 |
| 9,848,987 B2 * | 12/2017 | Badylak | ................ | A61F 2/3099 |
| 9,913,724 B2 * | 3/2018 | Fox | ................ | A61F 2/3872 |
| 2002/0143402 A1 | 10/2002 | Steinberg | | |
| 2003/0093152 A1 * | 5/2003 | Pedersen | ............. | A61B 17/025 623/14.12 |
| 2003/0163202 A1 | 8/2003 | Lakin | | |
| 2003/0220649 A1 | 11/2003 | Bao et al. | | |
| 2004/0006393 A1 | 1/2004 | Burkinshaw | | |
| 2004/0024460 A1 * | 2/2004 | Ferree | ................ | A61F 2/34 623/17.12 |

(56) References Cited

U.S. PATENT DOCUMENTS

| | | | |
|---|---|---|---|
| 2004/0030398 A1* | 2/2004 | Ferree | A61F 2/34 623/20.32 |
| 2004/0039450 A1 | 2/2004 | Griner et al. | |
| 2004/0260396 A1* | 12/2004 | Ferree | A61F 2/28 623/17.12 |
| 2004/0267375 A1 | 12/2004 | Friedrichs | |
| 2005/0033424 A1* | 2/2005 | Fell | A61F 2/38 623/14.12 |
| 2005/0171604 A1* | 8/2005 | Michalow | A61F 2/38 623/14.12 |
| 2005/0182463 A1 | 8/2005 | Hunter et al. | |
| 2006/0024076 A1 | 2/2006 | Kato et al. | |
| 2006/0047341 A1 | 3/2006 | Trieu | |
| 2006/0058892 A1 | 3/2006 | Lesh et al. | |
| 2006/0122622 A1 | 6/2006 | Truckai et al. | |
| 2006/0122623 A1 | 6/2006 | Truckai et al. | |
| 2006/0190078 A1 | 8/2006 | Fell | |
| 2006/0235517 A1 | 10/2006 | Hodorek | |
| 2007/0016300 A1 | 1/2007 | Kuslich | |
| 2007/0078517 A1* | 4/2007 | Engh | A61B 17/025 623/20.3 |
| 2007/0100457 A1* | 5/2007 | Hyde, Jr. | A61B 17/88 623/18.12 |
| 2007/0100461 A1* | 5/2007 | Incavo | A61F 2/38 623/20.19 |
| 2007/0112428 A1 | 5/2007 | Lancial et al. | |
| 2007/0112458 A1 | 5/2007 | Kondo et al. | |
| 2007/0135920 A1 | 6/2007 | Ferree | |
| 2007/0150067 A1 | 6/2007 | Roger et al. | |
| 2007/0172506 A1* | 7/2007 | Nycz | A61F 2/30756 424/422 |
| 2007/0179607 A1 | 8/2007 | Hodorek et al. | |
| 2007/0276491 A1 | 11/2007 | Ahrens et al. | |
| 2007/0288095 A1 | 12/2007 | Wirtel et al. | |
| 2008/0071373 A1 | 3/2008 | Moltz | |
| 2008/0200989 A1 | 8/2008 | Cachia | |
| 2008/0208346 A1 | 8/2008 | Schwartz | |
| 2008/0234820 A1 | 9/2008 | Felt et al. | |
| 2008/0249638 A1 | 10/2008 | Asgari | |
| 2009/0043344 A1 | 2/2009 | Schlotterback | |
| 2009/0076605 A1 | 3/2009 | Linares | |
| 2009/0187252 A1 | 7/2009 | Howald | |
| 2009/0234453 A1 | 9/2009 | Steinberg | |
| 2009/0259313 A1* | 10/2009 | Elsner | B29C 70/48 623/14.12 |
| 2009/0259314 A1 | 10/2009 | Linder-Ganz et al. | |
| 2009/0306778 A1* | 12/2009 | Marvel | A61F 2/30756 623/14.12 |
| 2009/0312807 A1 | 12/2009 | Boudreault et al. | |
| 2010/0010114 A1 | 1/2010 | Myung et al. | |
| 2010/0023126 A1* | 1/2010 | Grotz | A61F 2/30721 623/14.12 |
| 2010/0042215 A1 | 2/2010 | Stalcup et al. | |
| 2010/0256758 A1 | 10/2010 | Gordon et al. | |
| 2011/0066243 A1 | 3/2011 | Rivin et al. | |
| 2011/0071640 A1* | 3/2011 | Linares | A61F 2/38 623/18.11 |
| 2011/0082424 A1 | 4/2011 | Barnhouse et al. | |
| 2011/0288642 A1* | 11/2011 | Forsell | A61F 2/3872 623/14.12 |
| 2012/0316645 A1* | 12/2012 | Grotz | A61F 2/08 623/14.13 |
| 2013/0018479 A1 | 1/2013 | Grotz | |
| 2013/0030542 A1* | 1/2013 | Grotz | A61B 17/0642 623/20.35 |
| 2013/0096691 A1 | 4/2013 | Myung et al. | |
| 2013/0138211 A1 | 5/2013 | Myung et al. | |
| 2013/0204377 A1 | 8/2013 | Samuelson et al. | |
| 2014/0222149 A1* | 8/2014 | Amis | A61F 2/3872 623/14.12 |
| 2014/0257500 A1* | 9/2014 | Grotz | A61B 17/0642 623/20.16 |
| 2014/0316526 A1* | 10/2014 | Grotz | A61L 27/54 623/20.17 |
| 2015/0127114 A1* | 5/2015 | Zhao | A61F 2/58 623/22.13 |
| 2015/0238318 A1* | 8/2015 | McCullen | A61F 2/30756 623/14.12 |
| 2015/0297350 A1* | 10/2015 | Robichaud | A61F 2/3859 623/20.32 |
| 2016/0228254 A1* | 8/2016 | Damle | A61F 2/38 |
| 2016/0367369 A1* | 12/2016 | Alotaibi | A61F 2/30756 |
| 2017/0014237 A1* | 1/2017 | Koenen | A61F 2/3872 |
| 2017/0056180 A1* | 3/2017 | Schmieding | A61F 2/30756 |
| 2017/0266012 A1* | 9/2017 | Grotz | A61F 2/3859 |
| 2017/0312088 A1* | 11/2017 | Grotz | A61L 27/54 |
| 2018/0028320 A1* | 2/2018 | Forsell | A61F 2/34 |
| 2018/0064544 A1* | 3/2018 | Grotz | A61F 2/3859 |

FOREIGN PATENT DOCUMENTS

| | | |
|---|---|---|
| EP | 2130517 A1 | 12/2009 |
| EP | 2750629 B1 | 7/2016 |
| FR | 2747914 A | 10/1997 |
| FR | 2803190 A1 | 7/2001 |
| KR | 20050100511 A | 10/2005 |
| WO | WO2004100839 A1 | 11/2004 |
| WO | WO2007125060 | 11/2007 |
| WO | WO2009052292 A1 | 4/2009 |
| WO | WO2008111073 A2 | 9/2009 |
| WO | WO2010011338 A2 | 1/2010 |
| WO | WO2010059098 A1 | 5/2010 |
| WO | WO2011091005 A2 | 7/2011 |

OTHER PUBLICATIONS

Co-pending U.S. Appl. No. 14/936,562, filed Nov. 9, 2015.
U.S. Appl. No. 13/514,539 Office Action dated Jul. 8, 2015.
Co-pending U.S. Appl. No. 15/608,885, filed May 30, 2017.
U.S. Appl. No. 13/514,539 Office action dated Dec. 9, 2014.
U.S. Appl. No. 13/574,517 Office action dated Mar. 5, 2015.
PCT/US11/021674 International Search Report and Written Opinion dated Sep. 23, 2011.
PCT/US2010/58977 International Preliminary Report on Patentability dated Feb. 7, 2011.
PCT/US2011/021673 International Preliminary Report on Patentability dated Sep. 16, 2011.
PCT/US2012/53207 International Preliminary Report on Patentability dated Feb. 14, 2013.
U.S. Appl. No. 13/574,517 Office action dated Aug. 15, 2014.
PCT/US09/04305 International Preliminary Report on Patentability dated Jan. 25, 2011.
PCT/US09/04305 International Search Report dated Jan. 19, 2010.
PCT/US11/021674 Search Report and Written Opinion dated Sep. 23, 2011.
PCT/US11/021673 Search Report and Written Opinion dated Sep. 16, 2011.
U.S. Appl. No. 12/460,703 Office Action dated Jun. 7, 2013.
U.S. Appl. No. 12/460,703 Office Action dated Aug. 10, 2011.
U.S. Appl. No. 12/460,703 Office Action dated Nov. 21, 2013.
U.S. Appl. No. 12/460,703 Office Action dated Oct. 2, 2012.
U.S. Appl. No. 12/460,703 Office Action dated Jan. 31, 2012.
U.S. Appl. No. 13/514,539 Office Action dated Feb. 7, 2014.
U.S. Appl. No. 13/514,539 Office Action dated May 16, 2014.
U.S. Appl. No. 13/574,499 Office Action dated Dec. 2, 2013.
U.S. Appl. No. 13/574,517 Office Action dated Feb. 6, 2014.

* cited by examiner

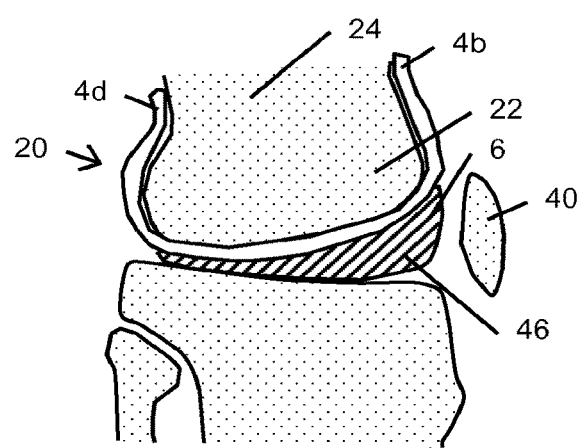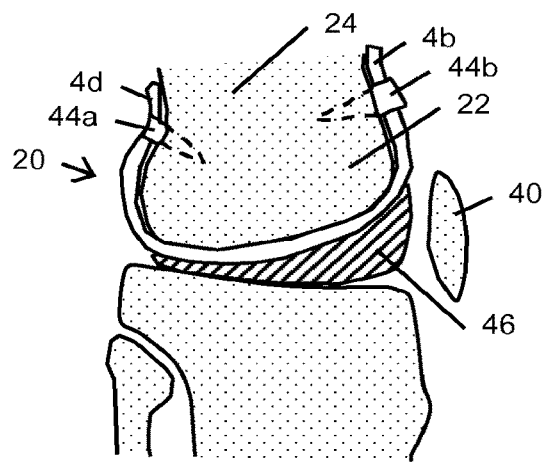
FIG 10A          FIG 10B
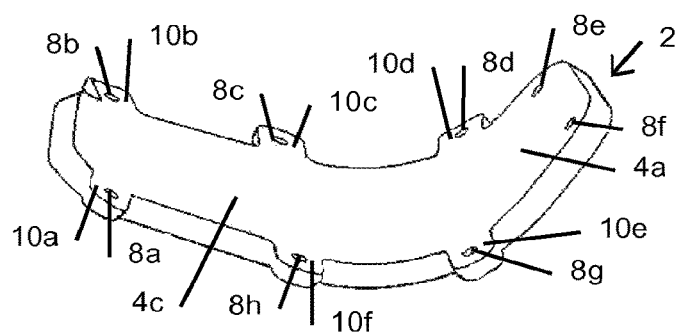
FIG 11A
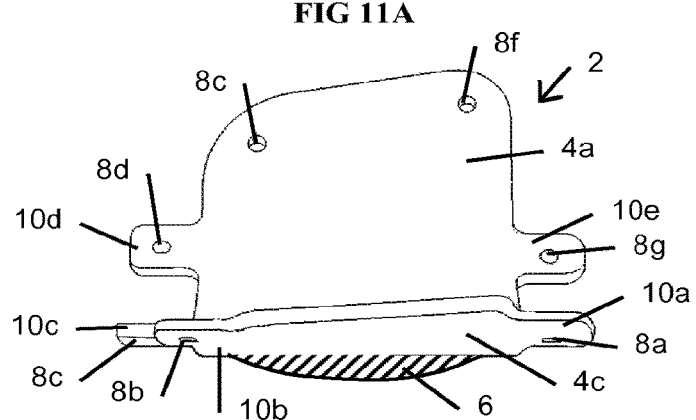
FIG 11B

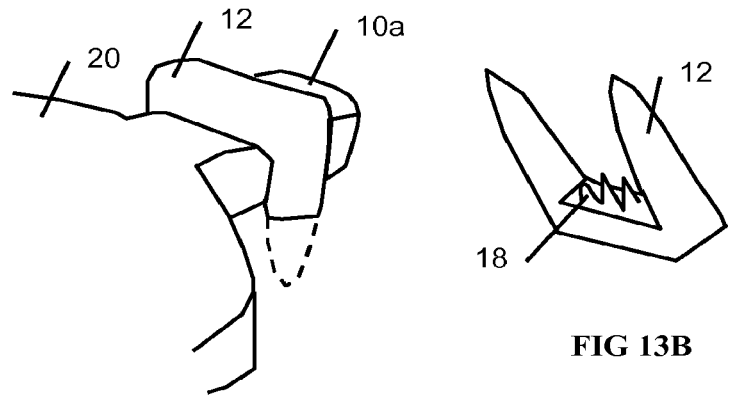
FIG 13A
FIG 13B
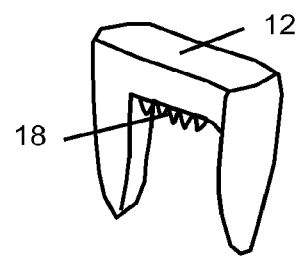
FIG 13C
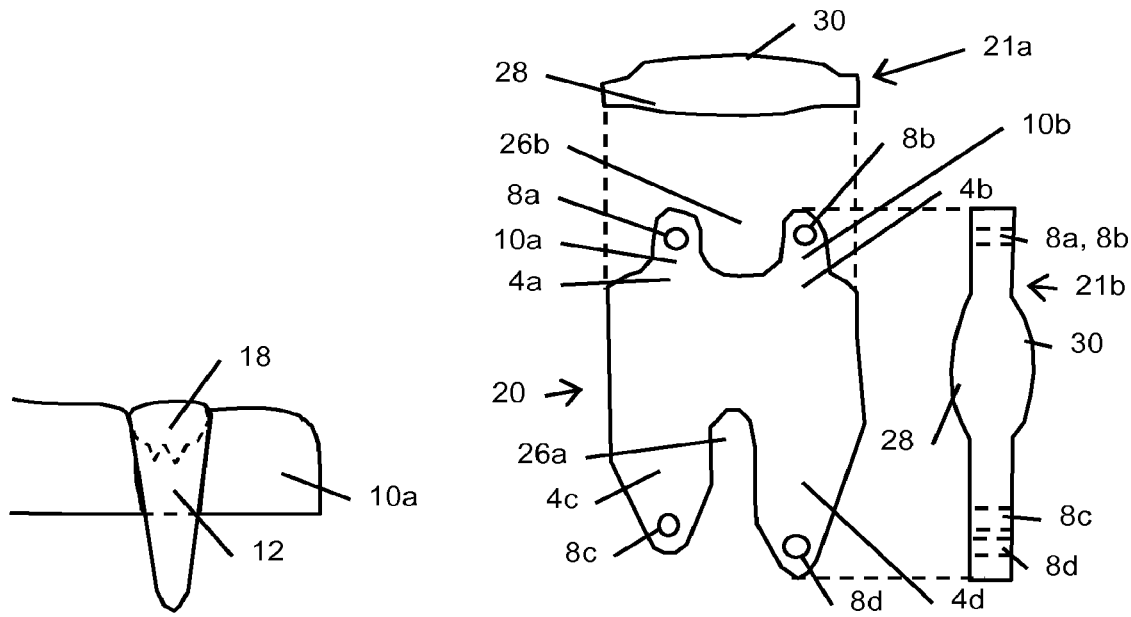
FIG 13D
FIG 14

RESILIENT INTERPOSITIONAL ARTHROPLASTY DEVICE

CROSS REFERENCE TO RELATED APPLICATIONS

This application claims the benefit of U.S. Non-provisional Ser. No. 14/239,992 filed on Jun. 5, 2014, which is the National Stage of International Application No. PCT/US12/053207, filed on Aug. 30, 2012, which claims the benefit of U.S. Provisional Application No. 61/530,324 filed on Sep. 1, 2011, all of which are incorporated herein by reference in their entirety.

BACKGROUND OF THE INVENTION

This invention relates to arthroplasty, and more particularly, to an implant for use in arthroplasty when hyaline articular cartilage is damaged, it breaks down and joint space is lost. Inflammatory enzymes such as from the Cox-1, Cox-2 and/or 5-Lox systems are released and loose bodies form adding to the degradation of joint function. Such joint damage is conventionally treated by physical therapy, analgesics, pain medication and injections. When these treatments fail, the traditionally accepted treatment option is arthroplasty implantation or replacing the joint with an artificial joint construct. Current arthroplasty techniques typically use "plastic and metal" implants that are rigid and which ultimately fail due to loosening or infection or debris from wear. Conventional materials for the artificial joint components include chrome-cobalt-molybdenum alloy (metal) and high molecular weight polyethylene (plastic). Each is often fixed by a cement-like mixture of methyl methacrylate to the ends of the bones that define the joint that is the subject of the arthroplasty, or coated with a surface that enables bone in-growth. Current hip joint replacements typically last about 10-15 years and knee replacements typically last about 5-10 years. Ankle joint replacements, on the other hand, are not very successful, and often fail in the first several years after surgery.

Conditions requiring arthroplasty include traumatic arthritis, osteoarthritis, rheumatoid arthritis, osteonecrosis, and failed surgical procedures.

SUMMARY OF THE INVENTION

The present invention is directed to an orthopedic implant configured for deployment between opposing members of a joint structure that addresses many of the shortcomings of prior artificial joints. The arthroplasty implants embodying features of the invention are configured to preserve joint motions while removing the pain and dysfunction following the development of arthritis or joint injury. The arthroplasty implant in accordance with the present invention achieves improved physiologic motion and shock absorption during gait and acts as a resilient spacer between moving bones during limb movement. The combined characteristics of the implant include anatomic design symmetry, balanced rigidity with variable attachment connections to at least one of adjacent normal structures, and durability which addresses and meets the needs for repair or reconstruction thus far missed in the prior art. The implant should be secured to at least one of the bones of the joint structure.

Provided herein is a resilient implant for implantation into human or animal joints to act as a cushion allowing for renewed joint motion. The implant may endure variable joint forces and cyclic loads while reducing pain and improving function after injury or disease to repair, reconstruct, and regenerate joint integrity. The implant may be deployed in a prepared debrided joint space, secured to at least one of the joint bones and expanded in the space, molding to surrounding structures with sufficient stability to avoid extrusion or dislocation. The implant may have opposing walls that move in varied directions, and an inner space filled with suitable filler to accommodate motions which mimic or approximate normal joint motion. The implant may pad the damaged joint surfaces, may restore cushioning immediately and may be employed to restore cartilage to normal by delivering regenerative cells.

Provided herein is a resilient interpositional arthroplasty implant for application into human or animal joints to pad cartilage defects, cushion joints, and replace or restore the articular surface, preserving joint integrity, reducing pain and improving function. The implant may endure variable joint compressive and shear forces, and millions of cyclic loads, after injury or disease requires intervention. The implant may repair, reconstruct, and regenerate joint anatomy in a minimally morbid fashion, with physiologic solutions that improve upon the rigid existing joint replacement alternatives of plastic and metal. In cases where cells have been used for joint resurfacing requiring massive periosteal harvesting for containment, the polymer walls of some embodiments of the implant can capture, distribute and hold living cells until aggregation and hyaline cartilage regrowth occurs. The implant may be deployed into a prepared debrided joint space, molding and conforming to surrounding structures with sufficient stability to avoid extrusion or dislocation. Appendages of the implant may serve to repair or reconstruct tendons or ligaments. Appendages of the implant may serve to repair or reconstruct fibrocartilage as in menisci, or the labrum tissues of hips or shoulders. The implant may have opposing walls that move in varied directions, and an inner space, singular or divided, filled with suitable gas, liquid, and/or complex polymer layers as force-absorbing mobile constituents, such than robust valid and reliable joint motion is enabled.

Provided herein is a resilient orthopedic implant configured for deployment between a first bone and at least one second bone of a joint, the implant comprising a balloon comprising a first portion that is configured to engage the first bone of the joint, a second portion that is configured to engage at least one second bone of the joint, a side portion connecting the first portion and the second portion, in which the side portion facilitates relative motion between the first portion and the second portion, and an interior that is optionally inflatable with a first inflation medium; and a first appendage configured to couple the balloon to the first bone of the joint. As used herein a balloon may also and/or alternatively be called a balloon. In the embodiments wherein the balloon is not inflated, the uninflated balloon may accommodate movement between portions of the balloon wall or a first wall of the balloon and a second wall of the balloon. Alternatively or additionally, the uninflated balloon may provide the opportunity for later inflation following implantation. In some embodiments, the materials of the implant allow for internal expansion. In other embodiments, material layers may be fixed in apposition so as to encourage strength and anti-creep, as with a mesh. In certain embodiments, the fixed layer itself has pockets containing gas or gel (e.g. viscolubricants) or liquid or a pharmacologic. In other embodiments, the implant walls are contiguous having no discernable pockets, vacuoles or chambers.

Provided herein is a resilient orthopedic implant configured for deployment between a femur and a tibia of a knee joint, the implant comprising a balloon comprising a first portion that is configured to engage a medial condyle and a lateral condyle of the femur of the knee joint, a second portion that is configured to engage the tibia of the knee joint, a side portion connecting the first portion and the second portion, in which the side portion facilitates relative motion between the first portion and the second portion, and an interior that is optionally inflatable with a first inflation medium; and a first appendage configured to couple the balloon to the femur of the knee joint.

In some embodiments, the implant comprises at least one attachment element in the intercondylar notch. In some embodiments, the implant comprises at least one attachment element in the medial region of the intercondylar notch. In some embodiments, the implant comprises at least one attachment element in the lateral region of the intercondylar notch. In some embodiments, the implant comprises at least one attachment element superiorly at the distal end of the femur anteriorly. In some embodiments, the implant comprises at least one posterior reign configured to cinch up the implant from inside a posterior intercondylar notch toward a connection site around the femur. In some embodiments, the implant comprises at least one suture-like lanyard configured to cinch up the implant from inside a posterior intercondylar notch toward a connection site around the femur.

In some embodiments, at least two of first portion, the second portion, and the side portion are contiguous. In some embodiments, the first portion comprises a first wall, the second portion comprises a second wall, and the side portion comprises a side wall.

In some embodiments, the implant comprises an inflation port in communication with the interior of the balloon for inflation of the interior of the balloon with the first inflation medium. In some embodiments, the interior comprises a plurality of inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium. In some embodiments, the first inflation medium imparts at least one of rigidity in the implant and cushion in the implant. In some embodiments, there is no inflatable chamber and the cushioning is a result of compliant materials of the walls themselves In some embodiments, the implant comprises a second appendage coupling the balloon to at least one of: the femur of the joint and the tibia of the joint.

Provided herein is an implant configured for deployment between a femur and a tibia of a knee joint, the implant comprising a balloon comprising a first portion that is configured to engage at least one condyle of the femur of the knee joint, a second portion that is configured to engage the tibia of the knee joint, a side portion connecting the first portion and the second portion, in which the side portion facilitates relative motion between the first portion and the second portion, and an interior that is optionally inflatable with a first inflation medium; and a first appendage configured to couple the balloon to the femur of the knee joint.

In some embodiments, the at least one condyle is the medial condyle. In some embodiments, the at least one condyle is the lateral condyle. In some embodiments, the retropatellar surface could be the anatomic region padded. In some embodiments, the tibia-medial or lateral or both is capped. In certain knee implant embodiments, the implant articulates against cartilage of the first bone, second bone, and/or the third bone In some embodiments, the balloon is at least one of: at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 4 cm in diameter, at most about 4.25 cm in diameter, at most about 4.5 cm in diameter, at most about 4.75 cm in diameter, at most about 5 cm in diameter, at most about 5.25 cm in diameter, at most about 5.5 cm in diameter, at most about 5.75 cm in diameter, at most about 6 cm in diameter, at most about 6.25 cm in diameter, at most about 6.5 cm in diameter, at most about 6.75 cm in diameter, at most about 7 cm in diameter, at most about 7.25 cm in diameter, at most about 7.5 cm in diameter, at most about 7.75 cm in diameter, at most about 8 cm in diameter, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in length along the longest length of the balloon, at most about 4.5 cm in length along the longest length of the balloon, at most about 4.75 cm in length along the longest length of the balloon, at most about 5 cm in length along the longest length of the balloon, at most about 5.25 cm in length along the longest length of the balloon, at most about 5.5 cm in length along the longest length of the balloon, at most about 5.75 cm in length along the longest length of the balloon, at most about 6 cm in length along the longest length of the balloon, 6.25 cm in length along the longest length of the balloon, at most about 6.5 cm in length along the longest length of the balloon, at most about 6.75 cm in length along the longest length of the balloon, at most about 7 cm in length along the longest length of the balloon, at most about 7.25 cm in length along the longest length of the balloon, at most about 7.5 cm in length along the longest length of the balloon, at most about 7.75 cm in length along the longest length of the balloon, and at most about 8 cm in length along the longest length of the balloon.

In some embodiments, the first portion comprises a first wall, the second portion comprises a second wall, and the side portion comprises a side wall.

In some embodiments, the implant comprises an inflation port in communication with the interior of the balloon for inflation of the interior of the balloon with the first inflation medium. In some embodiments, the balloon is punctured to inflate the interior of the balloon with the first inflation medium. In some embodiments, the balloon is self-sealing. In some embodiments, the balloon is self-sealing upon inflation of the interior of the balloon with the first inflation medium. In some embodiments, the implant comprises a seal capable of closing the interior of the balloon. In some embodiments, there is no balloon and inflation into a wall of the implant expands the implant with a compressible material. In some embodiments, inflation is achieved via a needle or cannula that delivers the inflation medium such as lubricating materials or medications or a combination thereof, or other inflation mediums. In some embodiments, despite addition of an inflation medium, there is no ballooning effect or change in thickness in the device, as the inflation medium itself fills empty spaces in the wall (or walls) into which it is delivered. In some embodiments, the implant comprises an inflation port in communication with the interior of the balloon for inflation of the interior of the balloon with the first inflation medium. In some embodiments, the interior comprises a plurality of inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium. In some embodiments, the first inflation medium imparts at least one of rigidity in the implant and cushion in the implant. In some embodiments the chambers are constructed as part of a trabecular polymer framework or honeycomb or foam or alveolar network. The chambers may be adapted to increase the surface area of available polymer for disbursement or absorption.

In some embodiments, the implant comprises a second appendage coupling the balloon to at least one of: the femur of the joint and the tibia of the joint. In some embodiments, the implant comprises at least one attachment element in the intercondylar notch. In some embodiments, the implant comprises at least one attachment element in the medial region of the intercondylar notch. In some embodiments, the implant comprises at least one attachment element in the lateral region of the intercondylar notch. In some embodiments, the implant comprises at least one attachment element superiorly at the distal end of the femur anteriorly. In some embodiments, the implant comprises at least one posterior reign configured to cinch up the implant from inside a posterior intercondylar notch toward a connection site around the femur. In some embodiments, the implant comprises at least one suture-like lanyard configured to cinch up the implant from inside a posterior intercondylar notch toward a connection site around the femur.

In some embodiments, the implant is fabricated to resemble a certain anatomic region over which the implant is stretched or pulled into place. The implant then may settle into its angle of repose via inherent elasticity. In some embodiments the ambient environment of the joint via exposure to serum or temperature or acidity has a specified effect on the implant materials such as increasing the implant malleability that affects implant performance.

Provided herein is an implant configured to patch a defect of a bone of a knee joint, the implant comprising a balloon configured to engage the defect of the bone of the knee joint and comprising an interior that is optionally inflatable with a first inflation medium; and a first appendage configured to couple the balloon to the bone of the knee joint.

In some embodiments, at least one of the appendage and the balloon are configured to replace cartilage.

In some embodiments, the balloon is at least one of: at most about 0.5 cm in diameter, at most about 0.75 cm in diameter, at most about 1 cm in diameter, at most about 1.25 cm in diameter, at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 0.5 cm in length along the longest length of the balloon, at most about 0.75 cm in length along the longest length of the balloon, at most about 1 cm in length along the longest length of the balloon, at most about 1.25 cm in length along the longest length of the balloon, at most about 1.5 cm in length along the longest length of the balloon, at most about 1.75 cm in length along the longest length of the balloon, at most about 2 cm in length along the longest length of the balloon, at most about 2.25 cm in length along the longest length of the balloon, at most about 2.5 cm in length along the longest length of the balloon, at most about 2.75 cm in length along the longest length of the balloon, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, and at most about 4 cm in length along the longest length of the balloon.

In some embodiments, the interior comprises a plurality of inflatable chambers. In some embodiments, the interior comprises a plurality of individually inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium.

In some embodiments, the balloon or a chamber thereof may be secondarily inflated, deflated, or a combination thereof in situ.

In some embodiments, the implant comprises an in-growth matrix on at least a portion of the implant adjacent the femur. In some embodiments, the in-growth matrix comprises living chondrocytes. In some embodiments, the implant is configured to release the chondrocytes over time. In some embodiments, the implant comprises a bioabsorbable polymer configured to release the chondrocytes over time. In some embodiments, the implant comprises a polymer configured to release the chondrocytes over time, wherein the polymer is not bioabsorbable. In some embodiments, the in-growth matrix comprises cells. In some embodiments, the in-growth matrix comprises at least one of: stem cells, differentiated cells, pluripotent cells, post-mitotic cells. In some embodiments, the cells restore an articular surface of the femur. In other embodiments, the cells repair an articular surface of the femur. In some embodiments, the implant comprises a bioabsorbable polymer configured to release the cells over time. In some embodiments, the implant comprises a polymer configured to release the cells over time, wherein the polymer is not bioabsorbable. In some embodiments, the in-growth matrix comprises at least one of: autologous cells, allograph cells, and xenograph cells to restore an articular surface of the femur. In some embodiments, the in-growth matrix comprises at least one of: autologous cells, allograph cells, and xenograph cells to repair an articular surface of the femur. In some embodiments, the in-growth matrix comprises a pharmacologic substance. In some embodiments, the patch implant comprises a matrix that is coated with a hydrophilic or a hydrophobic polymer. In some embodiments the patch is vessicular with or without matrices in the wall components. In certain embodiments, the patch is a solid compliant material. In some embodiments, the walls or material construct is responsive or performs in a dynamic fashion to exogenous joint forces. For non-limiting example, in bone under normal physiologic stress of bearing weight, calcification yields sufficient bone density so as to deter fracture. However, in circumstances wherein prolonged dearth of weight bearing stress is produced by immobilization the bone becomes osteoporotic and pathologic. The implant herein may have smart features to adjust to stimulate healing and tissue regeneration. In some embodiments such materials can be composed of macromolecules or dendritic connections that regulate permeability and transfer of adjacent media.

In some embodiments, the implant comprises couplers that couple the appendage to the femur. In some embodiments, the coupler is bioabsorbable. In some embodiments, the coupler is at least one of: a screw, a snap, a washer, a suture, a suture anchor, a rivet, a staple, a staple having teeth, a magnet, an electromagnet, a microminiature transmitter that regulates implant fixation or performance responsive to patient need as perceived by the patient or a care giver, a stabilizer, a glue, a hook, a wire, a string, a lasso, a lanyard, a spike, and combinations thereof. The implant may also and/or alternatively be attached via bone in-growth. In some embodiments, the implant is attached via bone in-growth as described in Vasanji A, In vivo bone growth assessment in preclinical studies and clinical trials, Bonezone, 2012, p. 12-17, herein incorporated by reference in its entirety.

In some embodiments, the implant comprises a pharmacologic agent. In some embodiments, the pharmacologic agent is on a surface of the implant adjacent the femur. In some embodiments, the pharmacologic agent is released from the implant over time. In some embodiments, the pharmacologic agent is released from within the implant over time. In some embodiments, the pharmacologic agent is released from within the balloon over time. In some embodiments, the agent is released as a combination of vessicular and matrix origins using internal or external stimuli from normal or exogenous sources.

In some embodiments, the first inflation medium imparts rigidity in the implant. In some embodiments the implant comprises a bone cement. In some embodiments, the implant comprises methyl methacrylate. In some embodiments, the first inflation medium imparts cushion in the implant.

In some embodiments, the inflation medium is compressible. In some embodiments, the inflation medium comprises a viscolubricant. In some embodiments, the inflation medium comprises a pharmacologic substance. In some embodiments, the inflation medium comprises an NSAID. In some embodiments, the inflation medium comprises chondrocytes. In some embodiments, the inflation medium comprises cells.

In some embodiments, at least a portion of the implant is configured to anneal to a periphery of a cartilage defect.

In some embodiments, the implant comprises vacuoles of pharmacologic substances. In some embodiments, the vacuoles may be on a bone-engaging portion of the implant. In some embodiments, the implant comprises bubbles comprising an active substance such as a pharmacologic substance or other active agent. In some embodiments, the active agent comprises at least one of: stem cells, growth factors, antibiotics, antifungals, antituberculous, antitumor, antigout agents and viscolubricants. In some embodiments, the active agent comprises iatrigenically gene mutated cells.

In some embodiments, the implant comprises enzyme absorptive microscopic sponges that could be sucked out or evacuated at or around the time of implant delivery to the joint.

In some embodiments, the interior comprises a honeycomb structure. In some embodiments, the interior comprises a mesh structure. In some embodiments, the interior comprises a sponge structure. In some embodiments the implant comprises a sponge structure. In some embodiments the implant comprises a compliant membrane.

In some embodiments, the implant comprises spaces filled with an active substance such as a pharmacologic substance or other active substance. In some embodiments, the implant comprises spaces for deliverables (e.g., biologics, antibodies, cells, pharmacologic substances, biomolecules, molecules, compounds). In some embodiments, the implant comprises spaces for compressibles (e.g., gas, air). In some embodiments, the spaces comprise nanovesicles. In some embodiments, the nanovasicles comprise deliverables (e.g., biologics, antibodies, cells, pharmacologic substances, biomolecules, molecules, compounds). In some embodiments, the nanovesicles comprise compressibles (e.g., gas, air).

In some embodiments, the implant comprises a second appendage coupling the balloon to the first bone of the joint. In some embodiments, the implant comprises a second appendage coupling the balloon to at least one second bone of the joint. In some embodiments, the implant comprises a second appendage configured to couple at least one of the first portion, the second portion, and the side portion to at least one of the first bone and at least one second bone of the joint. In some embodiments, the first appendage and the second appendage are configured to provide ligamentary-like support to the first bone and the at least one second bone of the joint. In some embodiments, the first appendage and the second appendage are configured to provide ligamentary-like support to the joint. In some embodiments, the first appendage and the second appendage are configured to provide tendon-like support to the first bone and the at least one second bone of the joint. In some embodiments, the first appendage and the second appendage are configured to provide tendon-like support to the joint.

In some embodiments, the implant is configured to fit within a cannula having a distal end inner diameter of at most 10 millimeters. In some embodiments, the implant is configured to fit within a cannula having a distal end inner diameter of at most 9 millimeters. In some embodiments, the implant is configured to fit within a cannula having a distal end inner diameter of at most 5 millimeters. In some embodiments, the implant may be configured to be introduced surgically arthroscopically as with the cannula 10 mm in diameter or may be introduced through minimal invasive surgery via a large conduit and plunger requiring a small arthrotomy several centimeters in diameter. In some embodiments routine open surgical insertion with a larger wound may be necessary depending on clinical condition, complexity and surgeon choice.

In some embodiments, the implant is configured to fold in order to fit within a cannula having a distal end inner diameter of at most 10 millimeters. In some embodiments, the implant is configured to fold in order to fit within a cannula having a distal end inner diameter of at most 9 millimeters. In some embodiments, the implant is configured to fold in order to fit within a cannula having a distal end inner diameter of at most 5 millimeters.

In some embodiments, the implant is configured to be delivered to a joint through a cannula having a distal end inner diameter of at most 10 millimeters. In some embodiments, the implant is configured to be delivered to a joint through a cannula having a distal end inner diameter of at most 9 millimeters. In some embodiments, the implant is configured to be delivered to a joint through a cannula having a distal end inner diameter of at most 5 millimeters.

In some embodiments, the implant is configured to fold in order to fit within a cannula having a distal end inner diameter of at most 10 millimeters. In some embodiments, the implant is configured to fold in order to fit within a cannula having a distal end inner diameter of at most 9 millimeters. In some embodiments, the implant is configured to deliver by dissolution of the implant material. In some embodiments, the implant is configured to deliver by release through pores of the implant. In some embodiments, the implant is configured to deliver by release through spaces of the implant. In some embodiments, the implant is configured to deliver by release through nanovesicles of the implant. In some embodiments, the implant is configured to deliver by fracture of a vacuole by a catalyst such as ultrasound or pressure or other fracturing catalyst. In some embodiments the release of contents may be over time as a function of normal cumulative limb use forces.

In some embodiments, the implant is configured to at least one of: pad cartilage, cushion the joint, deliver a pharmacologic substance, remove noxious enzymes, debride upon implantation, debride the joint following implantation, deliver a therapeutic substance, deliver a biologic substance, and deliver living stem cells. In some embodiments, the implant is configured to deliver a cell or tissue to a bone or surrounding tissue. In some embodiments, the cell is at least one of: stem cell, differentiated cell, pluripotent cell, and post-mitotic cell. In some embodiments, the implant is configured to deliver a chemotherapeutic agent to a bone or other surrounding tissues. In some embodiments, the implant is configured to deliver an anti-infectious medication to a bone or other surrounding tissues. In some embodiments, the implant is configured to deliver at least one of an antibiotic, antifungals, and analgesics agent. In some embodiments, the implant is configured to deliver an antibody. In some embodiments the implant is configured as a targeting structure for treatment of proximate pathophysiology. In some embodiments, the implant comprises a transmitter or a sensor that can emit or receive actionable instruction. In some embodiments, the implant comprises a sensor, for non-limiting example: a gauge, camera, fiberoptic, or other meter, to provide information of clinical relevance as it relates to proximate tissue. In some embodiments, the information received from the implant is transferred to the patient to enhance wound healing or other desired effects.

In some embodiments, the implant is configured to be selectively inflated to realign limbs.

Provided herein is a method comprising: implanting a knee implant as described herein into a subject, wherein the implant reverses arthritis in the subject.

Provided herein is a method comprising: implanting a knee implant as described herein into a knee joint of a subject and treating a component of the knee joint of the subject with at least one of an allograph tissue, an autograph tissue, and an xenograph tissue. In some embodiments, the implanting step is at least one of: prior to the treating step, simultaneous with the treating step, and following the treating step.

Provided herein is a method comprising: implanting a knee implant as described herein into a subject, wherein the implant at least one of: restores joint function and controls arthopathies. In some embodiments, the implanting spares existing anatomy.

Provided herein is a method comprising: debriding a femur condyle of a knee joint of a subject, and implanting a knee implant as described herein into the knee joint of the subject, whereby the implant is configured to anneal to the cartilage of the subject. In some embodiments, the debriding is achieved by steam application.

Provided herein is a method comprising implanting a knee implant as described herein into a joint previously treated with a joint replacement. In some embodiments, the method comprises removing the joint replacement prior to implanting the knee implant. In some embodiments, the method comprises clearing infectious matter from the joint and/or surrounding tissues. In some embodiments, the method comprises implanting a second implant of any implant described herein following removing the implant previously implanted in the joint. In some embodiments, the method comprises replacing the joint of the subject following removing the implant previously implanted in the joint. In some embodiments, the method comprises debriding the bone of the joint, and implanting an implant of any implant described herein. In some embodiments, the method comprises repeating the debriding and implanting steps.

In some embodiments, the implant is delivered non-arthroscopically through an incision that is at least 1 centimeter long. In some embodiments, the implant is delivered through an incision that is over about 10 centimeters long. In some embodiments, the implant is delivered through an incision that is at up to about 40 centimeters long.

In some embodiments, the implant replaces periosteum.

In some embodiments, the resilient implant embodying features of the invention has a first wall configured to be secured to a first bone of the joint structure by one or more appendages such as a skirt or one or more tabs and a second wall configured to engage a second and usually opposing bone of the joint structure. A side wall extends between the first and second walls of the implant and together with the first and second walls preferably defines at least in part an inner chamber or space between the first and second walls. The implant is configured to provide linear or curvilinear and/or rotational motion between the first and second bones which mimics or approximates the natural motion between these bones. The inner chamber or space is configured to maintain a filler material therein such as an inflation fluid or a resilient material and preferably to maintain spacing and provide support between the interior of the first and second walls to avoid significant contact therebetween. The walls of the implant are preferably sealed about the periphery thereof to maintain the interior chamber in a sealed condition to avoid loss of inflation fluid or filling media. The side wall or walls may be formed from the edges or periphery of the first and second walls. The properties of the implant walls and the interior are controlled to provide the particular resiliency desired for the joint in which the implant is to be placed as well as any desired motion between the first and second walls. A conduit may extend from a source of inflation fluid or other filling medium to the interior of the implant to facilitate expansion of the implant after deployment within the joint. The inflation fluid may be a gas, a liquid, a gel, a slurry, or a fluid that becomes a suitable resilient solid such as a curable polymer. Selection of the inflation or interior filling medium may depend upon the nature of the joint structure in which the implant is to be deployed, its anatomy, pathophysiology, and the properties of the implant material.

There may be several alternative embodiments depending upon the site in which the implant is to be deployed. For example, the polymer forming the side wall may be semi-compliant or elastic and the inflation fluid may be incompressible (e.g., a liquid). Alternatively, the polymer forming the side wall may be non-compliant (non-elastic) and the inflation fluid or filling medium may be compressible, e.g., a gas or a resilient polymeric foam or sponge-like solid that may have a closed cell structure. The first and second walls of the implant need not have the same properties as the side wall. For example, parts of the implant such as the side wall portion may be compliant and the first and second wall portions in contact with the bone or other joint structure may be non-compliant. Additionally, the various walls or portions thereof may also be reinforced with non-compliant or semi-compliant polymer strands, beads or gel coating such as biologic or polymer latticework. The thicknesses of the first, second and side walls may be varied to accommodate for the needs of the joint structure from the standpoint of strength, elasticity and wear resistance. Moreover, the walls of the implant may be provided with joint tissue regeneration agents that rebuild the joint structure in which the implant is deployed. The regeneration agent may be incorporated into the wall of the implant prior to delivery or placed between the surface of the implant and the joint structure which it contacts after delivery. All or part of the walls of the implant may also be made of a biodegradable polymer, by minimally manipulated autograph, allograph or xenograph tissues, or a combination thereof. The method of surgery may incorporate a progressive application of the implant embodiments depending upon clinical needs. The walls of the implant may serve one or more functions, including but not limited to filling space, attachment, strengthening, and any physiological function.

The implant is preferably formed of suitable biocompatible polymeric materials, such as Chronoflex (e.g., ChronoFlexAR®, ChronoFlex AL®, ChronoFlec C®), which is a family of thermoplastic polyurethanes based on a polycarbonate structure (Al, the aliphatic version, Ar, the aromatic version and C, the casting version) available from AdvanSource Biomaterials, Corp. Other polymers include BIONATE 80, 80A, 90A, 75D, 65D, 55D, 55 or 56, BIONATE I, or BIONATE II, which are also thermoplastic polyurethane polycarbonate copolymers, available from PTG Medical LLC., an affiliate of the Polymer Technology Group located in Berkeley, Calif. Other commercially available polymers include PurSil® (e.g., PurSil® 10, 20, 35, 40 80A, AL-10 75A) which is a thermoplastic silicone polyether urethane, CarboSil® (e.g., CarboSil® 10 90A, 20 55D, 20 80A, 20 90A, 40 90A, 5) which is a thermoplastic silicone polycarbonate urethane, Elasthane™ (e.g., Elasthane™ 55D, 75D, 80A) which is an aromatic biomedical polymer and Biospan which is a segmented polyurethane. These polymers are available as tubing, molded or dipped components, solution, pellets, as a casting and as a cast film for the side and first and second walls. The implant may be formed by casting, blow molding or by joining sheets of polymeric material by adhesives, laser welding and the like. Other methods of forming the implant may also be suitable. Example methods include melting beads and compression molding. The walls may also be provided with reinforcing strands which are located on the surface of the walls or incorporated within the walls. The implant material should be biocompatible, non-toxic, and non-carcinogenic and should be resistant to particulation.

The present invention provides an improved joint implant which is designed to endure variable joint forces and cyclic loads enabling reduced pain and improved function. Depending upon the particular joint involved there may be linear or curvilinear motion between the first and second walls, rotational motion between the first and second walls or both linear and curvilinear motion and rotation motion between the first and second walls. Preferably, a space is maintained between the inner surfaces of the first and second walls to avoid erosion and wear there between. The walls may be opposite sides of the same solid.

The resilient arthroplasty implant embodying features of the invention is preferably deployed as a minimally invasive procedure to deliver the implant into a prepared space in a preselected joint structure, where upon it is inflated to create a cushion, to cover damaged or arthritic cartilage and to be employed to deliver stem cells or living chondrocytes or other tissue regeneration agents. The goal of such deployment is to reduce pain and improve function, to reverse arthritis, to fill in osteochondral defects succinctly, thereby avoiding living with both dysfunctional and ablative metal/plastic prostheses or the pathophysiologic state necessitating the procedure. The operative plan is simple, systematic, and productive of new joint space with regrowth potential involving joint debridement by routine arthroscopic coblation, electronic chondroplasty methods or steam application, followed by implantation of the implant. The implant provides three things, namely a covering or patch for the damaged or worn joint surface, an inflated cushion to pad gait via inflation or compliant polymer as in normal walking in the lower extremity, and delivery of regenerative cells on the cartilage remnant surface. The stem cells may be injected as the implant is being expanded and/or directed into the adjacent hyaline cartilage via an implant coating or perfused cell template. Viscolubricants such as Synvisc or Hyalgan, analgesics such as Lidoderm, anti-inflammatory and/or antibiotic coatings as well as those stimulating cell growth may accompany the composite external implant. The implant is left in place as long as feasible, at least until regenerative cells can attach to the adjacent natural joint surface (usually in about 24 hours), or until wound healing (which may take up to 28 days or more depending on the joint structure). Preferably, the implant is designed stay within the joint structure for years, providing inert padding, cushioning and a new cell source. The implant may be used in weight bearing and non-weight bearing interfaces. Animal, such as in horses and dogs, can benefit from usage of the implant following hip and knee injuries. The implant is intended primarily for mammalian use. In humans, the implant may be used in any upper or lower extremity joint and temperomandibular joint.

These and other advantages of the invention will become more apparent from the following detailed description and the attached exemplary drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A depicts a side view of an embodiment of the knee implant curved about at least one condyle of a femur, the implant having appendages extending from an inflated balloon and showing the inflation medium moved anteriorly toward the patella when the knee joint is flexed. FIG. 10B depicts a side view of an embodiment of the knee implant curved about at least one condyle of a femur, the implant having appendages extending from an inflated balloon and having staples or screws or snaps or pins coupling the appendages to the femur and showing the inflation medium moved anteriorly toward the patella when the knee joint is flexed.

FIG. 11A depicts an embodiment of the unicompartment knee implant curved to simulate curvature about one condyle of a femur, the implant having appendages extending from an uninflated balloon (not shown) and including tabs and holes which may be used with couplers to couple the implant to the femur of the knee joint.

FIG. 11B depicts an embodiment of the unicompartment knee implant curved to simulate curvature about one condyle of a femur, the implant having appendages extending from an inflated balloon and including tabs and holes which may be used with couplers to couple the implant to the femur of the knee joint.

FIGS. 13A-13D depict multiple views of a staple adapted to couple an implant to a bone of the joint.

FIG. 14 depicts an embodiment of the knee implant having appendages including holes and tabs and including slots to accommodate ligaments of the knee joint as well as side views of the same knee implant.

DETAILED DESCRIPTION OF THE INVENTION

Figure 1:
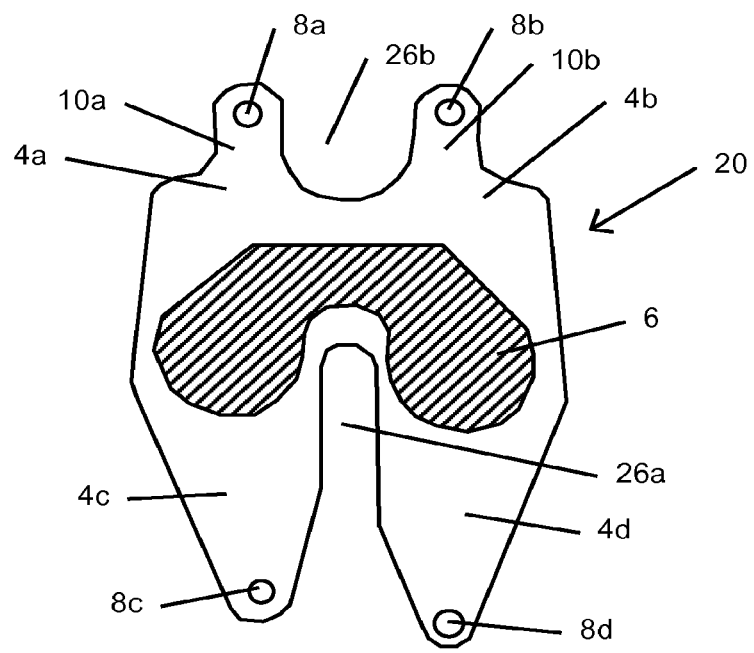
FIG. 1 depicts an embodiment of the knee implant having appendages including holes and tabs extending from a balloon and including slots to accommodate ligaments of the knee joint.

The present invention is directed to arthroplasty implants and procedures for a wide variety of joints such as, for example, hips, knees, shoulders, ankles, elbows, wrists, fingers, toes, temporomandibular joints and the like, but for clarity, as well as brevity, the discussion herein will focus on an implant for a knee joint or hip joint and an implant for replacing the talus bone of a patient's ankle.

Knee interpositional arthroplasty can replace existing total joint metal/plastic technology. It intends to fill the gap (literally in some embodiments of the implant) in cases where arthroscopic debridement fails to provide cure, since we can only 'polish arthritis' and 'clean up the joints' to date.

The polymer medically inflatable implants may physiologically restore joint function. Padding is provided where cartilage is damaged, cushioning to both the femoral tibial and patella femoral joints when narrowed or pathologic. The implant in some embodiments is adapted to deliver cells, autologous (from the patient), allograph (from another member of the same species) or xenograph (from another species,) that restore articular surfaces. Since cartilage is an immunologically privileged tissue, the antigens are buried in the cartilage matrix and antibodies do not reject the refurbished surface coating.

The gap (or gaps) filled by the balloon or balloons of the implant may provide compliance between opposing joint surfaces (the femoral condyle or condyles and tibial plateau). The femur may have some portion (of not all) of the retropatellar rounded facet "V" shape of hyaline, normally about 5 mm thick, or it may not have such hyaline when the implant is inserted. The tibial plateau may have some portion of meniscal fibrocartilages, including all of said fibrocartilages, none of said fibrocartilages, or some portion thereof. When the knee is extended (straight) the implant buffers the femoro-tibial joint. When the knee is flexed, the implant balloon apposition is more between the trochlear groove portion of the anterior distal femur (groove between the condyles on the 'front of the knee') and the patella.

The knee anatomy is unique to other joint anatomies and thus has a unique set of challenges that are addressed by the implant embodiments described herein. For example, the knee is not a ball and socket joint like a hip; it is a combination of two joints—the femoral-tibial joint and the patellar-femoral joint. The bones of the knee have facets and irregularities that must be accommodated by a conformable implant directed to the particular shapes of the bones without impeding the joints' functions and movements, and/or which minimizes impedance to such function and movement. Not only do the joints of the knee work together to allow extension and flexion of the knee, but the joints of the knee are also designed to allow rotational movement in a screw-like manner. That is, as the tibia is twisted relative to the femur, the joints are uniquely designed to allow this twist, but to limit the twist as well. Furthermore, the knee joints are able to withstand forces that vary depending on the particular movement of the individual, not only in force strength, but in direction as well. Thus, the implants as described herein are uniquely designed to account for these factors and result in a knee having preserved natural tissues as well as preserved function and movement as compared to typical arthroplasty procedures (such as partial or full knee replacements).

As described herein, embodiments of the implant conform to the patient's own joint features not only in that it can be pre-molded and/or adapted to couple to the contours of the patient's bone (condyle, etc), but in that it has a balloon having an inflation medium that is conformable to the joint anatomy and allow freedom of joint movement much like natural joint while preserving the joint and bone natural tissues as much as possible. With the ability to fill various chambers of the balloon with varying materials, and to add rigid and/or semi-rigid pieces to the implant, the implant can additionally have leveling capabilities and alignment capabilities.

Diagnoses:

Patients may complain of pain and knee joint dysfunction signaled by locking, clicking, or giving way. Knees may be swollen, malaligned or show crepitus (palpable crunching on movement.) Instability of ligaments whether anterior/posterior cruciates, or medial/lateral condyles, are treated by techniques separate for those entities via allowance for healing (as for collaterals) or via cruciate repair or reconstruction.

Indications for use of implants provided herein may be those patients recognizing greater than or equal to 2 Sq cm of 3–4+/4 traumatic arthritis (ala Carticel). In such cases, the cartilage defect is often precisely locally symptomatic, with point tenderness, clicking if a loose cartilage flap exists, and may be visible on MRI and/or arthroscopic inspection and/or through palpation. The implants used herein may additionally and/or alternatively be appropriate when existing techniques such as 'picking', K wire drills, and/or allograph implants fail.

Patients with knee problems typically complain of pain and dysfunction. Pathognomonic symptoms for meniscal tearing include locking, clicking, giving way from wear or twisting the knee. Aching diffusely may arise from arthritis or synovitis; anterior knee pain is generally patella-femoral, increased with stair use due to magnified body weight forces. Diagnosis should be accurate as distinguished from pain through the knee actually arising in the back caused by L4 nerve root irritation. Physical Exam findings of pathologic knees include observed swelling, redness, or deformity. Palpation often aids focus on which compartments are involved. The patella inhibition test position connotes retropatellar pathology, and often tracking problems that warrant soft tissue or boney correct. Improved limb alignment may increase benefits, and can in part accrue from selective inflation of embodiments of the implants provided herein. X-rays of the knee are best evaluated in weight bearing views, and should be coupled with other data including MRI or CT. Relative compartment narrowing suggests cartilage degradation. Once an embodiment of an implant described herein has been successfully implanted and the knee adequately rehabilitated, the appearance of a knee with such implant should resemble a normal joint X-ray. Knee distension is from saline and/or air insufflation. Knee implant patients will benefit from tailored rehab programs, cautious weight bearing, early motion, and potential the use of constant passive motion machine regimens.

General Features

Implant Aspects

Provided herein is a resilient implant for implantation into human or animal joints to act as a cushion allowing for renewed joint motion. The implant may endure variable joint forces and cyclic loads while reducing pain and improving function after injury or disease to repair, reconstruct, and regenerate joint integrity. The implant may be deployed in a prepared debrided joint space, secured to at least one of the joint bones and expanded in the space, molding to surrounding structures with sufficient stability to avoid extrusion or dislocation. The implant may have has opposing walls that move in varied directions, and an inner space filled with suitable filler to accommodate motions which mimic or approximate normal joint motion. The implant may pad the damaged joint surfaces, restores cushioning immediately and may be employed to restore cartilage to normal by delivering regenerative cells.

The implant may be have no inflation chamber (inner space). The implant may comprise a chamber which is not inflated once implanted. The implant may have varying thicknesses at different locations. The implant may have different features at different locations. Inflation may involve singular balloons for cushioning or realignment, multiple separate or connected vesicles, or small vacuoles that contain gas, fluid, gel, fluid that becomes solid, or combinations thereof. Inflation may be invoked on either both surfaces of the implant or any surface of the implant inside or between variable walls (which can be considered layers in certain embodiments). Cushioning while intending to address deficiencies in cartilage may accrue from inflation or the use of compliant materials without inflation (and without a balloon per se for that matter) or both.

Provided herein is a resilient interpositional arthroplasty implant for application into knee joints to pad cartilage defects, cushion joints, and replace or restore the articular surface, preserving joint integrity, reducing pain and improving function. The implant may endure variable knee joint compressive and shear forces, and millions of cyclic loads, after injury or disease requires intervention. The implant may repair, reconstruct, and regenerate knee joint anatomy in a minimally morbid fashion, with physiologic solutions that improve upon the rigid existing joint replacement alternatives of plastic and metal. In cases where cells have been used for joint resurfacing requiring massive periosteal harvesting for containment, the polymer walls of some embodiments of the implant can capture, distribute and hold living cells until aggregation and hyaline cartilage regrowth occurs. The implant may be deployed into a prepared debrided knee joint space, molding and conforming to surrounding structures with sufficient stability to avoid extrusion or dislocation. Appendages (or tabs) of the implant may serve to repair or reconstruct tendons or ligaments. The implant may have opposing walls that move in varied directions, and an inner space, singular or divided, filled with suitable gas, liquid, and/or complex polymer layers as force-absorbing mobile constituents, such than robust valid and reliable joint motion is enabled. There may be no defined inner chamber, however at a particular location in the device the implant may have different features to aid in cushion, therapeutic effect, wear resistance, defect correction, or the like.

Provided herein is a resilient orthopedic implant configured for deployment between a first bone and at least one second bone of a joint. In the case of a knee joint, the first bone may be a femur, a tibia, or a patella. In the case of a knee joint, the second bone may be a tibia, a patella or a femur. The implant may further comprise a balloon comprising a first portion that is configured to engage the first bone of the joint, a second portion that is configured to engage the second bone of the joint, a side portion connecting the first portion and the second portion, in which the side portion facilitates relative motion between the first portion and the second portion, and an interior that is optionally inflatable with a first inflation medium; and a first appendage configured to couple the balloon to the first bone of the joint. The terms "balloon" and "bladder" may be used interchangeably throughout this disclosure to describe an implant having the features described herein.

In some embodiments, at least two of the first portion, the second portion, and the side portion are contiguous. In some embodiments, the first portion comprises a first wall, the second portion comprises a second wall, and the side portion comprises a side wall. As used herein, each of the terms the "first portion", the "second portion", and the "side portion" is used to describe a part of the balloon, and may not be separate parts in some embodiments. In embodiments wherein no inflation is used, a first portion may be one side and the second portion another side of the same implant. In some embodiments, each portion or wall is named in order to indicate the general geometry and location of each portion relative to the other of the portions and/or relative to bones and/or ligaments and/or tendons of the joint. Likewise, as used herein, each of the terms the "first wall", the "second wall", and the "side wall" is used to describe a part of the balloon or cushioning implant, and may not be separate parts of the balloon in some embodiments. Rather, in some embodiments, each of the walls is named in order to indicate the general geometry and location of each portion relative to the other of the portions and/or relative to bones and/or ligaments and/or tendons of the joint. In some embodiments, at least two of first wall, the second wall, and the side wall are contiguous. Nevertheless, each of the walls may, in some embodiments, be separate parts of the implant that are joined to form the implant. Likewise, each of the portions may, indeed, in some embodiments, be separate parts of the implant that are joined to form the implant. In some embodiments, one wall may become the second wall with body movement changing the anatomy of the implant as it related to joint motion.

In some embodiments, the first portion is a term used interchangeably with the first wall. In some embodiments, the second portion is a term used interchangeably with the second wall. In some embodiments, the side portion is a term used interchangeably with the side wall. In some embodiments, a wall (whether a first wall, a second wall, and/or a side wall) of the implant may comprise a plurality of layers. The wall may comprise multiple materials to impart physical and/or therapeutic characteristics to the wall. In some embodiments, a side wall may become a first or second wall as the implant changes shape through the application of joint forces.

The distinction between the first wall and the second wall may merely be noted to show relative location, and may be a contiguous wall that has a first side (wall) and a second side (wall) where the first side is adapted to contact the first bone, and the second side is adapted to contact the second bone. The walls may be touching or be made of the same materials, or they may be made of different materials, or they may have additional materials therebetween, such as microstructures, vacuoles, therapeutic agents, padding materials, gels, liquids, solid materials, rigid or semi-rigid materials, meshes, foams, honeycombed materials, capsules, urethanes, human tissues or media, soft tissues, or the like, as described herein. Either of the walls themselves may be made of any of these materials and/or have any of these features. For example, a single sheet of BIONATE (e.g., BIONATE I, BIONATE II, BIONATE 55D, BIONATE 65D, BIONATE 75D, BIONATE 80, BIONATE 80A, BIONATE 90A) may be deemed to have a first wall that contacts the first bone, and second wall that contacts the second bone. In another example, a single sheet of Chronoflex (e.g., ChronoFlexAR®, ChronoFlex AL®, ChronoFlec C®) may be deemed to have a first wall that contacts the first bone, and second wall that contacts the second bone. Nevertheless, the single sheet may be contiguous, having no particular separation between the walls that may be deemed a chamber or balloon. Again, each of the first wall and the second wall may be, in certain embodiments, so designated only to depict relative location—i.e. in relation to the bone each wall is adapted to contact. The first wall may be so designated in order to indicate an intent that the first wall is in a position to contact the first bone, whereas the second wall may be so designated in order to indicate an intent that the second wall is in a position to contact the second bone, but the first wall and the second wall may be part of a contiguous implant, without any chamber or balloon therebetween.

The implant walls (first wall and/or second wall, and/or side wall may comprise a compliant material, and there may not be a separation between any of the walls of the implant which could be deemed a chamber. The material of the wall itself may be compliant such that the material itself accommodates cartilage irregularity and improved alignment of the joint bodies (ligaments, bones, tissue, etc.).

In some embodiments, the implant comprises a sheet. The sheet may be solid (e.g. comprising polyurethane or another biocompatible material), complex (e.g. comprising Dyneema mesh), or with at least one chamber of any size from a micrometer, to larger chambers as depicted and described elsewhere herein. The implant may comprise Dyneema mesh. The implant may comprise Dyneema fiber. In some instances, the implant comprises Dyneema Purity®. The implant may comprise a fiber. The implant may comprise a polyethylene fiber. The implant may comprise a mesh. The mesh may be a random structure or a repeating structure (such as a honeycomb). The mesh may comprise a polymer structure of interwoven or randomly interlinked fibers or a combination thereof. The mesh may comprise a metal structure of interwoven or randomly interlinked metal fibers or a combination thereof. The mesh may comprise a memory metal (e.g. Nitinol or another memory metal). The mesh may comprise a memory polymer. The mesh may aid in fixing the implant in place. The mesh may be adapted to add cushion to the bones of joint. The mesh may be adapted to add durability to implant upon cyclic loading. The mesh may be adapted to add padding to the bones of joint. The mesh may be filled in its interstices with a softer (in durometer) polymer or other material (softer than the material of the mesh itself). The mesh may be filled in its interstices with a softer (in durometer) polymer or other material (softer than the material of the mesh itself). The interstices of the mesh may comprise a pharmacologic or therapeutic agent (or both) as noted herein. The mesh may be filled with a harder material, or a material that becomes harder, such as methyl methacrylate. The mesh may comprise a biodegradable material. In some instances, the mesh does not comprise a biodegradable material. The mesh may comprise a steel wool. Alternatively, the mesh comprises DNA strands. In some embodiments, the mesh comprises intertwined DNA strands. In some embodiments, the mesh is configured to wrap a joint end.

In some embodiments there is no chamber in the implant. In such an embodiment, the implant may have a single composition throughout the implant, and shaped as noted herein with attachment features as noted herein. In such embodiments, distinction between the first wall and the second wall may be noted to indicate relative location, and may be a contiguous wall that has a first side (wall) and a second side (wall) where the first side is adapted to contact the first bone, and the second side is adapted to contact the second bone. In other embodiments of the implant, the implant comprises no chamber, however it comprises various regions which have different features than other regions—such as comprising a mesh between the first wall and the second wall (as noted above), a cushion between the first wall and the second wall, and/or comprising any aspects of the fill materials noted in the inflation mediums noted elsewhere herein, but not necessarily provided in a chamber which is filled following implantation or at the time of implantation. Rather, these aspects may be built into the implant during implant manufacture, by layering or other manufacturing processes, and not necessarily by filling a chamber. In some embodiments, there are multiple regions having different characteristics—cushioning, some therapeutic agent delivery, defect correction, padding, for non-limiting example, or some combination thereof. In some embodiments, the implant achieves these aspects by varying thickness of one of the walls at a particular region of the implant, for non-limiting example, at load-bearing locations. In some embodiments, the implant is inflatable having large chamber (in the 1-100 cm range), or small chamber (in the 1 micrometer to 1 cm range). In some embodiments, the implant may comprise such a chamber (or chambers) but not involve any inflation. In some embodiments, the implant may not have any inflatable chamber (or chambers) whatsoever. The range of inflation can be consistent with a continuum whereas implant spacing or vacuous interspace can vary at a molecular level as allowing for macromolecular sizes or macrodendritic molecules. The molecules covering the exposed or integral implant makeup may be constructed with coatings or without, that may be suspended in gas, liquid, gel, or solids with vacuoles, bubbles, balloons or bladders of a size producing a foam or trabecular framework or honeycomb that has 'inflation' not visually obvious. When encapsulating the cushioning gas or fluid in small containers, the cushioning effect may become more effective, and for a given amount of cushioning the intercell pressure can be reduced. The implant may comprise a foam between the first wall and the second wall. The implant may comprise a microvoid (i.e. a void in the implant material that is in the 1 micrometer to 1 mm size range). The implant may comprise first wall or second wall that may be prefabricated containing compressible material into which substances may be introduced via needle injection or cannula. The compressible material may be a gas or a foam mixed with a liquid. The implant may comprise first wall or second wall that may be prefabricated containing displaceable material into which substances may be introduced via needle injection or cannula. The displaceable material may be a gas or liquid.

In some embodiments, the implant comprises a selectively inflatable chamber that may pad a uniquely damaged and/or collapsed joint region, thus restoring both protective cushioning and adjacent limb alignment as that otherwise accomplished (for example via proximal tibial or distal femoral osteotomy in the case of a knee implant). A chamber or redundant membrane may, depending on the embodiment, not be inflated at all. In other embodiments, the chamber or redundant membrane may be maximally inflated so as to appear as a diffuse balloon appendage fastened to the otherwise capped and adherent polymer solid joint end wrapping. The singular macroscopic cells or inflated polymer segment make take on any shape conforming to the recipient site defect and/or the inflation depo may have a prefabricated shape planned to accommodate a certain amount of infusion whether as an extension into the knee joint as a flattened bladder mimically meniscal fibrocartilage or topping off a femoral head analogous to the external radius of a bipolar hip hemiarthroplasty. In either or any case the natural polymer pliability and ability to elastically deform may match the normal joint motions physiologically.

The implant may comprise materials without obvious or definable inflation of any sort, producing a cushioning effect usually over one primary joint surface but potentially over multiple, providing a useful cushioning via polymers of variable albeit solid material nature and reasoned compliance. In certain embodiments, the implant material per se and/or inflational enlargement immediately or gradually comes to conform to, accommodate, adjust and fill the indentations or defects on the side of implant in apposition to the defect. A semi-fluid tendency of certain embodiments permits both immediate post insertional and delayed joint surface alignment adjustments that may be increased by injection or cannular infusion, or deceased by aspiration or valvular evacuation.

In some embodiments, the filling material is an inflation medium. The first wall is secured to the end of the first bone by a skirt that extends from the first wall and the second wall engages the end surface of the second bone and may also be secured thereto. In some embodiments, the skirt 18 is called an appendage. The side wall extending between the first and second walls and defines at least in part the implant interior which is filled with filling material (or an inflation medium). The inner surfaces of wall and skirt preferably conform to the particular surface of the head of the patient's first bone. In some embodiments, the inner surfaces of wall and skirt preferably conform to the particular surface of the patient's first bone. The outer surface of the second wall is preferably configured to conform to the end surface of the second bone. In some embodiments, the outer surface of the second wall is preferably configured to conform to a surface of the second bone.

The edge of the implant may have a depending skirt to secure or anchor the implant to the end of bone, but may have one or more depending tabs (or appendages) that may be employed for similar functions as will be discussed in other embodiments. The skirt (and/or tabs, and/or appendages) may tightly fit about the end of the first bone as shown, or the skirt can be secured by adhesive (e.g. methyl methacrylate, bone in-growth) to the supporting bone structure or be mechanically connected by staples, screws and the like. Moreover, the lower portion of the skirt may be secured by a purse string suture or a suitable strand (elastic or tied) that is tightly bound about the outside of the skirt.

In some embodiments the implant comprises an in-growth patch on at least one of the first portion configured to engage the first bone, the second portion configured to engage the second bone, the side portion, and the appendage. The in-growth patch may be configured to encourage and/or promote tissue in-growth, such as bone in-growth, for non-limiting example. The patch may be as large as the portion itself (whether the first portion the second portion, the side portion, or the appendage) or may be smaller than the portion (such as in the shape of a strip or other shaped patch). The in-growth patch may comprise a surface irregularity or roughness. The in-growth patch may be Velcro-like. In some embodiments the implant comprises an in-growth patch on the first portion and/or the second portion, from (and in some embodiments including) a first appendage to a second appendage. In some embodiments, wherein the appendages loosen from attachment from the bone (by design and/or from wear and/or over time), the in-growth patch aids in securing the implant to the bone. In some embodiments, the in-growth patch comprises beads and/or bead-like elements attached to the implant. Such an in-growth patch may be configured to simulate trabecular bone space of a normally cancellous latticework. In some embodiments, the beads are sintered beads of various sizes. In some embodiments, the beads are sintered beads about 400 microns in size. With respect to bead size, the term "about" can mean ranges of 1%, 5%, 10%, 25%, or 50%. In some embodiments, the first bone and/or the second bone is roughened to acquire a bleeding bone to facilitate in-growth. In some embodiments, about 0.5 mm of cortical tissue is removed to facilitate in-growth.

In some embodiments, the appendage of the implant comprises a hook. In some embodiments the hook is angled. The hook may comprise a piece of metal sandwiched between two polymer pieces. The hook may comprise a piece of metal encased in polymer. In some embodiments, the hook may comprise a piece of metal and a portion of the metal piece may be encased in polymer. In some embodiments, the hook may comprise a piece of metal and a portion of the metal piece may be sandwiched between two polymer pieces. The metal of the hook may reinforce the appendage tabs for securing the implant to the bone of the joint. In some embodiments, the metal of the hook is formed of a 1 centimeter by 1 centimeter metal piece. The metal of the hook, or a portion thereof, may protrude from the appendage. The metal may be bent toward the bone to which it is configured to attach. The metal may be bent at about a 270 degree angle (as compared to the non-bent portion of the metal, or as compared to the rest of the appendage, for non-limiting example). The term about when referring to angle of bend of the metal of the hook can mean variations of 1%, 5%, 10%, 20%, and/or 25%, or variations of 1 degree, 5 degrees, 10 degrees, 15 degrees, 20 degrees, 25 degrees, 30 degrees, 40 degrees, 45 degrees, and/or up to 90 degrees. In some embodiments, the bone may be prepared to receive the hook, such as by a hole or slot into which the hook (or a portion thereof) is placed. In some embodiments, the bone is not prepared in advance to receive the hook, and the hook may self-seat into the bone by pressure applied to the hook into the bone. In some embodiments, the implant may comprise multiple appendages, and a plurality of the appendages has hooks. In some embodiment the implant may be screwed on or snapped on or secured with a combination of elements, such as stabilizers and sutures.

In some embodiments, the implant comprises a second appendage coupling the balloon to the first bone of the joint. In some embodiments, the implant comprises a second appendage coupling the balloon to at least one second bone of the joint. In some embodiments, the implant comprises a second appendage configured to couple at least one of the first portion, the second portion, and the side portion to at least one of the first bone and at least one second bone of the joint. In some embodiments, the first appendage and the second appendage are configured to provide ligamentary-like support to the first bone and the at least one second bone of the joint. In some embodiments, the first appendage and the second appendage are configured to provide ligamentary-like support to the joint. In some embodiments, the first appendage and the second appendage are configured to provide tendon-like support to the first bone and the at least one second bone of the joint. In some embodiments, the first appendage and the second appendage are configured to provide tendon-like support to the joint.

In some embodiments, the implant comprises an inflation port in communication with the interior of the balloon for inflation of the interior of the balloon with the first inflation medium. In some embodiments, the balloon is punctured to inflate the interior of the balloon with the first inflation medium. In some embodiments, the balloon is self-sealing. In some embodiments, the balloon is self-sealing upon inflation of the interior of the balloon with the first inflation medium. In some embodiments, the implant comprises a seal capable of closing the interior of the balloon. In some embodiments, a series or collection of balloons as bubble-wrap are adjacent to each other or in a series such that they share or distribute forces across joints or with weight bearing. In some embodiments the contents from one balloon may transfer to another balloon or the size of one balloon may change in relation to adjacent balloons as with shoes that contain air soled subject to roving forces.

The implant interior, if existing depending on the embodiment, between the walls and the wall may be filled with filler material (or an inflation medium) which aids in maintaining the desired implant dynamics within the joint structure. The nature of the filler material such as a fluid and the characteristics of the walls may be selected to maintain a desired spacing between the walls in order to accommodate the pressure applied by the bones of the joint structure to the implant and to allow suitable motion between the first and second walls of the implant which facilitate bone motion which mimics or approximates normal movement for the joint members involved. Alternatively, as mentioned above, the inner chamber may be filled with resilient material to provide the desired spacing, pressure accommodation, while allowing desired physiologic motion between implant layers. The implant is preferably configured to be shaped like the joint space and bone surfaces being replaced or to fill the void produced by injury or disease so that the natural joint spacing and cushioning of the joint interface is restored toward normal physiologic appearance and function. Fluids such as saline, mineral oil and the like may be employed to inflate the implant. In some embodiments, the inflated space can be maintained in the expanded position not by the contents (e.g. gas) but rather by the trabecular framework that props the walls apart, like cancellous bone fills the space between cortices with microscopic cavities that can be filled with various mediums. Such spaces may change with pathology such as bone with osteoporosis or lungs with emphysema. Therapeutic or physiologic filler that may be introduced into the implant, and transferred into the body through varied mechanisms, many of which are described elsewhere herein or would be known to one of skill in the art.

In some embodiments the implant may comprise vacuoles of pharmacologic substances. The vacuoles may be on a bone-engaging portion of the implant. In some embodiments, the implant comprises bubbles comprising an active substance such as a pharmacologic substance or other active substance. The implant may deliver by dissolution of the implant material (i.e. a biodegradable polymer which releases the active substance), and/or by release through pores of the implant (wherein the polymer is permeable to the active substance), and/or by fracture of the vacuole (or bubble, or space) by a catalyst such as ultrasound or pressure or other fracturing catalyst. The implant may deliver the active substance at a time after the actual implanting of the implant into the joint, for example an hour later, less than a day later, a day later, less than a week later, a week later, less than a month later, and/or a month later. In some embodiments, stem cells that are percolating in the bubble (or vacuole, or space) may be delivered to the joint space (or a constituent of the joint) after the implant is inserted into the joint. Active agents may, for non-limiting example, include cells (e.g., stem cells, differentiated cells, pluripotent cells, post-mitotic cells), growth factors, antibodies, biomolecules, biologics, chemical compounds, antibiotics, and/or viscolubricants. In some embodiments, the implant may comprise enzyme absorptive 'microscopic sponges' that could be sucked out or evacuated at or around the time of implant delivery to the joint.

In certain embodiments the implant (or a portion thereof, such as the balloon or balloons) is a weight bearing spacer that allows joint motions to approach normal, whether filling the space left by an entirely collapsed joint bone or the space of ablated cartilage proximate surfaces diffusely as in osteoarthritis or succinctly as in osteonecrotic defects or localized trauma. The walls of the implant may be used as a membrane for holding living cells in proximity of the osteochondral defect long enough for the cells to attach (e.g. 24 hours) or to deeply adhere (up to 28 days) or return to normal (up to one year). Weight bearing may be expected to increase as distal lower extremity joints are treated.

Figure 9A:
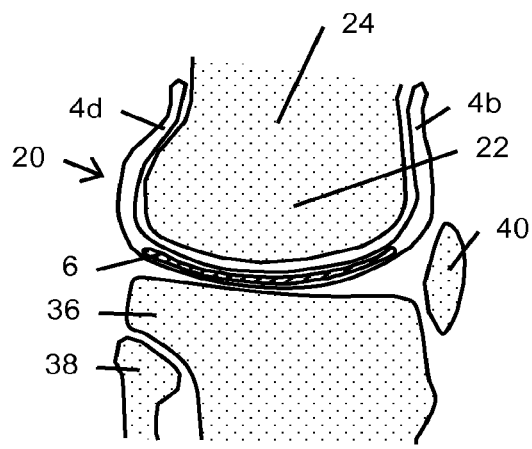
FIG. 9A depicts a side view of an embodiment of the knee implant curved about at least one condyle of a femur, the implant having appendages extending from an uninflated or minimally inflated balloon.
Figure 9B:
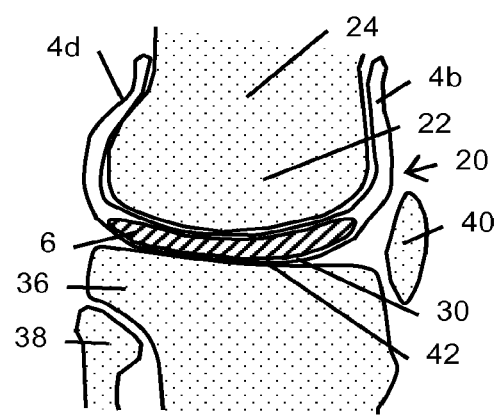
FIG. 9B depicts a side view of an embodiment of the knee implant curved about at least one condyle of a femur, the implant having appendages extending from an inflated balloon.
Figure 9C:
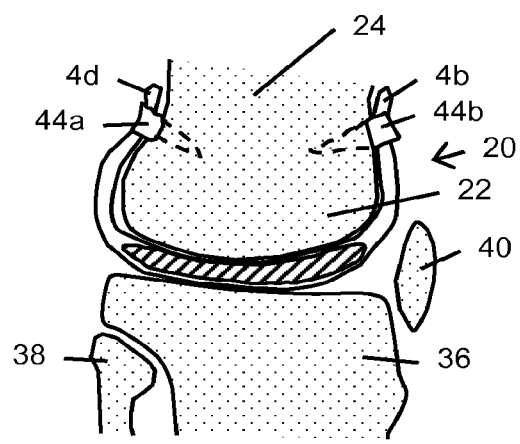
FIG. 9C depicts a side view of an embodiment of the knee implant curved about at least one condyle of a femur, the implant having appendages extending from an inflated balloon and having staples or screws coupling the appendages to the femur.

Movement (whether linear or curvilinear) between the first and second walls of the implant (i.e. of the balloon) as a result of movement of the femur and the tibia is illustrated in the comparison between FIGS. 9B and 10A, or in the comparison between FIGS. 9C and 10B. In some embodiments, the implant may comprise a balloon that is configured to allow a wall of the implant rolling upon another wall (or the same wall) of the implant (e.g. the side wall rolling upon the first wall, the first wall rolling upon the second wall, the second wall rolling upon the first wall, the first wall rolling upon the side wall, the second wall rolling upon the side wall, the side wall rolling upon the second wall, the first wall rolling upon the first wall, the second wall rolling upon the second wall, and/or the side wall rolling upon the side wall). In some embodiments, the implant may comprise a balloon that is configured to allow a portion of the implant rolling upon another portion (or the same portion) of the implant (for non-limiting example, the side wall rolling upon an appendage, the first wall rolling upon an appendage, and/or the second wall rolling upon an appendage). In some embodiments, the implant may comprise a balloon that is configured to allow movement of a portion of the implant rolling upon cartilage. While not shown in the drawings, there may be slippage between a portion of the implant (whether an appendage, a wall, or some other portion of the implant) and a joint component (whether a bone, ligament, tendon or other tissue). This slippage may be in addition to wall movements within the implant per se to provide desired joint movements. While not shown in the drawings, there may be slippage between the second bone (for example, the tibia) and the second wall in addition to wall movements within the implant per se to provide desired joint movements. The appendage (or appendages) is (are) designed to secure the implant to the joint structure so as to avoid dislocation of the implant. Movement of the joint with the implant in place may be a shared function of both the moving opposing walls of the implant but also a function of the movement of the wall which may be less attached to the joint members. There may be slight movement between the appendage, first wall and the first bone. The walls of the balloon may compress and/or stretch to accommodate bone interface movement. Material choices, material dimensions, and implant dimensions, placement and/or coupling may be chosen to allow for the desired amount of compression, stretching relative movement of various joint and/or implant components. For non-limiting example, the walls of the implant may be thicker is some areas to accommodate particular loads and the side wall may be thinner and more elastic to accommodate rolling and stretching thereof.

The interior of implant may be adjustably filled by the physician from an appropriate source thereof after the implant is deployed to ensure that the pathologic joint space becomes a resilient cushion again which aids restoration of worn or damaged cartilage interfaces in the joint by covering cartilage defects with the implant material, cushioning the joint and defects therein and delivering cell regeneration agents. In one embodiment, the arthroplasty implant comprises a bio-compatible inflatable member that is filled with a biocompatible fill material such as a gas, liquid, gel or slurry, or fluid that becomes a resilient solid to provide relative movement between the first and second walls. The filling or inflation media may be inserted through an injection valve site leading to the cannula which delivers the material into the interior of the implant. In an alternative embodiment, the implant may be filled with or have an interior formed of biologically compatible resilient material, e.g. a closed cell sponge filled with suitable fluid that is inserted into the interior of the implant prior to the implant's deployment or injected into the interior after the implant is deployed at the joint site. The interior of the implant may be provided with lubricious material to facilitate movement between the inner wall surfaces and to minimize contact wear therebetween. The polymeric walls of the implant may be impregnated with or otherwise carry tissue regeneration agents such as stem cells, living chondrocytes, and/or genes to repair joint surfaces.

Motion is believed to be primarily between the spaced walls (or portions) of the implant peripherally secured to joint structures, although some motion may occur between the implant and the joint surfaces. As shown in multiple Figures (including, FIGS. 1-7), the implant may be provided with a slot extending from the periphery of the implant toward the balloon of the implant to accommodate at least one ligament of the joint. Knee implants may have two slots leading to separate passages for receiving the anterior and posterior cruciate ligaments. Implant walls should have sufficient inherent flexibility to mold to the existing deformities imposed by either natural ligament, bone, tendon or remaining cartilage deformities of the internal joint space, and thus filled as a cushion. The wall exteriors may be flat or formed with random or specific patterns for purposes of glide or trends for traction against adjacent surfaces, or as sulci or venues for cell delivery materials.

The exterior of the implant may have a mesh material with a plurality of chords (or appendages) for securing the implant to adjacent bones or to remnant ligaments which are attached to adjacent bones. The exterior of the implant may comprise Dyneema mesh. The exterior of the implant may comprise Dyneema fiber. In some instances, the exterior of the implant comprises Dyneema Purity®. The exterior of the implant may comprise a fiber. The exterior of the implant may comprise a polyethylene fiber.

The dimensions of the various implant walls may vary depending upon the material properties thereof as well as the needs for a particular joint. Additionally, the first and second walls may require a thickness different from the side wall. Generally, the implant may have a wall thicknesses of about 0.125 mm to about 3 mm, preferably about 0.5 mm to about 1.5 mm. The spacing between the first and second wall within the interior can vary from about 0.5 mm to about 5 mm. Thicknesses of the fixation tabs may be at least one of: about 1 mm, about 2 mm, about 3 mm, about 4 mm, about 5 mm, about 6 mm, about 7 mm, about 1 mm to about 6 mm, about 2 mm to about 4 mm, 1 mm to 6 mm, and 2 mm to 4 mm, for non-limiting example. The implant may comprise a reinforcing rim or a reinforced tab, which includes a change in tab material to make it stronger, or include a metal rim to reinforce the attachment location. The reinforcement element may be embedded in the tab or in a wall at the periphery of the implant (for example in instances where the coupler is not located at a tab per se).

Figure 11C:
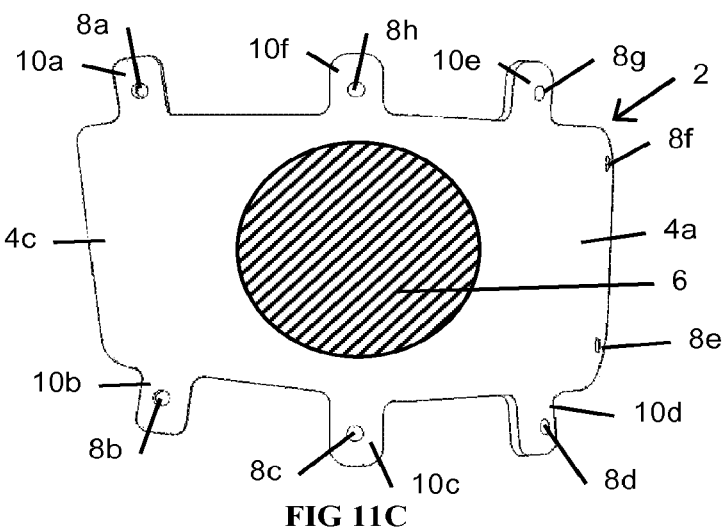
FIG. 11C depicts a bottom-up view of an embodiment of the unicompartment knee implant curved to simulate curvature about one condyle of a femur, the implant having appendages extending from an inflated balloon and including tabs and holes which may be used with couplers to couple the implant to the femur of the knee joint.
Figure 12A:
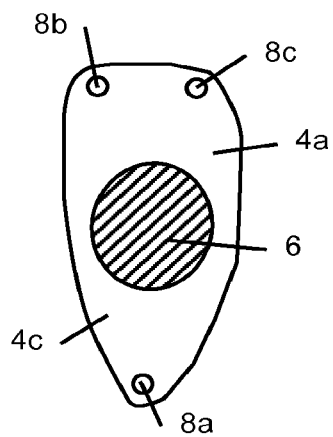
FIG. 12A depicts a bottom-up view of an embodiment of the unicompartment knee implant or patch implant, the implant having appendages, extending from a balloon and including holes, which may be used with couplers (not shown) to couple the implant to the femur of the knee joint.
Figure 12B:
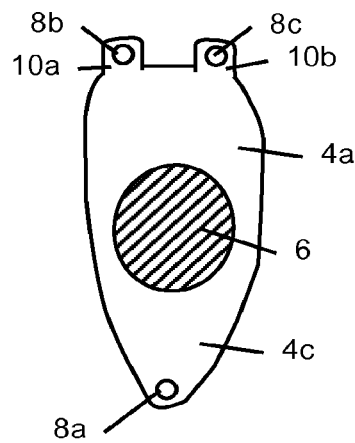
FIG. 12B depicts a bottom-up view of an embodiment of the unicompartment knee implant or patch implant, the implant having appendages, extending from a balloon and including tabs and a hole which may be used with couplers (not shown) to couple the implant to the femur of the knee joint.
Figure 12C:
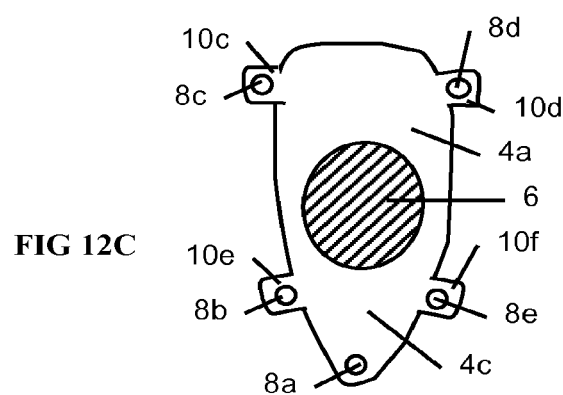
FIG. 12C depicts a bottom-up view of an embodiment of the unicompartment knee implant or patch implant, the implant having appendages, extending from a balloon and including tabs and a hole which may be used with couplers (not shown) to couple the implant to the femur of the knee joint.

In some embodiments, the implant has a first wall, a second wall, and a side wall which define the implant interior (or exterior) which contains filling material. In some embodiments, the filling material is an inflation medium. The first wall is secured to the end of the femur by at least one appendage that extends from the first wall and the second wall engages the end surface of the second bone (which in the case of a femoral-tibial joint implant, would be the tibia) and may also be secured thereto. The side wall extending between the first and second walls defines at least in part the implant interior which is filled with filling material (or an inflation medium). The inner surfaces of wall and appendage may conform to the particular surface femur, for example by being wider in particular locations and/or longer in particular areas. For example a dual compartment implant (described herein) may have a wider section to cover the medial condyle than the lateral condyle (as shown in FIGS. 1, 2, 3, 6A, 6B, and 7). In another example, the length of the implant the along the external edge may be longer than the length of the implant along the trochlear groove edge (as shown in FIGS. 11A, 11B and 11C). In yet another example, the width may vary along a single condyle, such as is shown in FIGS. 12A-12C, wherein the wider edge of the implant is adapted to fit over at least a portion of the anterior condyle, and the narrower portion is adapted to fit over at least a portion of the posterior condyle. In some embodiments, the inner surfaces of the first wall and appendages preferably conform to the particular surface of the patient's femur, and do so by not only dimensions of the implant (lengths, widths, balloon location and shape), but also and/or alternatively due to appendage and/or tab and/or hole and/or coupler location and/or surface contours of the first wall. The outer surface of the second wall may be configured to conform to the end surface of the second bone (which may be a tibia or a patella, for example). In some embodiments, the outer surface of the second wall is configured to conform to a surface of the second bone (which may be a tibia or a patella, for example). The figures provided herein are highly schematic and do not depict details of the joint surface features, since human pathology and variation reflects both the patient's immediate and evolving pathophysiology. Neither do the figures depict other joint features such as cartilage, tendons, ligaments and other soft tissues and fluids of the joint for ease of viewing that which is depicted.

In some embodiments, the implant is configured to resemble the shape of the natural hyaline of a normal knee. For example, the normal hyaline is typically "H" shaped, thus certain embodiments of the implant are generally "H" shaped. The H may be an exaggerated H form, and the notches of the H may be extended on one side, while nearly nonexistent on the other side, such as is shown in certain figures, such the "H" may look more like a "U" or "V" or contain a tab in the notch. For each joint the cartilage surface shapes, implant design, and method of surgery can vary by adapting to normal anatomy in a particular patient, to expected weight bearing, and use intent.

Implant Materials and Material Features

In some embodiments, the implant comprises polymer. Polymers may comprise at least one of: a polyurethane (such as, for example, ChronoFlex AR, ChronoFlex AL®, ChronoFlec C®), a polycarbonate urethane, a thermoplastic polycarbonate urethane (such as BIONATE, e.g., BIONATE I, BIONATE II, BIONATE 55D, BIONATE 65D, BIONATE 75D, BIONATE 80A, BIONATE 90A, BIONATE 55 or BIONATE 80), ethylene-vinyl acetate copolymer, multi-block copolymers of poly(ethylene oxide) (PEO) and poly (butylene terephthalate) (PBT), PEG, PEO, and a polyetheylene. In some embodiments the implant comprises a 125 micron thickness thermoplastic polycarbonate urethane. In some embodiments, the thermoplastic polycarbonate urethane has a low coefficient of friction. In other embodiments, the thickness of walls intends to mimic natural hyaline cartilage a the involved body location and may be one of: about 0.5 mm, about 1 mm, about 2 mm, about 2.5 mm, about 3 mm, about 3.5 mm, about 4 mm, 0.5 mm, 1 mm, 2 mm, 2.5 mm, 3 mm, 3.5 mm, 4 mm, 1 mm-6 mm, 1 mm-4 mm, and 1 mm-3 mm.

The implant may comprise to a plurality of layers of polymer (such as ChronoFlex AR, ChronoFlexAR®, ChronoFlex AL®), ChronoFlec C®) in a solvent and evaporating the solvent after applying each layer. In some embodiments, the implant comprises a polyurethane that is sprayed and dried (wherein the spraying and drying is repeated at least once) to a desired thickness.

In some embodiments, the implant is created by dip molding a mandrel having a shape of a bone of the knee joint (the medial condyle, the lateral condyle, the tibia, for non-limiting example) into a polymer solution (for non-limiting example, a urethane polymer such as Chronoflex (e.g., ChronoFlexAR®, ChronoFlex AL®), ChronoFlec C®)). Following each dip, the implant is dried for a specified time, which may be, for example, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 45 seconds, about 1 minute, about 2 minutes, about 5 minutes, about 10 minutes, about 15 minutes, and over about 15 minutes. The term "about" used herein in reference to drying time of the implant can mean variations of at least one of 5%, 10%, 25%, and 50%, In some embodiments, no drying step is used. The dipping may be repeated multiple times. In some embodiments a single dip is sufficient. In some embodiments, the dipping is repeated 2 times. In some embodiments, the dipping is repeated 3 times. In some embodiments, the dipping is repeated 4 times. In some embodiments, the dipping is repeated 5 times. In some embodiments, the dipping is repeated 6 times. In some embodiments, the dipping is repeated 7 times. In some embodiments, the dipping is repeated 8 times. In some embodiments, the dipping is repeated 9 times. In some embodiments, the dipping is repeated 10 times. In some embodiments, the dipping is repeated 11 times. In some embodiments, the dipping is repeated 12 times. In some embodiments, the dipping is repeated 13 times. In some embodiments, the dipping is repeated 14 times. In some embodiments, the dipping is repeated 15 times. In some embodiments, the dipping is repeated 16 times. In some embodiments, the dipping is repeated 17 times. In some embodiments, the dipping is repeated 18 times. In some embodiments, the dipping is repeated 19 times. In some embodiments, the dipping is repeated 20 times. In some embodiments, the dipping is repeated 21 times. In some embodiments, the dipping is repeated 22 times. In some embodiments, the dipping is repeated 23 times. In some embodiments, the dipping is repeated 24 times. In some embodiments, the dipping is repeated 25 times. In some embodiments, the dipping is repeated over 25 times. In some embodiments, the dipping is repeated a sufficient number of times to create an implant that is a prescribed thickness. The thickness may vary depending on the polymer and depending on the embodiment of the implant. The thickness may be at least one of: about 25 microns thick, about 50 microns thick, about 100 microns thick, about 125 microns thick, about 150 microns thick, about 200 microns thick, about 250 microns thick, about 300 microns thick, about 350 microns thick, about 400 microns thick, about 25-50 microns thick, about 50-100 microns thick, about 50-200 microns thick, about 100-150 microns thick, about 150-300 microns thick, about 100-300 microns thick, about 100-500 microns thick, about 200-500 microns thick, and about 200-1000 microns thick. The term "about" used herein in reference to thickness of the implant can mean variations of at least one of 5%, 10%, 25%, and 50%, The thickness may vary at different locations of the implant. In some embodiments, the implant is fabricated in two pieces, one or more of which is molded to form an interior when the two pieces are put together. In some embodiments, the implant is filled by puncturing the implant wall and sealing the puncture hole with a plug, patch or other sealant. The plug, patch, or other sealant may comprise Chronoflex material (e.g., ChronoFlexAR®, ChronoFlex AL®, ChronoFlec C®), for non-limiting example. The plug, patch, or other sealant may comprise the same material from which the implant is constructed, for non-limiting example. In some embodiments, the implant thickness may be many millimeters, for example, where larger defects or malignments are being corrected.

The walls of the implant embodying features of the invention may be composite structures. For example, the innermost layer may be impervious to preclude escape of inflation or other filling media, a central layer may be porous or otherwise contain treatment or cell regeneration agents, and the outer layer may be a thin, but strong layer of a thermoplastic, such as a thermoplastic polyurethane for non-limiting example, which has microporosity sufficient to allow passage or egress of treatment or cell regeneration agents from the central layer (or second layer). The degree of microporosity to enable egress of treatment or cell regeneration agents from the central layer is found in polymer layers such as Chronoflex (e.g., ChronoFlexAR®, ChronoFlex AL®, ChronoFlec C®) or BIONATE (e.g., BIONATE I, BIONATE II, BIONATE 55D, BIONATE 65D, BIONATE 75D, BIONATE 80A, BIONATE 90A, BIONATE 55 or BIONATE 80).

The external wall (and/or the bone engaging surface) of the implant may be coated and/or impregnated with a latticework of polymer that is surface sprayed or layered on the outside (or bone engaging surface) of the implant to promote cartilage tissue regeneration. This most external surface coating may contain living chondrocytes (for example, as is provided in the Carticel procedure by the Genzyme company), and/or may contain stem cells with directed gene mutations to enhance adherence of the coating to the implant. Chondrocytes from companies such as Tygenix or Histogenics may be used for greater aggregation potential. The bone engaging surface may comprise peaks and troughs. The living cells may be imposed in between (and/or provided in the) troughs of the implant surface while the surface areas of prominence (the peaks of the surface) may be used for at least one of: space validation, traction, and cell protection.

The implant may be formed of suitable bioabsorbable materials so that the implant may be absorbed within a particular predetermined time frame. Suitable bioabsorbable materials include polylactic acid, polyglycolic acid, polycaprolactone, copolymers, blends and variants thereof. Suitable bioabsorbable materials may also/alternatively include poly(hydroxyalkanoate)s of the PHB-PHV class, additional poly(ester)s, and natural polymers, particularly, modified poly(saccharide)s, e.g., starch, cellulose, and chitosan. The walls of the implant may be (in whole and/or in part) bioabsorbable. The balloon may be (in whole and/or in part) bioabsorbable. As used herein the terms bioabsorbable, bioerodable, and/or bioabsorbable may be used interchangeably. The walls of the implant may release a pharmaceutical agent or an biological agent (such as stem cells, differentiated cells, pluripotent cells, post-mitotic cells, living chondrocytes, gene therapies, and the like). The release of such agents (whether biological or pharmaceutical, or a combination thereof) may occur over time, as the wall of the implant (or as the balloon) bioabsorbs in some embodiments, or as the joint is used (i.e. through pressure, for non-limiting example). In some embodiments, at least one of the implant walls is permeable to a pharmaceutical agent and/or a biological agent, such as in an embodiment wherein the inflation medium comprises the pharmaceutical agent and/or biological agent. In some embodiments, at least one of the implant walls has pores through which the pharmaceutical agent and/or the biological agent may fit, such as in an embodiment wherein the inflation medium comprises the pharmaceutical agent and/or biological agent. In some embodiments the contents may contain targeting drugs such as gleevac that turn off tumor molecules as those in GIST. Cell-specific drugs targeting tumors by design may require nano-sized micelles with hydrophilic shells to protect core agents. In some embodiment hydrogels are used and tailored to swell thus releasing trapped molecules or cells through weblike surfaces, controlled by internal or external triggers such as ph, magnetic fields, or temperature. Dendritic macromolecules may be used in implants to deliver agents en masse deploying a controllable size and structure. In some embodiments, individual agent molecules or hubs may be incorporated via covalent bonds.

In some embodiments, the interior comprises a plurality of inflatable chambers. In some embodiments, the interior comprises a plurality of individually inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium. The implant may be provided with latticework or other reinforcing strands, preferably on the exterior or within the wall thereof to control the maximum expansion of the implant when deployed at the orthopedic site.

In some embodiments, the implant comprises amniotic membrane (and/or a component thereof). In some embodiments, the implant comprises amniotic sac (and/or a component thereof). In some embodiments, the implant comprises amniotic tissue (and/or a component thereof). Amniotic membrane (and/or sac and/or tissue) is unique in that its mechanical properties include that it slippery on one side (lubricious, low modulus of elasticity) and sticky (adherent) on the other. In some embodiments, at least one of the first wall, the second wall and the side wall comprise amniotic membrane or a component thereof. In some embodiments, at least one of the first wall, the second wall and the side wall comprise amniotic sac or a component thereof. In some embodiments, at least one of the first wall, the second wall and the side wall comprise amniotic tissue or a component thereof. The amniotic membrane and/or amniotic sac and/or amniotic tissue may be used in conjunction with other biologic agents, pharmaceutical agents, and/or therapeutic agents. Amniotic tissue is used extensively in pleuripotential cells. It qualifies as HTBP (Human Tissue Based Product) because of the short term time span on the product and origin.

In some embodiments, the balloon is a composite structure. In some embodiments, the balloon comprises layers of porous and/or non-porous materials, or otherwise contain treatment or cell regeneration agents. In some embodiments, a first layer of the balloon is a thin, but strong layer of a thermoplastic, such as a thermoplastic polyurethane, for non-limiting example, which has microporosity sufficient to allow passage or egress of treatment or cell regeneration agents from a second layer. The second layer may be a central layer (which lies between the first layer and a third layer or a fourth layer or more layers). The first layer may comprise a bone engaging surface in some embodiments. The degree of microporosity to enable egress of treatment or cell regeneration agents from the second layer is found in polymer layers such as Chronoflex (e.g., ChronoFlexAR®, ChronoFlex AL®, ChronoFlec C®) or BIONATE (e.g., BIONATE I, BIONATE II, BIONATE 55D, BIONATE 65D, BIONATE 75D, BIONATE 80A, BIONATE 90A, BIONATE 55 or BIONATE 80). The bone engaging surface of the implant may be coated and/or impregnated with a latticework of polymer that is surface sprayed or layered on the bone engaging surface of the implant to promote cartilage tissue regeneration. This bone engaging surface coating may contain living chondrocytes (for example, as is provided in the Carticel procedure by the Genzyme company), and/or may contain stem cells with directed gene mutations to enhance adherence of the coating to the implant. The bone engaging surface may comprise peaks and troughs. The living cells may be provided in troughs while the surface peaks may be used for at least one of: space validation, traction, and cell protection.

In some embodiments, the implant is pre-molded to fit about at least one condyle of the femur. In some embodiments, the implant comprises a memory plastic. In some embodiments, the implant comprises a wire frame. In some embodiments, the wire of the wire frame comprises a memory metal. In some embodiments, the memory metal comprises nitinol. In some embodiments, the wire frame is disposed in the periphery of the implant or a portion thereof. In some embodiments, the wire frame is configured to aid in placement against the posterior of the condyle.

In some embodiments, at least a portion of the implant comprises a slippery surface. In some embodiments the slippery surface is configured to allow for relative movement between the implant (or a portion thereof) that is coupled to the femur and the tibia. In some embodiments the slippery surface is configured to allow for relative movement between the implant (or a portion thereof) that is coupled to the femur and the patella.

In some embodiments, the implant comprises a sheet. The sheet may be solid (e.g. comprising polyurethane or another biocompatible material), complex (e.g. comprising Dyneema mesh), or with at least one chamber of any size from a micrometer, to larger chambers as depicted and described elsewhere herein. The implant may comprise Dyneema mesh. The implant may comprise Dyneema fiber. In some instances, the implant comprises Dyneema Purity®. The implant may comprise a fiber. The implant may comprise a polyethylene fiber. The implant may comprise a mesh. The mesh may be a random structure or a repeating structure (such as a honeycomb). The mesh may comprise a polymer structure of interwoven or randomly interlinked fibers or a combination thereof. The mesh may comprise a metal structure of interwoven or randomly interlinked metal fibers or a combination thereof. The mesh may comprise a memory metal (e.g. Nitinol or another memory metal). The mesh may comprise a memory polymer. The mesh may aid in fixing the implant in place. The mesh may be adapted to add cushion to the bones of joint. The mesh may be adapted to add durability to implant upon cyclic loading. The mesh may be adapted to add padding to the bones of joint. The mesh may be filled in its interstices with a softer (in durometer) polymer or other material (softer than the material of the mesh itself). The mesh may be filled in its interstices with a softer (in durometer) polymer or other material (softer than the material of the mesh itself). The interstices of the mesh may comprise a pharmacologic or therapeutic agent (or both) as noted herein.

To be clear, in some embodiments, there is no chamber in the implant. In such an embodiment, the implant may have a single composition throughout the implant, and shaped as noted herein with attachment features as noted herein. In other embodiments of the implant, the implant comprises no chamber, however it comprises various regions which have different features than other regions—such as comprising a mesh between the first wall and the second wall (as noted above), a cushion between the first wall and the second wall, and/or comprising any aspects of the fill materials noted in the inflation mediums noted elsewhere herein, but not necessarily provided in a chamber which is filled following implantation or at the time of implantation. Rather, these aspects may be built into the implant during implant manufacture, by layering or other manufacturing processes, and not necessarily by filling a chamber. In some embodiments, there are multiple regions having different characteristics—cushioning, some therapeutic agent delivery, defect correction, padding, for non-limiting example, or some combination thereof. In some embodiments, the implant achieves these aspects by varying thickness of one of the walls at a particular region of the implant, for non-limiting example, at load-bearing locations.

Inflation Medium and Inflation or Filling of the Implant Interior

In some embodiments, the implant comprises an inflation medium that is compressible. In some embodiments, the implant comprises an inflation medium that comprises a viscolubricant. In some embodiments, the implant comprises an inflation medium that comprises a pharmacologic substance. In some embodiments, the implant comprises an inflation medium that comprises an NSAID. In some embodiments, the implant comprises an inflation medium that comprises chondrocytes. In some embodiments, the implant comprises an inflation medium that comprises cells (e.g., stem cells, differentiated cells, pluripotent cells, postmitotic cells). In some embodiments the implant is configured to anneal the outer most layer of the implant (or a portion thereof) to the peripheral of succinct cartilage defects so as to cover them, allowing for healing. In some embodiments the implant is configured to anneal the outer most layer of the implant (or a portion thereof) to the peripheral of succinct cartilage defects so as to cover them, allowing for healing once new chondrocytes have been installed.

The implant interior (balloon interior) may be inflated with gas. The implant interior (balloon interior) may be inflated with liquid. The implant interior (balloon interior) may be inflated with saline. The implant interior (balloon interior) may be inflated with suspended stem cells. The implant interior (balloon interior) may be inflated with gel. The implant interior (balloon interior) may be inflated with a viscolubricant. The inflation medium in some embodiments stays within the balloon, or a portion thereof (as where there are multiple chambers to the balloon). In some embodiments, balloon contents disburse through microporosities and/or dissolving membranes into the joint. In some embodiments, balloon contents disburse by expulsive or evacuation precipitated through an implant wall after pressure from limb use. In some embodiments, balloon contents disburse by expulsive or evacuation precipitated through an implant wall from planned osmosis. In some embodiments, balloon contents disburse by expulsive or evacuation precipitated through an implant wall from vacuole rupture (whether mechanical rupture, ultrasound, or chemical rupture, for non-limiting example). In some embodiments, balloon contents disburse by expulsive or evacuation precipitated through an implant wall thereby distributing contents of the implant interior to joints as lubricious, analgesic, anti-inflammatory and/or otherwise healing substances. In some embodiments, the implant may comprise solid beads or beads containing gel or liquid for sequential disbursement by compressive force through rupture with varied bead wall thicknesses, or the beads may be time-released (opened) chemically, pharmacologically, or by an outside ultrasound or magnetic force external knee application at appropriate clinical intervals. In some embodiments, the implant may comprise vacuoles containing gel or liquid for sequential disbursement by compressive force through rupture with varied vacuole wall thicknesses, or the vacuoles may be time-released (opened) chemically, pharmacologically, or by an outside ultrasound or magnetic force external knee application at appropriate clinical intervals. The implant material may be foam or complaint material (such as a compliant polymer).

The implant interior (or balloon interior) between the first wall and the second wall is filled with filler material (or an inflation medium) which aids in maintaining the desired implant dynamics within the joint structure. The nature of the filler material such as a fluid and the characteristics of the walls may be selected to maintain a desired spacing between the walls in order to accommodate the pressure applied by the bones of the joint structure to the implant and to allow suitable motion between the first and second walls of the implant which facilitate bone motion which mimics or approximates normal movement for the joint members involved.

Alternatively (and/or additionally), the inner chamber (interior or a portion thereof) may be filled with resilient material to provide the desired spacing, pressure accommodation, while allowing desired physiologic motion between implant layers. The implant may be configured to be shaped like the joint space and bone surfaces being replaced or to fill the void produced by injury or disease so that the natural joint spacing and cushioning of the joint interface is restored toward normal physiologic appearance and function. The interior of implant is adjustably filled by the physician from an appropriate source thereof after the implant is deployed to ensure that the pathologic joint space becomes a resilient cushion again which aids restoration of worn or damaged cartilage interfaces in the joint by covering cartilage defects with the implant material, cushioning the joint and defects therein and delivering cell regeneration agents. In one embodiment, the implant comprises a bio-compatible inflatable member (balloon) that is filled with a biocompatible fill material (inflation medium) such as a gas, liquid, gel or slurry, or fluid that becomes a resilient solid to provide relative movement between the first and second walls.

In some embodiments, the features of the implant change over time. For example, prior to, at, or during implantation, the implant may comprise a powder methyl methacrylate and a liquid that becomes a slurry upon insertion or soon thereafter, and that once implanted hardens (or cures) within the implant. The methyl methacrylate (e.g. as a powder) and a catalyst liquid together become solid and are an example of a cement (or bone cement), however other cements or other materials which cure over time or with heat or with loading or by other methods (chemical or physical) are contemplated as alternatives. In certain embodiments, at least one of the powder methyl methacrylate and the liquid is part of the implant at the time of implantation. In certain embodiments, at least one of the powder methyl methacrylate and the liquid is injected into or loaded into the implant at the time of implantation or soon thereafter. In certain embodiments, both the powder methyl methacrylate and the liquid are injected into or loaded into the implant at the time of implantation or soon thereafter. In certain embodiments, at least one of the powder methyl methacrylate and the liquid is a fill material. In certain embodiments, the implant does not have a chamber prior to injection of (or loading of) a fill material between the first wall and the second wall. The injection (or loading) of a fill material between the first wall and the second wall creates a chamber. In certain embodiments, the implant comprises interstices which are occupied by the fill material. In some embodiments, the methyl methacrylate powder and liquid catalyst are already inside the implant but only mix after intentional deployment in external or internal manners.

In some embodiments, the first inflation medium imparts rigidity in the implant. In some embodiments, the first inflation medium imparts cushion in the implant. In some embodiments, the inflation medium chosen for the first inflation medium, and/or the particular choice of chamber (in embodiments having multiple chambers) filled with such first inflation medium aligns the joint. In some embodiments, the inflation medium chosen for the first inflation medium, and/or the particular choice of chamber (in embodiments having multiple chambers) filled with such first inflation medium aligns the bones of the joint. In some embodiments, the inflation medium chosen for the first inflation medium, and/or the particular choice of chamber (in embodiments having multiple chambers) filled with such first inflation medium changes the bone alignment. In some embodiments, the inflation medium chosen for the first inflation medium, and/or the particular choice of chamber (in embodiments having multiple chambers) filled with such first inflation medium improves joint alignment. In some embodiments, the inflation medium chosen for the first inflation medium, and/or the particular choice of chamber (in embodiments having multiple chambers) filled with such first inflation medium restores, at least in part, joint alignment. In some embodiments, individual chambers of the interior may be selectively inflated with a first inflation medium and/or a second inflation medium. In some embodiments, individual chambers of the interior are selectively inflated with a first inflation medium and/or a second inflation medium in order to reconstruct the joint and/or bones of the joint.

In some embodiments the inflation medium comprises living chondrocytes.

The implant interior (balloon interior) may be inflated with methyl methacrylate as a liquid that becomes a solid or semi-solid (rigid or semi-rigid). In some embodiments, the inflation medium is a methyl methacrylate or other biocompatible hardening substance which can flow when initially put into the chamber, and hardens to become a rigid piece or semi-rigid piece or solid piece. The methyl methacrylate or other biocompatible hardening substance may conform to the shape of the chamber, or may conform to the shape of a space between bones and/or other joint structures. The methyl methacrylate or other biocompatible hardening substance may conform to a form chosen by the surgeon using tools and/or pressure to influence the final shape of the rigid piece formed by the methyl methacrylate or other biocompatible hardening substance upon hardening.

The side wall extends between the first and second walls to form an interior which receives filling material through tube (also called a conduit herein, or may be called an inflation port). In some embodiments, the inflation port is not a tube, but is a valve which may or may not extend from a wall of the implant. The valve may be part of a wall of the implant, or part of the balloon or a portion thereof. The implant would also be appropriate for one condyle of the knee, but other shapes may be desired for other joint configurations whether relatively flat or more inflated toward a ballooning construct. In some embodiments, the inner diameter of the inflation port (or tube) is 5 millimeters maximum. In some embodiments, the inner diameter of the inflation port is about 1 millimeter. In some embodiments, the inner diameter of the inflation port is about 2 millimeters. In some embodiments, a needle (of typical needle sizes) may be used to inflate the implant.

A separate portal or tube (not shown) or the existing conduit (tube or valve), may be used to extract noxious inflammatory enzymes that can be aspirated at appropriate clinical intervals. Inflammatory enzymes in the COX1, COX2 and or 5LOX pathways can be extracted. Viscolubricants can be injected into the interior of the resilient arthroplasty implant through existing conduit or through a long needle to aide in distension, expansion, lubrication (with predetermined microporosity).

In some embodiments, an inflation medium that generates heat (by means of a catalyst reaction or other means) may be used to deliver heat to a joint structure. The heat may aide hyaline cartilage annealing. Thermal effects of the implant materials are calculated accordingly to benefit and protect the joint surface analogous to a dry suit or wet suit for a scuba diver exposed to temperature extremes. Embodiments of the implant generally seek to avoid head from friction via lubricious coatings whether allograph as amniotic membrane or polymer, for non-limiting example.

The implant in some embodiments is inserted arthroscopically through a cannula about 10 mm in diameter with the implant in the deflated construct, and once inside the prepared joint space and secured therein by the appendages or tabs, the implant may be distended or inflated with gas, gel, fluid or fluid that becomes a resilient solid to fill the original natural space of a bone of the joint (whether the tibia, femur or patella). Tensioning may be by the surgeon's sense of proper pressure application aided by a gauged syringe for insertion of viscolubricants such as Synvisc, Hyalgan, Supartz and/or analgesics such as lidocaine gel. The insertion of liquids to the joint per se may be directly, through a cannula to the joint space previously in place for debridement, and or via a cannula or tube that is not part of the original implant assembly. Once the joint is cleaned, the implant is inserted and appropriately fixed to avoid extrusion or dislocation thereof. This may be via attachment of the implant tabs and/or by a combination of tab use plus intended friction created by implant surface coverings (analogous to Velcro) or a draw string at the smaller base of the implant.

In some embodiments, the implant comprises a coil (spring). The coil, or multiple coils, may be secured inside the implant. In some embodiments, the materials of the implant secure the coil or coils within the implant. In some embodiments, the implant coil is positioned perpendicular to the primary flat first wall and/or second wall of the implant. In some embodiments, the coil is positioned parallel to the primary load in the joint. In some embodiments, multiple coils are provided in the implant. In some embodiments, each coil is positioned parallel a direction of load during joint use. In some embodiments, the coil is adapted in material and strength to fix the implant at a desired joint space when not under load by the bones of the joint. In some embodiments, the coil is adapted in material and strength to provide cushion between the unloaded and a loaded state, and/or to provide a minimum joint spacing, for example when the coil is fully compressed. In some embodiments, the coil has an ability to be extended past its unloaded length (i.e. stretched), but to provide resistance to this extension. The resistance from extension provided by the coil may cooperate with the resistance from extension provided by ligaments of the joint and/or by the attachments of the implant to the first bone and/or the second bone. In the case of a medial compartment arthrosis where the normal 6 degrees valgus degrades to a 'bow legged' varus deformity, the implant may pad the damaged cartilage and cushion the joint,—even inflating selectively as described herein. In one embodiment, a combination of metal and polymer could stack shorter to longer parallel (Nitinol, other metal, or polymer) coils to fit the shape of a normal meniscus so that the longer coils are at the wide peripheral portion of the meniscus (joint edge) providing stability of the joint not available following varus deformity or meniscectomy. Another embodiment implant comprises coils between the inner and outer layers of the hip redundant or primary membranes.

Responsive Implants & Shifting Chambers

In some embodiments, the inflation, compliance, and or materials integrity with mesh, coils, or other fill materials fit the patients limb use needs not only structurally and anatomically at the time of surgical placement, but during normal activities of daily living. The implant may be compressed in certain locations during normal loading cycles, and compressed in other locations also during the same cycle. The implant may be responsive to this and shift the contents of a bladder or chambers (whether small or large). An example of this is shown in FIGS. 10A and 10B, where in the normal gait of a person the femur loads against the implant at the back of the joint (back of the knee), and pushes the contents of the chamber (s), toward the patella. It can be seen from this that if the angle of the femur to the tibia and load associated therewith were to shift to about 180 degrees, the contents of the chamber(s) could likewise shift to cushion the joint as the use of the joint required. That is, as the weight and axial load of walking moves the body central forces toward the 'step off' moment of that gait cycle, the chamber has also shifted, enduring oscillating balloon (macro) or vacuolar (micro) space size changes to accommodate and buffer the actions incumbent in natural limb use. As such, in some embodiments, the implant not only restores appendicular limb anatomy of the bone alignments and joint spaces, it also can compress with normal use forces and spring back to aid the best use of lever arms and joint interstacies as bones and joints relate to each other in activities of daily living. This type of implant may be used in multiple joint spaces throughout the body. To the degree the implant obtains and restores the joint spaces and are fixed in place, they may also thus be responsive during use of the joint thereafter.

Smart RADs

In some embodiments, the implant comprises a microminiature recorder and/or transmitter. The recorder (i.e. sensor) may collect joint loading data and comprise electronics that deliver data regarding joint loading. The recorder (i.e. sensor) may collect data regarding chemical or physiologic response at the implant location, such as the presence and composition of various biologic fluids at the sensor site. The sensor may be able to detect inflammatory responses in the joint. The sensor may be able to detect the spacing of the various joint components over time or at a particular time—such as the distance between the tibia and femur during a normal gait. The implant may comprise electronics that deliver data regarding joint loading or the other aspects of the joint sensed as listed herein or otherwise that could be sensed. The transmitters may provide feedback to the patient or to a caregiver. The feedback may be real-time, or may be uploaded periodically, or may be uploaded upon request. The feedback may be provided wirelessly. The transmitters may provide a patient an ongoing feedback and ability to adjust the joint use based to the feedback from the transmitter. For example, the transmitter might signal to the patient that he should adjust his gait to reduce the ligamentary stress in one manner or another. In another example, the transmitter might indicate to a physical therapist that a certain ligament is being stressed during normal use, and that might indicate to the therapist that the patient should strengthen a particular muscle or muscle group to compensate for and balance the stresses in the joint. In another example, the sensor and transmitters transmits information regarding positioning, ligamentary stresses and other information to a graphic display of real-time feedback, enabling a surgeon to visualize and quantify joint loading and balance during implantation. Thus, a surgeon can make an informed choice to modify implant positioning, adjust leg alignment and optimize soft tissue balance through a full range of motion.

In some embodiments, the implant may comprise spacers which can be expanded or reduced following implantation to adjust joint spacing and alignment. This expansion (or reduction) may occur days, weeks, or even years after implantation. The expansion (or reduction) may be done without need to open the joint in a surgery. The expansion (or reduction) may be done remotely. In some embodiments, sensors may be used to detect a need for adjustment of the joint spacing or cushioning. This may be in response to joint changes such as torn ligaments, other wear problems, changes in body weight and thus stress changes in the joint, or other changes, or simply due to the implant fatigue over time which is due to normal use but is not necessarily considered implant failure. In certain embodiments, the implant comprises an insert that may be activated by the patient or health care worker. For example, limb alignment may be achieved by remotely expanding (or reducing) the implant sizing (thickness or other specification) in a particular location in order to correct a varus to valgus alignment. Doing so may have beneficial effects on other parts of the body, such as in the appendicular skeleton (arms and legs) and axial skeleton (spine) given the natural symmetry. For example, a patient or care giver with their external device (such as a computer or Blackberry or iPhone) may expand or reduce, the medial knee compartment by external stimulus so that instead of being a knee with varus deformity and bone on bone (bow legged) the alignment was intentionally changed to normal 6 degree valgus (knock kneed). Nevertheless, if the patient had adjusted to his deformity for years and abruptly "corrected" it to completely normal, his back may act up with aching symptoms of 'out of alignment'. This is because the body attempts to adapt to deformity. Consequently, if a lower extremity fracture healing produces a two centimeter limb shortening, the proper treatment is not to add a 2 cm shoe lift onto the injured side, but rather to start with a one cm shoe lift. Although this may not make the limb lengths equal, it may 'balance the body' as perceived by the patient. In the case of an implant as provided herein that could adjust or be adjusted by doctor or patient, changes can be made to alignment and joint space, and then adjustments dealt with clinically as needed. If not via phone apps, other "black boxes" or tools such as a magnet placed externally adjacent to a medial compartment implant could be used to change the spacing inside the joint with an implant as described herein.

Attachment Elements and Couplers

In some embodiments the attachment elements of the implant comprises holes through which screws or other couplers may be placed to attach the implant to an attachment site (or connection site) in the bone of the knee. In some embodiments the attachment elements are also or alternatively called fixation elements or couplers. In some embodiments, the holes are created arthroscopically. In some embodiments the holes are pre-fabricated in the implant. In some embodiments, the holes may be made prior to implantation based on the patient's particular anatomy. In some embodiments, the holes are reinforced by a reinforcing material of the implant. The reinforcing material may be a polymer of sufficient durometer and/or tear resistance to reinforce the screw hole. The reinforcing material may comprise metal. In some embodiments, there is no preformed hole, but rather screws (or another coupler) secure the attachment tabs (which may be a non-balloon portion of the implant) to the joint component (bone, etc) by creating their own hole when implanted. In some embodiments, the implant may comprise tabs that are adapted to receive staples or other couplers described elsewhere herein. In some embodiments, the elasticity of the implant may allow it to stretch over the joint end and hook or snap into place, with the tendency of the material to contract acting to hold it in place (in part or wholly).

The implants described herein may comprise attachment elements (or tabs) which may then by attached or coupled to tissue of a component of the joint (whether to a bone or a ligament or a tendon or other joint component) by a coupling device. Coupling devices (or couplers) may comprise at least one of screws, snaps, washers, pins, sutures, suture anchors (metal and/or biodegradable), rivets, staples (with and/or without teeth), stabilizers, glues, hooks of cylindrical wire or flattened sheet metal into bone holes or slots respectively. The coupling devices may be resorbable or not. Also, the coupling devices may comprise at least one of strings (i.e. drawstrings), reigns, lassos, sutures, and lanyards. The strings, reigns, lassos, sutures, and/or lanyards may join with themselves and/or other coupling devices. The strings, reigns, lassos, sutures and/or lanyards may be directed not only into bone with or without anchors, but also through ligaments, tendons or loose segments of cartilage that the surgeon intends to preserve.

The posterior of the knee can be difficult to access without disturbing joint components (or in order to minimize such disturbance) such as tendons, ligaments, etc. Thus, in some embodiments, the implant comprises strings, reigns, lassos, and/or lanyards that may pass from the posterior of the implant via the intercondylar notch anteriorly to join with themselves and/or other coupling devices. These couplers may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is pre-molded, the coupler as described are adapted to move the implant to its final position with conformity to the condyle's posterior with minimal disturbance to the joint structures at the joint's posterior (minimal cutting, minimal moving, and or minimal detachment, for non-limiting example).

In some embodiments, the implant comprises a skirt (or sleeve) that conforms to the contours of the bone (whether a condyle of the femur, a patella, or a tibia) as a coupler.

In some embodiments, a screw through tab having reinforced center holes may be part of the implant. For example, the implant may comprise polymer covered metal washer holes. The screw may go through the holes. Another embodiment may comprise a staple having spikes as shown in FIGS. 13A-13D. FIGS. 13A-13D depict multiple views of a staple adapted to couple an implant to a bone of the joint. FIG. 13A depicts an embodiment of an implant 20 having a tab 10 *a* that is coupled to bone using a staple 12. FIGS. 13B & 13C depict a staple 12 as described herein having teeth 18. FIG. 13C depicts an embodiment of a tab 10 *a* that is coupled to bone using a staple 12 having teeth 18. Combinations of spikes and screws may be used in some embodiments, or combinations of other couplers. The implant may be configured to allow a surgeon the option of several types and sizes of couplers, as each patient differs with regard to size and depth of lesion, bone stock, regrowth capability, and compliance with advised recovery, and each surgeon has his own strengths and comforts when working with such implants.

The edge of the implant may have a depending skirt to secure or anchor the implant to the end of bone (femur), but may have one or more depending tabs (or appendages) that may be employed for similar functions as are discussed in other embodiments. The skirt (and/or tabs, and/or appendages) may tightly fit about the end of the femur, or the skirt can be secured by adhesive (e.g. HydroMed, Carbopol 934p, Polycarbophil AA1, xanthum gum, hydroxypropyl cellulose). Moreover, the lower portion of the skirt may be secured by a purse string suture or a suitable strand (elastic or tied) that is tightly bound about the outside of the skirt.

FIGS. 12A, 12B, and/or 12C alternatively may be used to describe a patch implant or a unicompartment knee implant described herein, having appendages 4 *a*, 4 *c*, extending from a balloon 6 and including holes 8 *a*, 8 *b*, 8 *c*, and/or tabs 10 *a*, 10 *b*, 10 *c*, 10 *d*, 10 *e*, 10 *f*, which may be used with couplers (not shown) to couple the implant to a bone of the knee joint (which may be the femur, the tibia, or the patella). Features shown in FIG. 12A, 12B, and or 12C are common to both the unicompartment knee implant (also discussed elsewhere herein) and the patch implant (also discussed elsewhere herein), although dimensions may differ as described elsewhere herein.

FIGS. 13A-13D depict multiple views of a staple 12 adapted to couple implant 14 (such as those described herein) to a bone 16 of the joint. FIG. 13A depicts a staple 12 coupling a tab 10 *a* of an appendage 4 *a* to the bone 16 of the joint (wherein the portion of the staple 12 embedded in the bone 16 is shown as a dashed line). FIG. 13B depicts a view of a staple 12 having teeth 18 to grasp the tab 10 *a* of the implant 14. Similarly, FIG. 13C depicts a view of a staple 12 having teeth 18 to grasp the tab 10 *a* of the implant 14. FIG. 13D depicts a staple 12 attaching the tab 10 *a* of an implant to a bone 16, the dotted lines show the portion of the tab 10 *a* that is compressed by the staple 12 and teeth 18 thereof.

In some embodiments, the implant is configured such that the tabs and/or couplers of the implant couple to the bone where there is no natural cartilage. In some embodiments, the implant may be adapted by the surgeon at the time of surgery such that the tabs are positioned where there is no natural cartilage.

In some embodiments, the implant comprises a tab and a hook that couples to the tab by wrapping around a component of the knee and securing the tab to the hook. In some embodiments, the implant comprises a tab and a hook that couples to the tab by wrapping around a condyle of the knee and securing the tab to the hook. In some embodiments, the implant is configured to wrap around a condyle of the knee and to secure a first appendage to a second appendage of the implant. In some embodiments the appendages are secured by couplers described herein. In some embodiments, the implant is pre-formed to fit to the condyle in such a wrapping manner.

In some embodiments, the implant comprises a methyl methacrylate what is placed into a balloon chamber that fits into a bone hole. Such an embodiment would generally fix the implant to the bone once the methyl methacrylate cures to a solid.

In some embodiments, the implant can be anchored with generic available sutures and suture anchors fixing and positioning material to bone with proper tensioning.

In some embodiments, fixation may comprise various methods and elements. For example the fixation to a bone (the first, the second or the third bone) may comprise any one of or a combination of a screw, a snap, a pin, a staple, bone in-growth materials, glue, a nanocomposite, and cement. The implant may comprise a snap fit option for fixation. The implant itself may be pre-molded to cup the first bone of the device, or the second bone of the device. The implant may instead have a snap-like device which fixes the device to the bone (the first, second, and/or third bone). In some embodiments, fixation comprises glue. In some embodiments, fixation comprises a nanocomposite. In some embodiments, the nanocomposite comprises a polyurethane hierarchical nanocomposite. Fixation may comprise gluing a nanocomposite to the implant. In other embodiments, fixation comprises bone in-growth materials. For example, bone in-growth may be achieved as described in Vasanji A (2012). In some embodiments the patient's preoperative x-rays, MRI, CT scan, or physical measurements are coordinated with implant custom fit options providing for translation of pathophysiological data into solid works and rapid prototypes. This may provide the forum for anatomic fit of the implant to the patient. Optionally, the implant may be selected from a set of pre-selected sizes of implants and then the device may have inherent malleability which is used to couple the implant to the bone end.

In some embodiments, the implant comprises a rim comprising metal at the edge or a portion of the edge of the implant which may comprise a hole or more than one hole through which a fixation element (snap, screw, staple, other, etc.) or more than one element can be placed to fix the implant to the bone. The rim may comprise Nitinol or another metal (memory metal or deformable).

The implant may be shaped to form a joint cap which is fixed to a first bone or a second bone or a combination thereof with a fixation element such as a screw or staple or cement or another means or combination of these or others as described herein. Cementing the implant in place is an alternative or may be used with other fixation elements (screws, snaps, ties, hooks, staples, etc). In some embodiments the implant is secured in place only by the nature of its location and placement within the joint space. That is, it may naturally be held in place by the surrounding structures (tissue, bone, ligaments) as well as its own geometry in three dimensions. In some embodiments, fixing of the implant to bone is achieved by combining autograph, allograph, xenograph, and/or prosthetic structures.

In some embodiments, the implant comprises a polymer joint cap that may be used similarly to the femoral component of a total knee replacement cement arthroplasty or like a hip resurfacing. In certain cases, cartilage may be sacrificed exposing more bone beneath the implant, and cement could be used as a traditional fixation technique. In certain embodiments, specific portions of cartilage can be removed to allow attachment of the implant undersurface with the bone by localized applications of cement, bone in-growth, tacking devices, countersunk screws, or Velcro like constructs wherein opposing surfaces are set to fix. In an implant embodiment employing a cement for fixation, the anterior cruciate ligament could still be saved maintaining joint stability and proprioception.

A snap fit fixation element ("snap") may alternatively (or additionally) be used. A snap may be a protuberance off the posterior implant surface may be used. The snap may comprise a mushroom shaped peg that may insert into predrilled bone holes. The holes in some embodiments are of corresponding shape to the peg (upside-down mushroom-shaped holes, or similarly shaped holes). The holes in some embodiments are columnar shaped holes. The holes may be at the periphery (edge) of the implant as it opposes bone, or generally located as noted herein where other fixation elements are located (e.g. see FIGS. 1-4B, 11, 12 at least). The snap may also fit into more central posterior implant areas. With the natural effects of joint fluid and temperature on hydrophilic polymers, the snap may be designed as to increase stability by swelling beneath the joint cortical surface in the early post operative interval. Implant removal may be facilitated by placing a cooling device over the snap site to shrink or loosen the attachment. In some embodiments the peg of the snap is one of: about 1 mm to about 10 mm in diameter, about 2 mm to about 8 mm in diameter, about 3 mm to about 6 mm in diameter, about 4 mm to about 5 mm in diameter, about 4.5 mm in diameter, 1 mm to 10 mm in diameter, 2 mm to 8 mm in diameter, 3 mm to 6 mm in diameter, 4 mm to 5 mm in diameter, and 4.5 mm in diameter. In some embodiments the mushroom head of the snap is one of: about 1 mm to about 10 mm in diameter, about 2 mm to about 8 mm in diameter, about 3 mm to about 6 mm in diameter, about 4 mm to about 5 mm in diameter, about 4.5 mm in diameter, 1 mm to 10 mm in diameter, 2 mm to 8 mm in diameter, 3 mm to 6 mm in diameter, 4 mm to 5 mm in diameter, and 4.5 mm in diameter The snap or protuberances may have a narrow base that extends perpendicularly from the tabs and/or implant posterior surface. The wider sphere as compared to the diameter of the snap columnar pedestal fits into a predrilled bone hole that matches the location to be fixed. In another embodiment, the snap may be more like anchor which expands into the bone upon insertion, much like a drywall anchor acts. Material compliance allows the distal snap to enter through cortical to cancellous bone. Exposure to joint fluid and bode temperature can expand the snap wherein the snap comprises a hydrophilic polymer to secure implant apposition. In some embodiments, a mushroom shaped protuberance off the posterior of the polymer joint implant is used, with stiff pegs that push connected spheres through a predrilled cortical bone hole. The joint implant may be cap-like holding to the bone by internal elasticity of the implant and further held by the fixation elements which may be snaps or other elements. In some embodiments, a drill into cortical hole cuts a broader cancellous swath to create a location for the ball of the snap. For example the peg hole may be 5 mm, while the mushroom cap head hole section diameter may be 7 mm. Other sizes may be appropriate for the peg hole such as about 1 mm, about 2 mm, about 3 mm, about 4 mm, about 5 mm, about 6 mm, about 7 mm, about 8 mm. Other sizes may be appropriate for the mushroom cap head hole section, such as about 2 mm, about 3 mm, about 4 mm, about 5 mm, about 6 mm, about 7 mm, about 8 mm, and about 9 mm. A hydrophilic polymer of the snap may then swell and hold the implant into place.

Other variations of fixing an implant to a bone may be known to one of skill in the art, and may include (but is not limited to) cross pins such as those used for ACL graft fixation, whip stitches with newer strong sutures as Ortho-Cord, or combinations of the above or others noted herein.

It should also be recalled that whereas the usual location of implants is over the major surface of a joint, the minor surfaces of joints may be selected optionally or additionally for coverage by an implant depending on the clinical need. In another iteration for fixation, magnets inside pegs or protuberances can allow for size adjustment internally or externally so as to engage a locking mechanism of implant to bone end.

In-Growth Features

In addition to the general in-growth that may occur based on the implant features described herein, the implant undersurface (adjacent the femur) may comprise an in-growth matrix. In some embodiments, at least a portion of the implant adjacent to the femur comprises bone in-growth materials. Such an implant can be attached by a series of tabs with or without holes, using screws, rivets, stabilizers, staples, tacks, washers, pins, snaps, or Sutures and suture anchors, for non-limiting example. The polymer of the implant substitutes for periosteum when the implant comprises living chondrocytes (e.g. Carticel) as the in-growth matrix on a surface of the implant. The polymer of the implant substitutes for periosteum when the implant comprises living chondrocytes (e.g. Carticel) as the in-growth matrix within an implant embodiment configured to reveal and/or release said chondrocytes over time and/or upon implantation.

The bone in-growth undersurface may be used for long term fixation of the tabs or rim. That is, whereas it is important for the surgery to secure the implant to the joint surface in the most desirable corrective location, it is also important in some embodiments to prepare the anatomic undersurface of bone by abrading it, removing about 0.5 mm of cortical bone so as to expose the underlying oxygen, blood, and nutrients of the patient to the undersurface of the implant that can gradually become incorporated into the limb bone. As this healing occurs over the course of weeks and months to one year post operation, the localized tacking sites may become less relevant and potentially inert. Thus, in some embodiments, the implant may comprise a biodegradable (bioresorbable) polymer or other material. The couplers may additionally and/or alternatively be biodegradable or durable (non-bioabsorbable). Once the implant is in place, it may serve to at least one of: pad defects, cushion the joint, and restore the original damage to the joint components. The end goal is to apply minimally morbid treatment that may refurbish arthritic limb regions, leaving only the small skin scar and remote memory of the healed physical mishap.

Undersurface implant materials may involve used of the art and science from Artelon or Gore-Tex research, as each has advantages and limitations. Several implant options per joint damage area may be available to enjoy the primary surgeons manipulation to fit the clinically recovery requirements best.

In some embodiments the implant comprises an in-growth patch on at least one of the first portion configured to engage the femur, the second portion configured to engage the second bone (whether the tibia or the patella), the side portion, and the appendage. In some embodiments, tissue is removed to facilitate in-growth.

The walls of the implant embodying features of the invention may be composite structures. For example, the innermost layer may be impervious to preclude escape of inflation or other filling media, a central layer may be porous or otherwise contain treatment or cell regeneration agents, and the outer layer may be a thin, but strong layer of a thermoplastic, such as a thermoplastic polyurethane for non-limiting example, which has microporosity sufficient to allow passage or egress of treatment or cell regeneration agents from the central layer (or second layer). The degree of microporosity to enable egress of treatment or cell regeneration agents from the central layer is found in polymer layers such as Chronoflex (e.g., ChronoFlexAR®, ChronoFlex AL®, ChronoFlec C®) or BIONATE (e.g., BIONATE I, BIONATE II, BIONATE 55D, BIONATE 65D, BIONATE 75D, BIONATE 80A, BIONATE 90A, BIONATE 55 or BIONATE 80). The external wall (and/or the bone engaging surface) of the implant may be coated and/or impregnated with a latticework of polymer that is surface sprayed or layered on the outside (or bone engaging surface) of the implant to promote cartilage tissue regeneration. This most external surface coating may contain living chondrocytes (for example, as is provided in the Carticel procedure by the Genzyme company), and/or may contain stem cells with or without directed gene mutations to enhance adherence of the coating to the implant. The bone engaging surface may comprise peaks and troughs. The living cells may be imposed in between (and/or provided in the) troughs of the implant surface while the surface areas of prominence (the peaks of the surface) may be used for at least one of: space validation, traction, and cell protection.

The implant embodying features of the invention may be used in a series of treatments wherein the first treatment involves use of autologous or minimally manipulated allograph interpositional tissues or xenograph, the second treatment involves the use of the same type of tissue added to stem cells or chondrocytes and the third treatment involving deployment of the implant if the first two fail or are ineffective.

The implant may comprise materials which allow for bone in-growth following implantation. In-growth may be facilitated by having interstices (or chambers) in the implant or in the fixation elements which are in the range of at least one of: about 10 microns to about 2000 microns, about 50 microns to about 1000 microns, about 100 microns to about 500 microns, about 300 microns to about 500 microns 10 microns to 2000 microns, 50 microns to 1000 microns, 100 microns to 500 microns, and 300 microns to 500 microns. In some embodiments, the chambers are sized to mimic the latticework of trabecular bone. In some embodiments, the chambers are formed by forming the implant using beads of the sizes noted above (e.g. 300 microns to 500 microns) and thereafter dissolving or otherwise breaking the beads such that interstices are left in the implant of the size of the beads. In an alternative, the beads may comprise a pharmacologic or other active agent which is absorbed or used by the body once implanted, and over time the interstices left by the beads (now gone due to absorption or use by the body) promote in-growth. Various methods known to one of skill in the art may be used to prepare the implant surface toward maximally effective union to bone.

Pharmacologics and Therapeutic Agents & Delivery thereof to Various Locations

In some embodiments the implant may comprise vacuoles of pharmacologic substances. The vacuoles may be on a bone-engaging portion of the implant. In some embodiments, the implant comprises bubbles comprising an active substance such as a pharmacologic substance or other active substance. In some embodiments, the implant comprises spaces filled with an active substance such as a pharmacologic substance (pharmacologic agent) or other active substance (active agent). In some embodiments, the active substance comprises iatrogenically gene mutated cells. In some embodiments, the implant may be inserted into the vacated space following removal of an infected routine total joint replacement. Current treatment of infected prostheses range from IV antibiosis, through arthroscopic washout to single or two stage replantations. With the worst infection the joint is often debrided of the prosthetic components and old cement, and then filled with new bone cement that is impregnated with antibiotics, leaving the hardened materials in place 6-12 months. During this interval 6-12 weeks IV antibiotics are typically used. In this situation if implants as noted herein were inserted with a calculated egress of antibiotics from the polymer container, both increased concentration of local antibiotics and decreased systemic side effects can benefit the patient. Further, since the polymer is both robust and compliant, use of the infected joint being treated is more realistic and comfortable, with a "bag of antibiotics and air" as opposed to a "chunk of cement."

Similar use of implants as noted herein for localized resected bone or soft tissue tumors may allow for drug delivery. Substances that can be delivered via implants noted herein are limitless, though may include (for non-limiting example) antibiotics, anti-fungal and Tb agents, anti-gout, anti-rheumatoid, and anti-tumor. Implants in certain embodiments may specifically elute contents via one or more portals from the primary chamber, and/or from a material liner of the implant. Implants in certain embodiments may specifically elute contents via the multiple chambers (in the 1 micron to 1 mm size) which are filled with the active and/or pharmacologic agent. Alternatively, the implant may have a port to an external source (outside the body or outside the space where the implant has been placed) of therapeutic agent which then may be delivered by elution or other manner from the implant itself. Stem cells such as living chondrocytes can be disbursed immediately and/or over time for regenerative purposes to regrow joint surface cartilage. Polymer layers of the implant material, in certain embodiments, may or may not be biodegradable. Disease fighting orthobiologics, both living and laboratory, can be dispensed via the implants.

Active agent delivery with implants as noted herein may be from their reservoirs wherein the agent is encapsulated in a polymer shell. Optionally matrices with entrapped polymer can elute active agents from the network, and/or the matrix can dissolve as a planned rate.

Still other iterations are contemplated. The implant may comprise micelles can be nano-sized hydrophilic shells that make up an implant layer that protects a core agent. Cell specific targeting drugs design to attach particular molecules may be delivered via implants noted herein as from a vesicle elution or matrix diffusion. For example, Gleevac targeting a GIST tumor molecule may specific address a clinical cancerous problem. Doxorubicine, a hydrophyobic anticancer agent at be emitted via polymer deliver from either a solid or inflated material interface between joint surfaces and/or from a ballooning aspect of that interpositional arthroplasty. Membranes (or walls) of the implants can be of singular or multiple layers with various relationships to each proximate layer so as to absorb or exude drugs using electroactive polymers through controlled transport(dopants) in and out of membranes. Hydrogels can be tailored to swell releasing entrapped molecules/cells through weblike matrices of the implant. Triggers from release of substances from certain embodiments of the implant can be internal or external, involving chemical factors such as pH, electromagnetic factors as magnetic fields, temperature variables as when 37 degrees body temperature induces an additional 30% pliability to the polymer wall, or ultrasonic release of vacuole content. Calculated mechanical vacuole wall thickness in relation to predictable acute, subacute or chronic intra-articular joint forces invoked by movement and limb use can release internal substances abruptly and/or over time.

Dendritic Macromolecules may deliver agent en masse from certain embodiments of the implant. The delivery in such situations may be via controllable size and structure, and may incorporate individual agent molecules or "hubs" via covalent bonds. Any combination of the nanoscopic developments can be created or assembled into the implants described herein and can be distributed, or oozed, or leaked, or expulsed from, or absorbed into as cleansing a noxious environment, or any combination thereof. Combined alternating forces such as materials that suck up or absorb noxious leukokynins or cathepsins while released useful viscolubricants such as Synvisc, Hyalgan or Orthovisc can be constructed to accommodate clinical need consistent with physical joint damage mandates or aligned with and consider of the natural history of disease processes so as to maximize either ones anticipated inevitable chronic deterioration or to thwart the adverse affects delaying degradation from arthritic or pathophysiologic processes.

Patient Symptoms

Symptoms for the patient requiring an implant described herein may include, for non-limiting example, osteoarthritis or rheumatoid or gouty arthritis.

Total Knee Arthroplasty (Dual Compartment):

Provided herein is an implant for placement on both condyles (medial and lateral) of the distal femur. In some embodiments, this is called a dual compartment implant since it covers both condyles of the femur. Such an implant comprises at least one interior (or inflatable chamber), and in some embodiments comprises a plurality of inflatable chambers (or interiors).

In some embodiments, the implant covers the "H" distal femoral cartilage segment (made up of both femoral condyles and the trochlear groove in between). The implant may absorb diffuse force, endure the millions of annual cyclic loads of both knee joints (including the patella-femur joint and the femur-tibia joints), along with rotational and shear forces up to six times body weight, at least.

In some embodiments, the implant comprises attachment tabs or attachment elements over the sides of both condyles medially and laterally. In some embodiments, the implant comprises attachment tabs or attachment elements in the intercondylar notch (or slot). In some embodiments, the implant comprises attachment tabs or attachment elements superiorly at the distal end of the femur anteriorly. In some embodiments, posterior reigns or suture-like lanyards cinch up the implant from inside the posterior intercondylar notch toward another connection site around the femur.

The posterior of the knee can be difficult to access without disturbing joint components (or in order to minimize such disturbance) such as tendons, ligaments, etc. Thus, in some embodiments, the implant comprises strings, reigns, lassos, and/or lanyards that may pass from the posterior of the implant via the intercondylar notch anteriorly to join with themselves and/or other coupling devices. These couplers may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is pre-molded, the coupler as described are adapted to move the implant to its final position with conformity to the condyle's posterior with minimal disturbance to the joint structures at the joint's posterior (minimal cutting, minimal moving, and or minimal detachment, for non-limiting example). In some embodiments at least a portion of the ligamentary structure of the knee is spared.

Although this description focuses on the distal femur as it articulates with the retropatellar and proximal tibial cartilages implants as described generally herein may be also and/or alternatively be used in conjunction with the tibia and/or the patella. Furthermore, separate and/or connected implant components may be inserted to restore natural function to the knee. In some embodiments whereas the implant caps the major joint surface and opposes remnant cartilage, the surgeon may elect to place the implant so that it opposes metal, polymer, or another surface reconstructive material.

Coupling devices to be used as part of the dual compartment implant may include any of those mentioned or described herein, for example. Such coupling devices may comprise at least one of strings (i.e. drawstrings), reigns, lassos, sutures, and lanyards. The strings, reigns, lassos, sutures, and/or lanyards may join with themselves and/or other coupling devices. The strings, reigns, lassos, sutures and/or lanyards may be directed not only into bone with or without anchors, but also through ligaments, tendons or loose segments of cartilage that the surgeon intends to preserve.

FIG. 1 depicts an embodiment of the implant 20 in a 2D view configured for dual condyle (distal femur) coverage. FIG. 1 depicts an embodiment of the knee implant 20 having appendages 4 *a*, 4 *b*, 4 *c*, 4 *d*, including holes 8 *a*, 8 *b*, 8 *c*, 8 *d* and tabs 10 *a*, 10 *b* extending from a balloon 6 and including slots 26 *a*, 26 *b* to accommodate ligaments (not shown) of the knee joint. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the tabs 10 *a*, 10 *b* contain holes. In some embodiments, the couplers create the holes 8 *a*, 8 *b*, 8 *c*, 8 *d*, or other holes (not shown) when the implant is placed against the distal femur 24. In some embodiments, the holes are pre-formed in the appendage prior to implantation. In some embodiments, the holes are reinforced as described elsewhere herein. In some embodiments, the holes are within the peripheral rim of the knee implant. In some embodiments, the holes are within the region of the intercondylar notch medially and/or laterally. In some embodiments, the holes are through the polymer. In some embodiments, the holes are through a reinforced rim. As shown here, the appendages in some embodiments may be different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. In some embodiments, the implant as shown in FIG. 1 can have regions 4 *a*, 4 *b*, 4 *c*, 4 *d* where no inflation exists and may be composed of solid or compliant materials. In some embodiments, the implant comprises a Dyneema® mesh. The implant may comprise Dyneema® fiber. In some instances, the implant comprises Dyneema Purity® fiber. In some embodiments, the implant comprises a Dyneema Purity® UG fiber. In some embodiments, the implant comprises a Dyneema Purity® VG fiber. The implant may comprise a fiber. The implant may comprise a polyethylene. The implant may comprise a polyethylene fiber.

Figure 2:
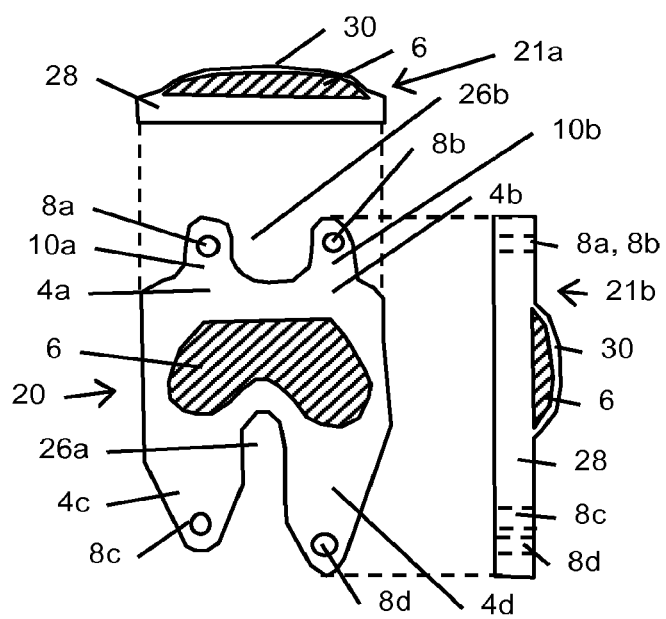
FIG. 2 depicts an embodiment of the knee implant having appendages including holes and tabs extending from a balloon and including slots to accommodate ligaments of the knee joint as well as side views of the same knee implant.

FIG. 2 depicts an embodiment of the knee implant 20 having appendages 4 *a*, 4 *b*, 4 *c*, 4 *d*, including holes 8 *a*, 8 *b*, 8 *c*, 8 *d* and tabs 10 *a*, 10 *b* extending from a balloon 6 and including slots 26 *a*, 26 *b* to accommodate ligaments of the knee joint as well as side views of the same knee implant. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8 *a*, 8 *b*, 8 *c*, 8 *d*, or other holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Shown in the embodiment depicted in FIG. 2 are the different hole placements from the side view, showing the differences in positioning of the holes to accommodate the differences in anatomic structure and size of the condyles. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. Additionally, as shown in the side views of the embodiment shown in FIG. 2, the balloon has a first wall 28 adapted to be adjacent the femur that is of a greater thickness than the second wall 30. In some embodiments, the first wall 28 is configured to have therapeutic benefits (pharmacologic, healing, and/or in-growth properties) as described elsewhere herein. The second wall 30 may additionally and/or alternatively be configured to have a therapeutic effect (pharmacologic, healing, and/or in-growth properties).

Figure 3:
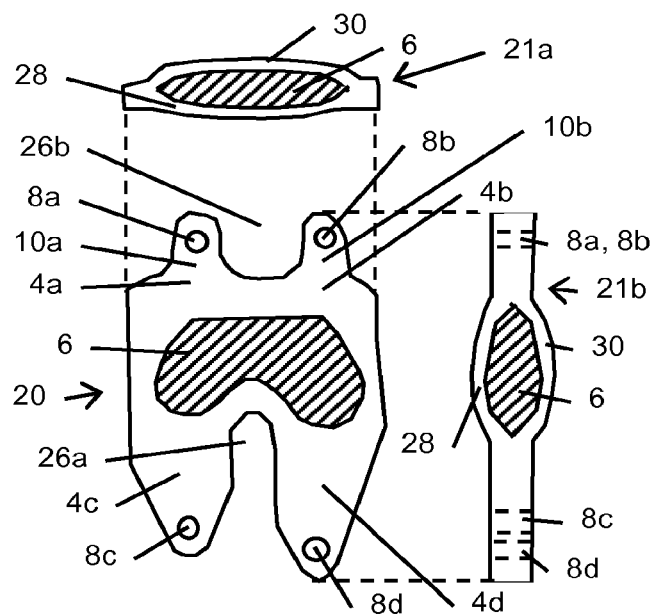
FIG. 3 depicts an embodiment of the knee implant having appendages including holes and tabs extending from a balloon and including slots to accommodate ligaments of the knee joint as well as side views of the same knee implant.

Nevertheless, differing thicknesses of the first wall 28 and the second wall 30 are not necessarily required in order to impart the therapeutic benefits (pharmacologic, healing, and/or in-growth) described elsewhere herein. For example, FIG. 3 depicts an embodiment of the knee implant 20 having appendages 4 *a*, 4 *b*, 4 *c*, 4 *d*, including holes 8 *a*, 8 *b*, 8 *c*, 8 *d* and tabs 10 *a*, 10 *b* extending from a balloon 6 and including slots 26 *a*, 26 *b* to accommodate ligaments of the knee joint as well as side views of the same knee implant. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8 *a*, 8 *b*, 8 *c*, 8 *d*, or other holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Shown in the embodiment depicted in FIG. 3 are the different hole placements from the side view, showing the differences in positioning of the holes to accommodate the differences in anatomic structure and size of the condyles. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. Additionally, as shown in the side views of the embodiment shown in FIG. 3, the balloon has a first wall 28 adapted to be adjacent the femur that is of approximately the same thickness than the second wall 30. In some embodiments, the first wall 28 is configured to have therapeutic benefits (pharmacologic, healing, and/or in-growth properties) as described elsewhere herein. The second wall 30 may additionally and/or alternatively be configured to have a therapeutic effect (pharmacologic, healing, and/or in-growth properties). The balloon 6 may be singular as depicted, or in certain embodiments, include a plurality of microscopic vesicular structures.

Figure 4A:
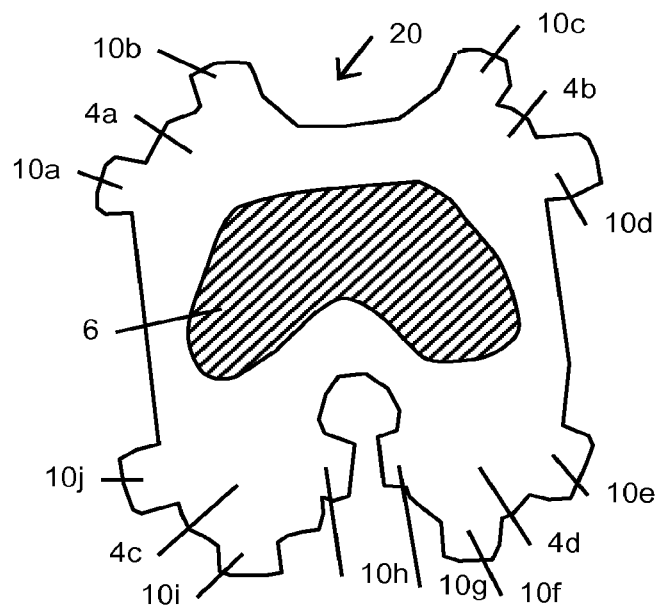
FIG. 4A depicts an embodiment of the knee implant having appendages including ten tabs extending from a balloon and including a slot to accommodate components of the knee joint.
Figure 4B:
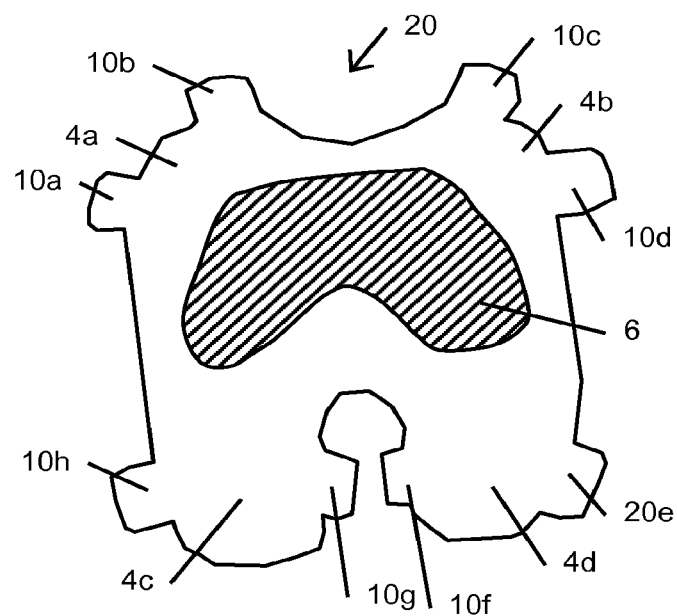
FIG. 4B depicts an embodiment of the knee implant having appendages including eight tabs extending from a balloon and including a slot to accommodate components of the knee joint.

FIG. 4A depicts an embodiment of the knee implant 20 having appendages 4 *a*-4 *d* including ten tabs 10 *a*-10 *j* extending from a balloon 6 and including a slot 26 *a* to accommodate components (such as ligaments or other tissues whether soft tissues, hard tissues, tendons, and/or others) of the knee joint (not shown). The tabs 10 *a*-10 *j* are not shown with holes in this embodiment, however if screws are used as couplers, such holes may be pre-drilled or formed in situ by the screws. Additionally and/or alternatively, staples, washers, pins, snaps, or sutures may be used (as described elsewhere herein) in order to couple the implant to the bone (femur, for example). Other couplers as described elsewhere herein may also and/or alternatively be used in this coupling process. Furthermore, the number of tabs may be fewer or greater than the ten depicted in order to achieve optimal placement and coupling to the bone. For example, FIG. 4B depicts an embodiment of the knee implant 20 having appendages 4 *a*-4 *d* including eight tabs 10 *a*-10 *h* extending from a balloon 6 and including a slot 26 *a* to accommodate components (such as ligaments or other tissues whether soft tissues, hard tissues, tendons, and/or others) of the knee joint (not shown). In certain embodiments, the implant comprises 0, 1, 2, 3, 4, 5, 6, 7, 8, 9, or 10, 11, 12, 13, 14, 15, 16, 17, 18, 19, and/or 20 tabs. The tabs may be located on either side of the condyles, including the superior, mid, and posterior portions. Any tab may be also and/or alternatively located inside the medial and intercondylar notch.

Figure 5:
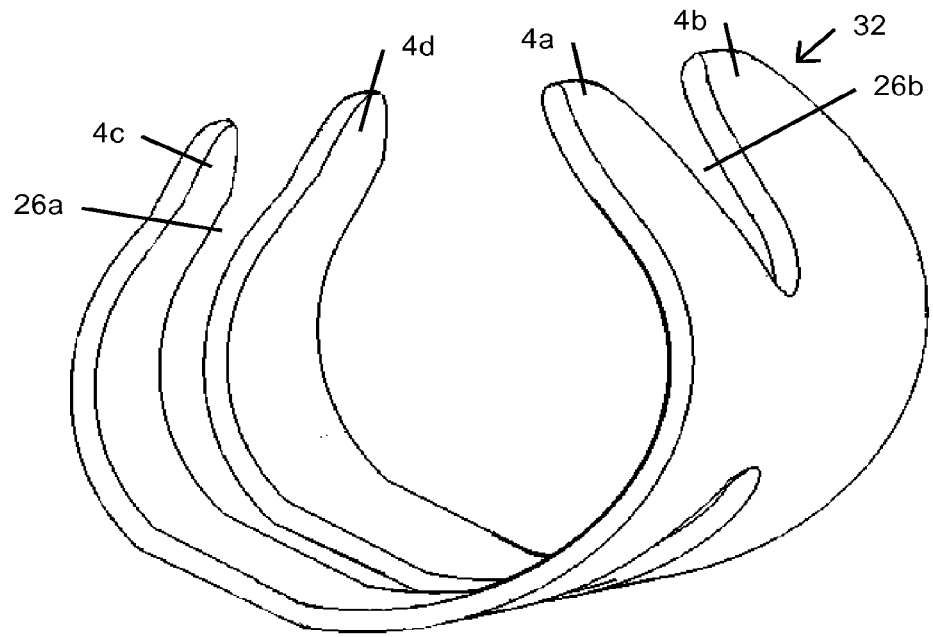
FIG. 5 depicts an embodiment of the knee implant curved to simulate curvature about the condyles of a femur, the implant having appendages extending from an uninflated balloon (not shown) and including slots to accommodate ligaments of the knee joint.

FIG. 5 depicts an embodiment of the knee implant 32 curved to simulate curvature about the condyles of a femur, the implant having appendages 4 *a*-4 *d* extending from an uninflated balloon (not shown) and including slots 26 *a*, 26 *b* to accommodate components (such as ligaments or other tissues whether soft tissues, hard tissues, tendons, and/or others) of the knee joint (not shown). This figure also shows an implant comprising a solid compliant material, having no balloon whatsoever. The implant may comprise additional curvatures and/or slots to accommodate other ligaments and/or tissues. In some embodiments, the implant is configured to conform about various hard and/or soft tissues of the joint, such as bone, ligaments, tendons, etc. In some embodiments, the balloon is inflated once the implant is positioned within the joint. In other embodiments, the balloon is partially inflated prior to being positioned within the joint. In other embodiments, the balloon is at least partially inflated prior to being positioned within the joint. In some embodiments, the balloon is fully inflated prior to being positioned within the joint. In some embodiments, the implant is configured to allow an operator to adjust the amount of balloon inflation in situ (whether by adding inflation medium or removing inflation medium, or both, or neither). Couplers as described elsewhere herein may be used to couple the implant 32 to the distal femur.

Figure 6A:
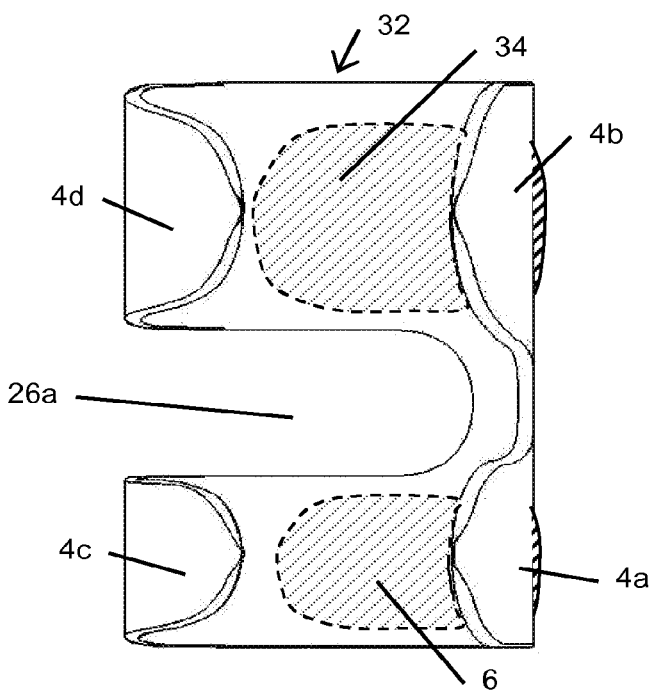
FIG. 6A depicts a top-down view of an embodiment of the knee implant curved to simulate curvature about the condyles of a femur, the implant having appendages extending from two inflated balloons and including slots to accommodate components of the knee joint.
Figure 6B:
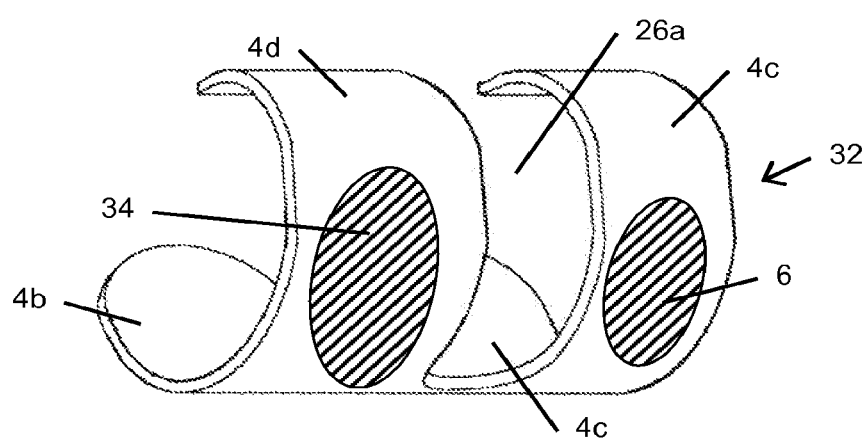
FIG. 6B depicts a bottom-up view of an embodiment of the knee implant curved to simulate curvature about the condyles of a femur, the implant having appendages extending from two inflated balloons and including slots to accommodate components of the knee joint.

FIG. 6A depicts a top-down view of an embodiment of the knee implant 32 curved to simulate curvature about the condyles of a femur, the implant having appendages 4 *a*-4 *d* extending from two inflated balloons 6, 34 and including a slot 26 *a* to accommodate components of the knee joint. FIG. 6B depicts a bottom-up or anterior oblique view of the same embodiment of the knee implant 32 curved to simulate curvature about the condyles of a femur, the implant having appendages 4 *a*-4 *d* extending from two inflated balloons 6, 32 and including a slot 26 *a* to accommodate components of the knee joint. Couplers as described elsewhere herein may be used to couple the implant 32 to the distal femur. As shown in FIGS. 6A and 6B, the appendages 4 *a*-4 *d* in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Likewise, the dimensions of the balloon 34 that is adapted for placement over the medial condyle may be a different shape and/or size than the balloon 6 over the lateral condyle (the medial condyle being larger, thus the balloon 34 may be larger for that location) Alternatively and/or additionally, as described elsewhere herein, for various reasons such as injury, realignment needs, injury, etc, there may be a need for more reconstruction of one condyle than needed for the other, thus the inflation medium might be different in one balloon (or a portion thereof) than in the other balloon (or another chamber within the same balloon), or there may be need for a different shaped balloon in one location than in another location. Embodiments provided herein can accommodate these requirements based on materials of fillers, appendages, balloons, walls, and dimensions and chamber options of the implant and its components.

Figure 7:
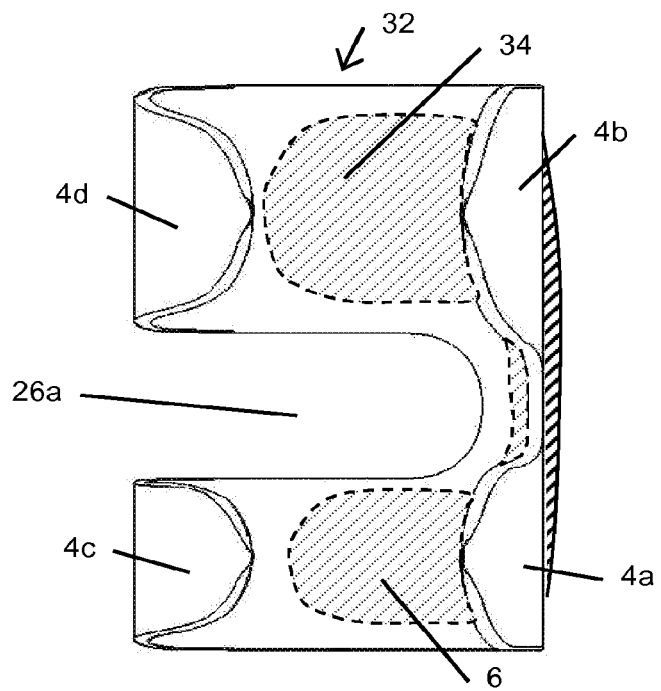
FIG. 7 depicts a top-down view of an embodiment of the knee implant curved to simulate curvature about the condyles of a femur, the implant having appendages extending from an inflated balloon and including slots to accommodate components of the knee joint.

FIG. 7 depicts a top-down view of an embodiment of the knee implant 32 curved to simulate curvature about the condyles of a femur, the implant having appendages 4 *a*-4 *d* extending from an inflated balloon 6 and including slots to accommodate components of the knee joint. Couplers as described elsewhere herein may be used to couple the implant 32 to the distal femur. As shown here, the appendages 4 *a*-4 *d* in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Likewise, the dimensions of the portion of the balloon that is adapted for placement over the medial condyle may be a different shape and/or size than the portion of the balloon over the lateral condyle (the medial condyle being larger, thus the balloon may be larger for that location) Alternatively and/or additionally, as described elsewhere herein, for various reasons such as injury, realignment needs, injury, etc, there may be a need for more reconstruction of one condyle than needed for the other, thus the inflation medium might be different in a portion or chamber of an implant embodiment having a plurality of inflation chambers in a single balloon, or there may be need for a non-symmetric balloon. Embodiments provided herein can accommodate these requirements based on materials of fillers, appendages, balloons, walls, and dimensions and chamber options of the implant and its components.

Figure 8:
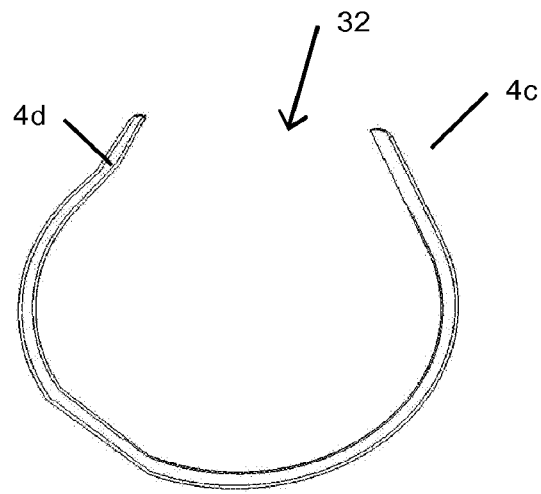
FIG. 8 depicts a side view of an embodiment of the knee implant curved to simulate curvature about at least one condyle of a femur, the implant having appendages extending from an uninflated balloon (not shown).

FIG. 8 depicts a side view of an embodiment of the knee implant 32 curved to simulate curvature about at least one condyle of a femur, the implant having appendages 4 *b*, 4 *d* extending from an uninflated balloon (not shown). This depiction covers the maximum anticipated distal femoral contour; other iterations may be smaller, or shorter covering limited areas of the circumference of the femoral curvatures. This figure also provides a lateral view for a solid implant (without a chamber therein) wherein the material thickness and/or layering provide cushioning.

FIG. 9A depicts a side view of an embodiment of the knee implant 20 curved about at least one condyle 22 of a femur 24, the implant 20 having appendages 4 *b*, 4 *d* extending from an uninflated or minimally inflated balloon 6. In this view, the knee is positioned essentially in extension (straight), showing the tibia 36, fibula 38, and patella 40 of the knee. Note that although there would be other joint structures and knee structures in a true depiction of an implant positioned in the knee, this view of the implant and bones is greatly simplified for ease of understanding of the implant and the joint relative (and approximate) positions and placement. Couplers as described elsewhere herein may be used to couple the implant 20 to the distal femur 24 and/or the condyle 22 thereof (in this image the medial condyle, at least since it is primarily a one-side view of the joint and implant). For the sake of simplicity FIG. 9A and the implant embodiment depicted show of the femur with opposition to the other surfaces of both knee joints (between femur and tibia, and femur and patella), the areas of contact varying according to activity, forces, and range of motion. Other implant iterations may apply to opposing surfaces.

FIG. 9B depicts a side view of an embodiment of the knee implant 20 curved about at least one condyle 22 of a femur 24, the implant 20 having appendages 4 *b*, 4 *d* extending from an inflated balloon 6. In this view, the knee is positioned essentially in extension (straight), showing the tibia 36, fibula 38, and patella 40 of the knee. Note that although there would be other joint structures and knee structures in a true depiction of an implant positioned in the knee, this view of the implant and bones is greatly simplified for ease of understanding of the implant and the joint relative (and approximate) positions and placement. Couplers as described elsewhere herein may be used to couple the implant 20 to the distal femur 24 and/or the condyle 22 thereof (in this image the medial condyle, at least since it is primarily a one-side view of the joint and implant). In FIG. 9B wherein the balloon is inflated, as compared to FIG. 9A wherein the balloon is not inflated or is minimally inflated, the balloon second wall 30 is closer to and/or contacting the tibial plateau 42 (articular surface) when the balloon 6 is inflated. Likewise, FIG. 9C depicts a side view of an embodiment of the knee implant 20 curved about at least one condyle 22 of a femur 24, the implant 20 having appendages 4 *b*, 4 *d* extending from an inflated balloon 6 and having couplers 44 *a*, 44 *b* (which may be, for non-limiting example, staples or screws, pins, or snaps) coupling the appendages 4 *b*, 4 *d* to the femur. In this view, the knee is positioned essentially in extension (straight), showing the tibia 36, fibula 38, and patella 40 of the knee. Where the inflated balloon as seen in FIG. 9B may fill in existing pathologic defects of the joint surface, the medium of inflated and specific balloon location and durometry with the material of the implant may also be constructed so as to force the bones opposed, e.g. the femur and tibia, into a more natural limb alignment such as six (6) degrees valgus. However, if the patient being treated has variations from normal in the affected knee as illustrated by examining and measuring the opposite normal side, then the implant inflation and pressures or balloon location may be adjusted from the population norms thus customizing this implant to the clinical case under consideration. Fixation devices may be appropriately applied at various knee range of motion intervals from full extension (zero degrees) to full flexion (usually 135 degrees) as the knee is adjusted and the implant secured under anesthesia.

FIG. 10A depicts a side view of an embodiment of the knee implant 20 curved about at least one condyle 22 of a femur 24, the implant 20 having appendages 4 *b*, 4 *d* extending from an inflated balloon 6 and showing the inflation medium 46 moved anteriorly toward the patella 40 when the knee joint is slightly flexed. The dynamic nature of the implant material and/or content may be responsive to body forces as a physiological rather than rigid structure. The filling of space inside the joint may add stability to the patient and to the joint. Likewise, FIG. 10B depicts a side view of an embodiment of the knee implant 20 curved about at least one condyle 22 of a femur 24, the implant 20 having appendages 4 *b*, 4 *d* extending from an inflated balloon 6 and having couplers 44 *a*, 44 *b* (which may be, for non-limiting example, staples or screws, pins or snaps) coupling the appendages 4 *b*, 4 *d* to the femur 24 and showing the inflation medium 46 moved anteriorly toward the patella 40 when the knee joint is slightly flexed.

For example, FIG. 14 depicts an embodiment of the knee implant 20 having appendages 4 *a*, 4 *b*, 4 *c*, 4 *d*, including holes 8 *a*, 8 *b*, 8 *c*, 8 *d* and tabs 10 *a*, 10 *b* and including slots 26 *a*, 26 *b* to accommodate ligaments of the knee joint as well as side views of the same knee implant. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8 *a*, 8 *b*, 8 *c*, 8 *d*, or other holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Shown in the embodiment depicted in FIG. 14 are the different hole placements from the side view, showing the differences in positioning of the holes to accommodate the differences in anatomic structure and size of the condyles. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. Additionally, as shown in the side views of the embodiment shown in FIG. 14, the implant has a first wall 28 adapted to be adjacent the femur that is of approximately the same thickness than the second wall 30. In some embodiments, the first wall 28 is configured to have therapeutic benefits (pharmacologic, healing, and/or in-growth properties) as described elsewhere herein. The second wall 30 may additionally and/or alternatively be configured to have a therapeutic effect (pharmacologic, healing, and/or in-growth properties). Additionally, the thickness of the implant in certain locations is variable to add cushioning to the implant as well as to provide joint spacing. In certain embodiments, the material is not variable in thickness, but provides the same cushioning and/or joint spacing for the bones of the joint. The central region in the embodiment of FIG. 14 is thicker material to add at least one of: cushioning, buffering, joint space, restore cushioning, and to respond to clinical need.

Any of the balloons described herein with regard to any of the figures may add cushioning, padding, strength, durability, flexibility, or any other aspect noted herein, and need not be a chamber per se, nor be inflatable per se. Rather they are merely distinguishable in certain embodiments from the walls which are on either side of them in composition or function or both. In some embodiments, the balloon and its interior is not materially different in composition or function from one of the walls. In some embodiments, they are not materially different in composition or function from either of the walls.

Figure 15A:
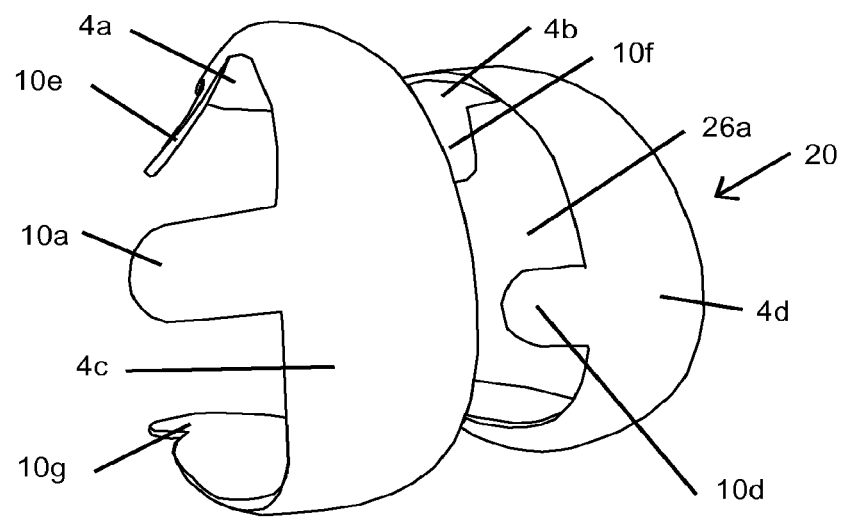
FIGS. 15A, 15B, and 15C show several views of an embodiment of an implant which has no definable chamber, rather the material of the implant itself provides the cushion to the bones of the joint (at least).
Figure 15B:
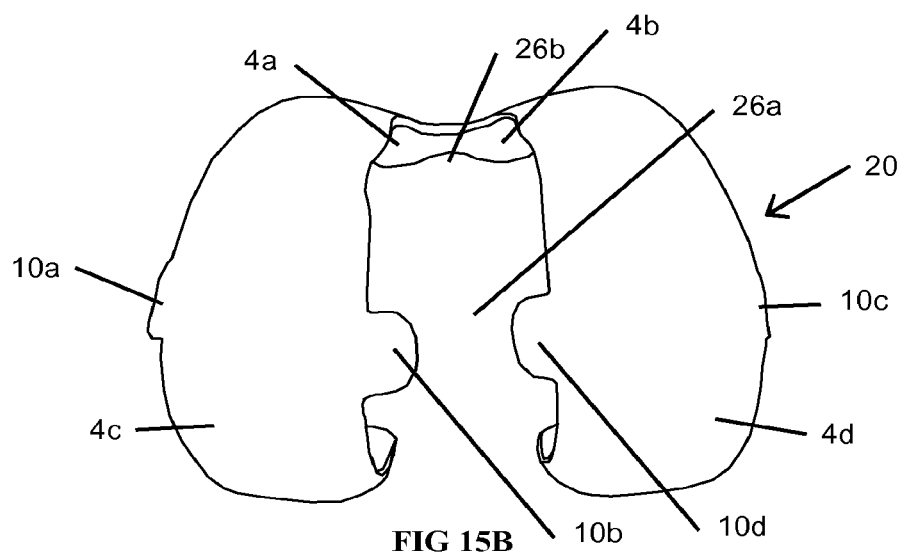
Figure 15C:
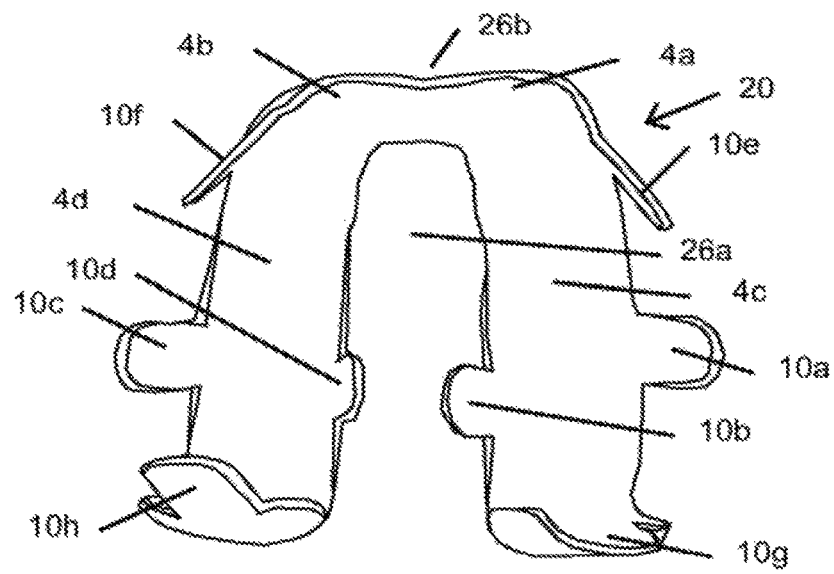

FIGS. 15A, 15B, and 15C show several views of an embodiment of an implant which has no definable chamber, rather the material of the implant itself provides the cushion to the bones of the joint (at least). The implant in 15A, 15B, and 15C is generally H or V-shaped, having a slot 26 *b* that is significantly smaller than as shown other embodiments (for example FIGS. 3, 4, 5, 6A, 6B, 7, 14). In certain embodiments, an implant shaped generally like FIGS. 15A, 15B, and 15 *c* may comprise a chamber which, if the implant were shown in cross section, may comprise a different material than the wall of the implant itself, or may be the same material but with different geometric or chemical or physical properties, as noted herein. FIGS. 15A, 15B, and 15C depict an embodiment of the knee implant 20 having appendages 4 *a*, 4 *b*, 4 *c*, 4 *d* and tabs 10 *a*, 10 *b*, 10 *c*, 10 *d*, 10 *e*, 10 *f*, 10 *g*, 10 *h* and including slots 26 *a*, 26 *b* to accommodate ligaments of the knee joint. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. The slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. The thickness of the implant in certain locations is variable to add cushioning to the implant as well as to provide joint spacing. In certain embodiments, the material is not variable in thickness, but provides the same cushioning and/or joint spacing for the bones of the joint.

Figure 16:
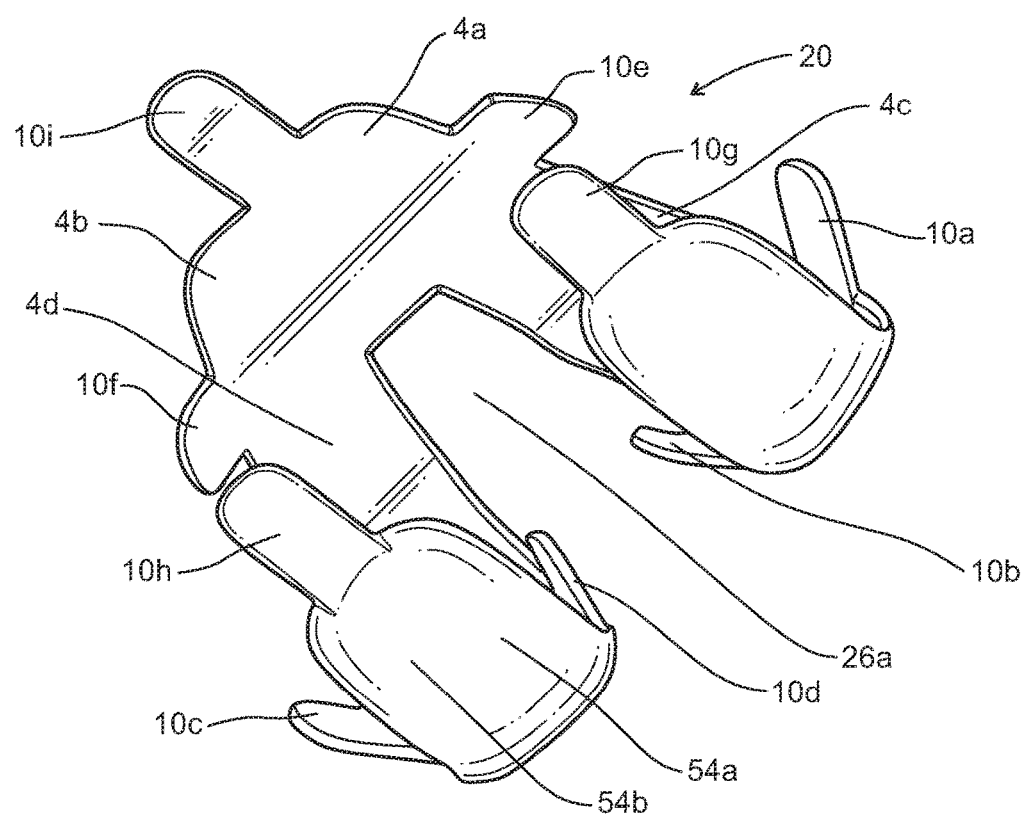
FIG. 16 depicts a knee implant embodiment that is generally H or V-shaped, having a slot 26 b that is significantly smaller than other embodiments, and in this embodiment is effectively replaced with a tab 10 i at the same location (e.g. 10 i).

FIG. 16 depicts a knee implant embodiment that is generally H or V-shaped, having a slot 26 *b* that is significantly smaller than other embodiments, and in this embodiment is effectively replaced with a tab 10 *i* at the same location (e.g. 10 *i*). FIG. 16 depicts an embodiment of the knee implant 20 having appendages 4 *a*, 4 *b*, 4 *c*, 4 *d* and tabs 10 *a*, 10 *b*, 10 *c*, 10 *d*, 10 *e*, 10 *f*, 10 *g*, 10 *h*, 10 *i* and including a slots 26 *a* to accommodate ligament(s) of the knee joint. Couplers as described elsewhere herein may be used to couple the implant 20 to the distal femur. Contour lines 54 *a*, 54 *b*, for example, are also depicted in FIG. 16, however these are not necessarily significant other than to show contour of parts of the implant 20, although they may be in the case where a mesh is provided in the implant. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. The slot 26 *a* may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. The thickness of the implant in certain locations is variable to add cushioning to the implant as well as to provide joint spacing. In certain embodiments, the material is not variable in thickness, but provides the same cushioning and/or joint spacing for the bones of the joint. In certain embodiments, an implant shaped generally like FIG. 16 may or may not comprise a chamber which, if the implant were shown in cross section, may comprise a several materials which may be the same as or different from any wall of the implant itself, or may be the same material but with different geometric or chemical or physical properties, as noted herein.

Figure 17:
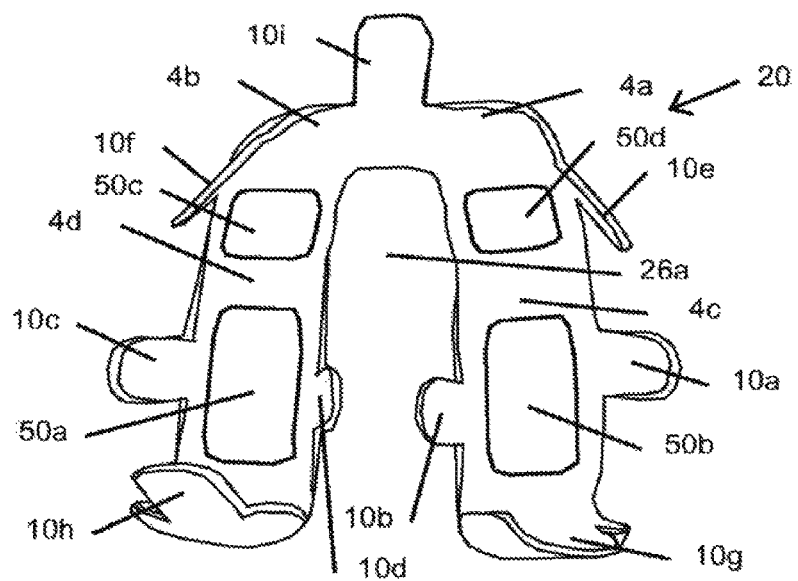
FIG. 17 depicts a knee implant embodiment similar to FIG. 16 which shows a posterior view including the location (s) 50 a-50 d where a fill material such as cement may be placed.

FIG. 17 depicts a knee implant embodiment similar to FIG. 16 which shows a posterior view including the location(s) 50 *a*-50 *d* where a fill material such as cement may be placed. The fill material may be added in any one location 50 *a*, 50 *b*, 50 *c*, or 50 *d*, or added in several of locations 50 *a*, 50 *b*, 50 *c*, and 50 *d* or likewise be added anywhere on the first or second wall of the implant which contacts the first, second, and/or third bone. The fill material may be used to both cushion (as do balloons 6 in other figures) and/or secure the device to the bone in the case of a bone cement or a combination of these functions. In the case where the cement is used as the fill material, the cement may be used in an element that may or may not have any, some, or all of tabs 10 *a*-10 *i*. The cushion, thus can act as a coupler (fixation element) and/or as a cushion and/or spacer for the joint bones. The cushion (whether a fill material such as cement or another material) may also be placed adjacent to a first wall or second wall, and not necessarily between said first wall and second wall.

Figure 18:
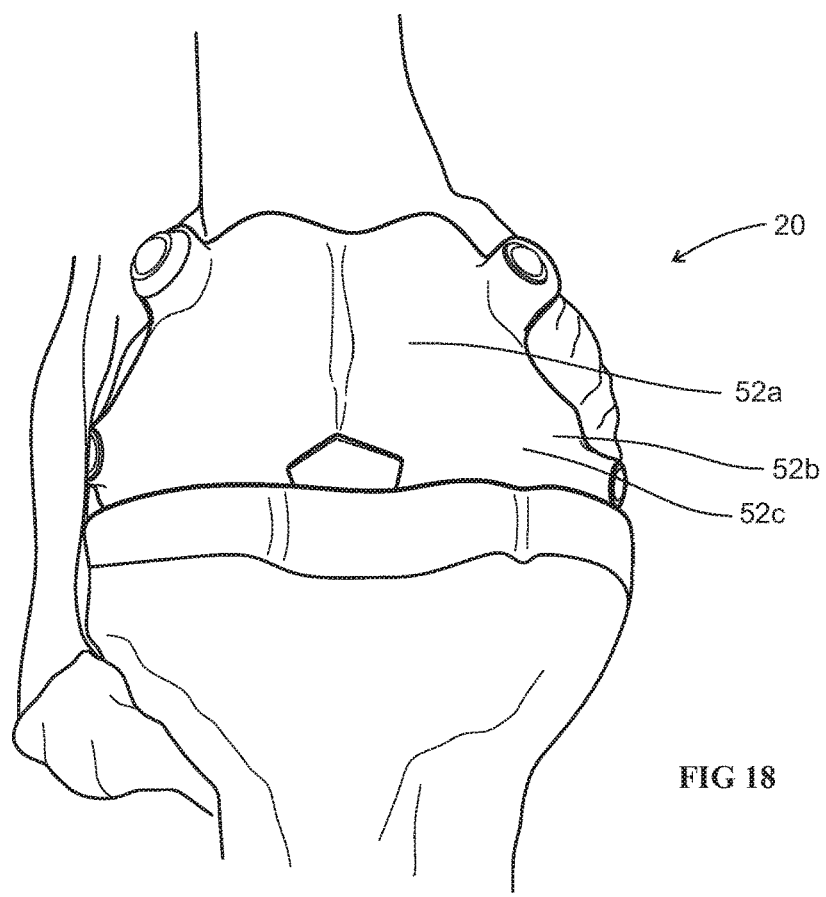
FIG. 18 is an anterior-posterior view of an embodiment of the implant 20 attached to a knee model.

FIG. 18 is an anterior-posterior view of an embodiment of the implant 20 attached to a knee model. The implant here comprises chambers 52 *a*, 52 *b*, 53 *c*, at least (in this case, nano-inflated air pockets). Although sparsely shown in this embodiment, the frequency, size, etc. could be adapted to smaller chambers, larger chambers, more frequent chambers, more concentrated in particular areas of the implant, less concentrated in particular areas of the implant, or similarly adjusted. The chambers can be diffuse, of any size, containing compressible gas (air), cells, pharmacologics, liquids, beads, metals, or other materials as noted herein.

Figure 19:
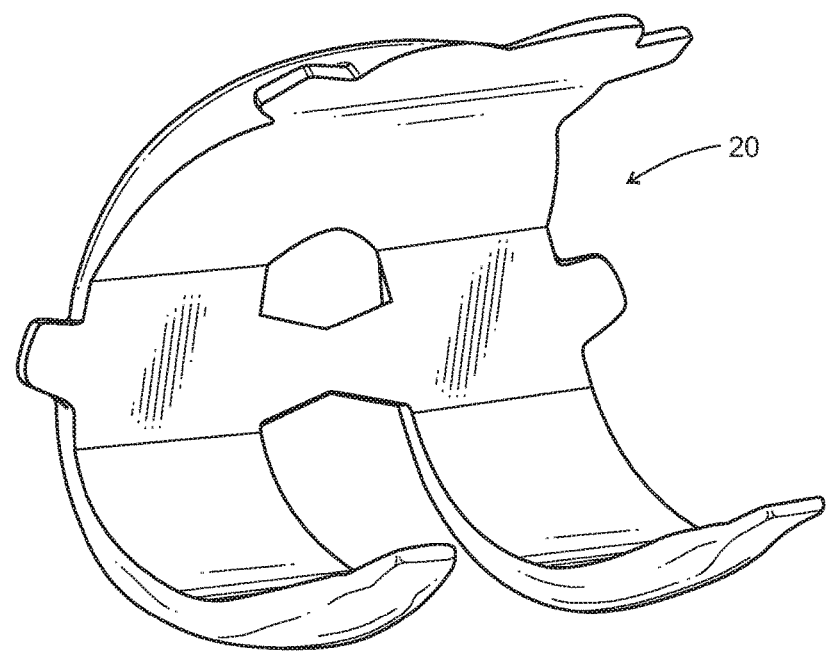
FIG. 19 depicts an implant 20 which is more squarely cut for interface with a femur, for example, which has been cut square such as is done in certain total knee arthroplasty procedures.

FIG. 19 depicts an implant 20 which is more squarely cut for interface with a femur, for example, which has been cut square such as is done in certain total knee arthroplasty procedures. The implant in this situation may comprise a polymer alone (of soft or hard durometer) and/or metal. The walls may be contiguous or include a chamber that is optionally filled or Tillable as noted herein. Although tabs are shown in FIG. 19, these are optional in embodiments where another attachment element (fixation element) is used such as cement or a metal pin or screw or snap through an appendage of the device.

Figure 20A:
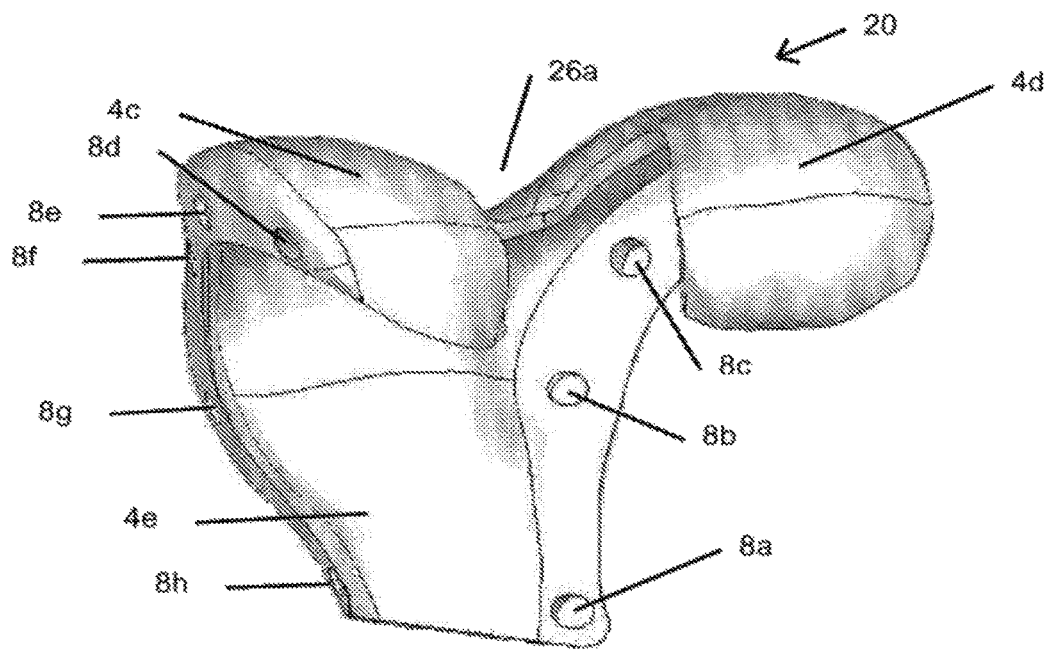
FIGS. 20A and 20B depict a knee implant embodiment that is generally V-shaped or Y-shaped, and in this embodiment the notch 26 b of other embodiments, or the tab 10 i of other embodiments is effectively replaced with an appendage 4 e at the same location.
Figure 20B:
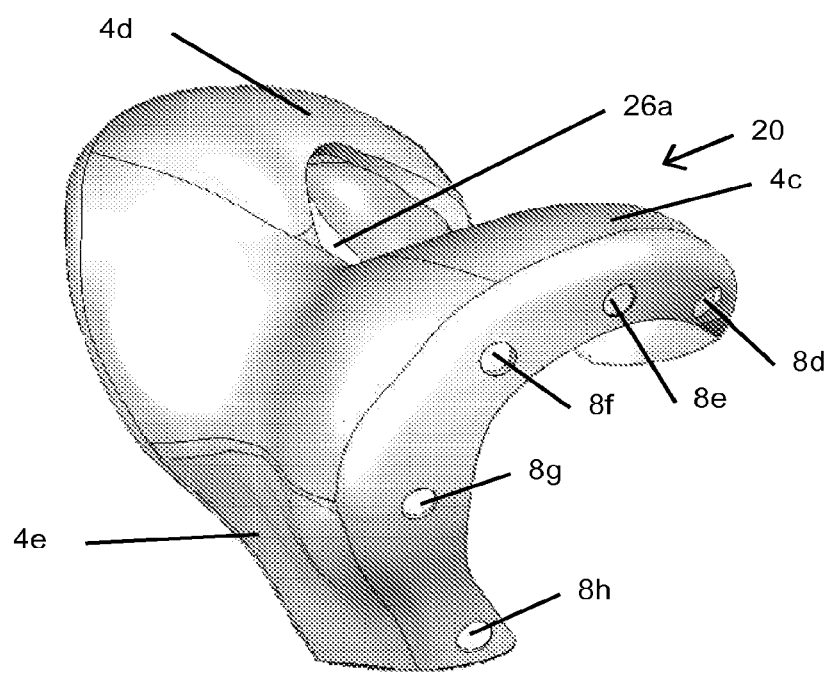

FIGS. 20A and 20B depict a knee implant embodiment that is generally V-shaped or Y-shaped, and in this embodiment the slot 26 *b* of other embodiments, or the tab 10 *i* of other embodiments is effectively replaced with an appendage 4 *e* at the same location. FIG. 20A depicts an embodiment of the knee implant 20 having appendages 4 *c*, 4 *d*, and 4 *e* and holes 8 *a* (not shown, in FIG. 20B), 8 *b* (not shown, in FIG. 20B), 8 *c* (not shown, in FIG. 20B), 8 *d*, 8 *e*, 8 *f*, 8 *g*, 8 *h*, 8 *i*, (not shown, substantially similarly positioned as 8 *e* on the same edge as 8 *a*-8 *c* of FIG. 20A), 8 *j* (not shown, substantially similarly positioned as 8 *d* on the same edge as 8 *a*-8 *c* of FIG. 20A), and including a slot 26 *a* to accommodate ligament(s) of the knee joint. Couplers as described elsewhere herein may be used to couple the implant 20 to the distal femur through slots 8 *a*-8 *j*. Contour lines are also depicted in FIGS. 20A and 20B, however these are not necessarily significant other than to show contour of parts of the implant 20, although they may be in the case where a mesh is provided in the implant. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the tabs comprise holes. In some embodiments, the couplers create holes (not shown) when the implant is placed against the distal femur. In some embodiments, the holes are within the peripheral rim of the knee implant. In some embodiments, the holes are within the region of the intercondylar notch medially and/or laterally. In some embodiments, the holes are through the polymer. In some embodiments, the holes are through a reinforced rim. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. The slot 26 *a* may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. The thickness of the implant in certain locations is variable to add cushioning to the implant as well as to provide joint spacing. In certain embodiments, the material is not variable in thickness, but provides the same cushioning and/or joint spacing for the bones of the joint. In certain embodiments, an implant shaped generally like FIG. 20A or 20B may or may not comprise a chamber which, if the implant were shown in cross section, may comprise a several materials which may be the same as or different from any wall of the implant itself, or may be the same material but with different geometric or chemical or physical properties, as noted herein. As shown in FIGS. 20A and 20B, thickness of between the first wall (part configured to touch the femur condyle) and the second wall (part configured to touch the tibia), is shown for example in the slot 26 *a* (which may be called a notch herein), thus showing a side wall as described elsewhere herein to provide the thickness to the implant at the condyle(s). This thickness may be a result of a thickness of a material of the implant (as in where the implant comprises a compliant polymer), or due to an inflation of a balloon that resides between the first wall and the second wall and the side wall. In some embodiments, the implant comprises a Dyneema® mesh. The implant may comprise Dyneema® fiber. In some instances, the implant comprises Dyneema Purity® fiber. In some embodiments, the implant comprises a Dyneema Purity® UG fiber. In some embodiments, the implant comprises a Dyneema Purity® VG fiber. The implant may comprise a fiber. The implant may comprise a polyethylene. The implant may comprise a polyethylene fiber.

In all descriptions provided herein of the dual compartment implant, the implant may instead be configured to couple to or emerge from the tibia and/or patella. In all descriptions provided herein of the dual compartment implant, the implant may instead be configured to couple to the tibia. It is the intention and understanding that the implant is suited for this purpose in certain embodiments with adjustments to account for dimensional differences of the tibia. Most descriptions provided herein are directed to embodiments coupling the implant to the femur, however, this is primarily for ease of description and continuity, and does not preclude embodiments wherein the implant is coupled to the tibia. Likewise, as noted elsewhere herein, there are embodiments where the implant may be coupled to two bones (at least), for example to both a tibia and a femur.

Patch

Some embodiments of the implant are configured to repair isolated lesions wherein osteochondral defects as in osteonecrosis create craters in the cartilage that need 'filling in' with a patch. Various size lesions of cartilage defects can be accommodated by the implants provided herein which may have balloons of at least one of: at most about 0.5 cm in diameter, at most about 0.75 cm in diameter, at most about 1 cm in diameter, at most about 1.25 cm in diameter, at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 0.5 cm in length along the longest length of the balloon, at most about 0.75 cm in length along the longest length of the balloon, at most about 1 cm in length along the longest length of the balloon, at most about 1.25 cm in length along the longest length of the balloon, at most about 1.5 cm in length along the longest length of the balloon, at most about 1.75 cm in length along the longest length of the balloon, at most about 2 cm in length along the longest length of the balloon, at most about 2.25 cm in length along the longest length of the balloon, at most about 2.5 cm in length along the longest length of the balloon, at most about 2.75 cm in length along the longest length of the balloon, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in diameter, at most about 4.25 cm in diameter, at most about 4.5 cm in diameter, at most about 4.75 cm in diameter, at most about 5 cm in diameter, at most about 5.25 cm in diameter, at most about 5.5 cm in diameter, at most about 5.75 cm in diameter, at most about 6 cm in diameter, at most about 6.25 cm in diameter, at most about 6.5 cm in diameter, at most about 6.75 cm in diameter, at most about 7 cm in diameter, at most about 7.25 cm in diameter, at most about 7.5 cm in diameter, at most about 7.75 cm in diameter, at most about 8 cm in diameter, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in length along the longest length of the balloon, at most about 4.5 cm in length along the longest length of the balloon, at most about 4.75 cm in length along the longest length of the balloon, at most about 5 cm in length along the longest length of the balloon, at most about 5.25 cm in length along the longest length of the balloon, at most about 5.5 cm in length along the longest length of the balloon, at most about 5.75 cm in length along the longest length of the balloon, at most about 6 cm in length along the longest length of the balloon, 6.25 cm in length along the longest length of the balloon, at most about 6.5 cm in length along the longest length of the balloon, at most about 6.75 cm in length along the longest length of the balloon, at most about 7 cm in length along the longest length of the balloon, at most about 7.25 cm in length along the longest length of the balloon, at most about 7.5 cm in length along the longest length of the balloon, at most about 7.75 cm in length along the longest length of the balloon, and at most about 8 cm in length along the longest length of the balloon. As used herein with respect to balloon dimensions whether length or diameter, the term "about" means variations of at least one of 0.1 cm, 0.2 cm, 0.25 cm, 0.5 cm, and 1 cm.

Thus, provided herein is an implant configured to patch osteochondral defects. The defects may occur due to injury, stress, naturally occurring, and/or may created or enhanced by a medical professional during a medical procedure. In some embodiments, the implant may be called a patch having the balloon and an attachment element (or elements—which may be called appendages) described herein and may be sized to fit within a defect in a manhole-cover type manner. In some embodiments, the implant may comprise balloon and attachment elements described elsewhere herein and may be configured to lay over a defect (full defect or partial defect). In some embodiments the implant as described herein as used to patch or repair osteochondral defects may be called a patch or a patch implant.

In some embodiments, the size of the balloon dimensions are prechosen based on the individual patient need, and the balloon size (dimensions, geometry, length, depth, for non-limiting examples) is pre-set. In some embodiments, the balloon comprises multiple chambers which may be inflated (or deflated) selectively to fill the defect in situ or just prior to implantation in order to adjust the implant's balloon size (dimensions, length, width, depth, geometry, for non-limiting example) as needed at the time of implantation. The balloon (or any chamber thereof) of some embodiments can be secondarily inflated or deflated (or both) in situ.

FIGS. 11A, 11B, and/or 11C may be used to describe a patch implant described herein, having appendages 4 *a*, 4 *c*, extending from a balloon 6 (not shown in FIG. 11A) and including holes 8 *a*-8 *h*, and/or tabs 10 *a*-10 *f* which may be used with couplers (not shown) to couple the implant to a bone of the knee joint (which may be the femur, the tibia, or the patella). Features shown in FIGS. 11A, 11B, and/or 11C are common to both the unicompartment knee implant (discussed elsewhere herein) and the patch implant, although dimensions may differ as described herein. Thus, FIGS. 11A, 11B, and/or 11C may be used to describe the unicompartment knee implant and/or the patch implant. FIG. 11A depicts an embodiment of the patch implant 2 curved to simulate curvature about one condyle of a femur, the implant 2 having appendages 4 *a*, 4 *c*, extending from an uninflated balloon (not shown) and including tabs 10 *a*-10 *f* and/or holes 8 *a*-8 *h*, which may be used with couplers (not shown, described elsewhere herein) to couple the implant 2 to the femur of the knee joint. FIG. 11B depicts an embodiment of the patch implant 2 curved to simulate curvature about one condyle of a femur, the implant 2 having appendages 4 *a*, 4 *c*, extending from an inflated balloon 6 and including tabs 10 *a*-10 *f* and/or holes 8 *a*-8 *h*, which may be used with couplers (not shown, described elsewhere herein) to couple the implant 2 to the femur of the knee joint. FIGS. 11A and 11B show the appearance of a compliant solid material for unicompartmental implantation. FIG. 11C depicts a bottom-up of gliding surface view of an embodiment of the patch implant 2 curved to simulate curvature about one condyle of a femur, the implant 2 having appendages 4 *a*, 4 *c*, extending from an inflated balloon 6 or a padded central area of the implant and including tabs 10 *a*-10 *f* and/or holes 8 *a*-8 *h*, which may be used with couplers (not shown, described elsewhere herein) to couple the implant 2 to the femur of the knee joint. In some embodiments, the implant is configured to couple to a tibia. In some embodiments, the implant is configured to couple to a trochlear groove of a femur. In some embodiments, the implant is configured to couple to only a portion of a condyle of a femur.

FIGS. 12A, 12B, and/or 12C may be used to describe a patch implant described herein, having appendages 4 *a*, 4 *c*, extending from a balloon 6 and including holes 8 *a*, 8 *b*, 8 *c* prefabricated into an uninflated area, and/or tabs 10 *a*, 10 *b*, 10 *c*, 10 *d*, 10 *e*, 10 *f* which may be used with couplers (not shown) to couple the implant to a bone of the knee joint (which may be the femur, the tibia, or the patella). Features shown in FIGS. 12A, 12B, and/or 12C are common to both the unicompartment knee implant (discussed elsewhere herein) and the patch implant, although dimensions may differ as described herein. Thus, FIGS. 12A, 12B, and/or 12C may be used to describe the unicompartment knee implant and/or the patch implant. FIG. 12A depicts a bottom-up view of an embodiment of the implant 2 (unicompartment or patch), the implant having appendages 4 *a*, 4 *c*, extending from a balloon 6 and including holes 8 *a*, 8 *b*, 8 *c*, which may be used with couplers (not shown) to couple the implant 2 to the femur of the knee joint. FIG. 12B depicts a bottom-up view of an embodiment of the implant 2 (unicompartment or patch), the implant having appendages 4 *a*, 4 *c*, extending from a balloon 6 and including tabs 10 *a*, 10 *b* and hole 8 *a* which may be used with couplers (not shown) to couple the implant to the femur of the knee joint. FIG. 12C depicts a bottom-up view of an embodiment of the implant 2 (unicompartment or patch), the implant having appendages 4 *a*, 4 *c*, extending from a balloon 6 or padded weight bearing region of the implant and including tabs 10 *c*, 10 *d*, 10 *e*, and 10 *f* and hole 8 *a* which may be used with couplers (not shown) to couple the implant to the femur of the knee joint. In some embodiments, the implant is configured to couple to a tibia. In some embodiments, the implant is configured to couple to a trochlear groove of a femur. In some embodiments, the implant is configured to couple to only a portion of a condyle of a femur. In some embodiments the implant is coupled to the patella. In any embodiment the balloon 6 may extend from one surface of the implant as a focal protuberance to fill a defect, space, or to aide in alignment correct, or the balloon may be full thickness as differences in FIGS. 2 and 3 show respectively. In any embodiment there may be a singular or multiple major balloons, if off a primary surface resembling bubble wrap, and there may be microscopic balloons or vacuoles containing gas, gel, or solid in the material matrix.

In all descriptions provided herein of the patch implant, the implant may instead be configured to couple to the tibia or to the fibula or the patella. It is the intention and understanding that the implant is suited for this purpose in certain embodiments with adjustments to account for dimensional differences of these bones. Most descriptions provided herein are directed to embodiments coupling the implant to the femur, however, this is primarily for ease of description and continuity, and does not preclude embodiments wherein the implant is coupled to the tibia (or other bones). Likewise, as noted elsewhere herein, there are embodiments where the implant may be coupled to two bones (at least), for example to both a tibia and a femur.

Partial Knee Arthroplasty (Unicompartment)

In addition to the total knee-type (dual condyle) and patch implants are implants that serve to cover and adjust alignment for either the medial or lateral condyle of the femur with varus or valgus knees requiring added cushioning to recreate the natural six degrees of knee valgus.

Thus, provided herein is an implant for placement on at least one condyle of the distal femur (a unicompartment implant—named so due to their coverage of a single condyle of the femur). The implant may be configured to be placed over the lateral condyle. The implant may be configured to be placed over the medial condyle. The implant may be configured to be placed over either the medial condyle or the lateral condyle. Two unicompartment implants may be placed in the same knee, one over the medial condyle, one over the lateral condyle.

FIGS. 11A-12C depict example embodiments of unicompartment implants. In some embodiments, the unicompartment implant comprises a balloon that is at least one of: at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 4 cm in diameter, at most about 4.25 cm in diameter, at most about 4.5 cm in diameter, at most about 4.75 cm in diameter, at most about 5 cm in diameter, at most about 5.25 cm in diameter, at most about 5.5 cm in diameter, at most about 5.75 cm in diameter, at most about 6 cm in diameter, at most about 6.25 cm in diameter, at most about 6.5 cm in diameter, at most about 6.75 cm in diameter, at most about 7 cm in diameter, at most about 7.25 cm in diameter, at most about 7.5 cm in diameter, at most about 7.75 cm in diameter, at most about 8 cm in diameter, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in length along the longest length of the balloon, at most about 4.5 cm in length along the longest length of the balloon, at most about 4.75 cm in length along the longest length of the balloon, at most about 5 cm in length along the longest length of the balloon, at most about 5.25 cm in length along the longest length of the balloon, at most about 5.5 cm in length along the longest length of the balloon, at most about 5.75 cm in length along the longest length of the balloon, at most about 6 cm in length along the longest length of the balloon, 6.25 cm in length along the longest length of the balloon, at most about 6.5 cm in length along the longest length of the balloon, at most about 6.75 cm in length along the longest length of the balloon, at most about 7 cm in length along the longest length of the balloon, at most about 7.25 cm in length along the longest length of the balloon, at most about 7.5 cm in length along the longest length of the balloon, at most about 7.75 cm in length along the longest length of the balloon, and at most about 8 cm in length along the longest length of the balloon. As used herein with respect to balloon dimensions whether length or diameter, the term "about" means variations of at least one of 0.1 cm, 0.2 cm, 0.25 cm, 0.5 cm, and 1 cm.

In some embodiments, the implant comprises attachment tabs or attachment elements over the anterior and/or posterior and/or medial side, and/or lateral side (and/or some combination thereof) of a condyle. In some embodiments, the implant comprises attachment tabs or attachment elements in the intercondylar notch. In some embodiments, the implant comprises attachment tabs or attachment elements superiorly at the distal end of the femur anteriorly.

The posterior of the knee can be difficult to access without disturbing joint components (or in order to minimize such disturbance) such as tendons, ligaments, etc. Thus, in some embodiments, the implant comprises strings, reigns, lassos, and/or lanyards that may pass from the posterior of the implant via the intercondylar notch anteriorly to join with themselves and/or other coupling devices. In some embodiments, posterior reigns or suture-like lanyards cinch up the implant from inside the posterior intercondylar notch toward another connection site around the femur. These couplers may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is pre-molded, the coupler as described are adapted to move the implant to its final position with conformity to the condyle's posterior with minimal disturbance to the joint structures at the joint's posterior (minimal cutting, minimal moving, and or minimal detachment, for non-limiting example). In some embodiments at least a portion of the ligamentary structure of the knee is spared.

FIG. 10A depicts a side view of an embodiment of the knee implant 20 curved about at least one condyle 22 of a femur 24, the implant 20 having appendages 4 b, 4 d extending from an inflated balloon 6 and showing the inflation medium 46 moved anteriorly toward the patella 40 when the knee joint is slightly flexed. Likewise, FIG. 10B depicts a side view of an embodiment of the knee implant 20 curved about at least one condyle 22 of a femur 24, the implant 20 having appendages 4 b, 4 d extending from an inflated balloon 6 and having couplers 44 a, 44 b (which may be, for non-limiting example, staples or screws, pins or snaps) coupling the appendages 4 b, 4 d to the femur 24 and showing the inflation medium 46 moved anteriorly toward the patella 40 when the knee joint is slightly flexed.

FIGS. 11A, 11B, and/or 11C may be used to describe a unicompartment implant 2 (or unicompartment knee implant, terms which may be used interchangeably) described herein, having appendages 4 a, 4 c, extending from a balloon 6 (not shown in FIG. 11A) and including holes 8 a-8 h, and/or tabs 10 a-10 f which may be used with couplers (not shown) to couple the implant to a bone of the knee joint (which may be the femur, the tibia, or the patella). Features shown in FIGS. 11A, 11B, and/or 11C are common to both the unicompartment knee implant and the patch implant (discussed elsewhere herein), although dimensions may differ as described herein. Thus, FIGS. 11A, 11B, and/or 11C may be used to describe the unicompartment knee implant and/or the patch implant. FIG. 11A depicts an embodiment of the unicompartment knee implant 2 curved to simulate curvature about one condyle of a femur, the implant 2 having appendages 4 a, 4 c, extending from an uninflated balloon (not shown) and including tabs 10 a-10 f and/or holes 8 a-8 h, which may be used with couplers (not shown, described elsewhere herein) to couple the implant 2 to the femur of the knee joint. FIG. 11B depicts an embodiment of the unicompartment knee implant 2 curved to simulate curvature about one condyle of a femur, the implant having appendages 4 a, 4 c, extending from an inflated balloon 6 and including tabs 10 a-10 f and/or holes 8 a-8 h, which may be used with couplers (not shown, described elsewhere herein) to couple the implant 2 to the femur of the knee joint. FIG. 11C depicts a bottom-up view of an embodiment of the unicompartment knee implant 2 curved to simulate curvature about one condyle of a femur, the implant 2 having appendages 4 a, 4 c, extending from an inflated balloon 6 and including tabs 10 a-10 f and/or holes 8 a-8 h, which may be used with couplers (not shown, described elsewhere herein) to couple the implant 2 to the femur of the knee joint.

In some embodiments, the unicompartment implant including attachment tabs is at least one of: at most about 15 cm in length along the longest length of the implant, at most about 15.25 cm in length along the longest length of the implant, at most about 15.5 cm in length along the longest length of the implant, at most about 15.75 cm in length along the longest length of the implant, at most about 16 cm in length along the longest length of the implant, at most about 16.25 cm in length along the longest length of the implant, at most about 16.5 cm in length along the longest length of the implant, at most about 16.75 cm in length along the longest length of the implant, at most about 17 cm in length along the longest length of the implant, at most about 17.25 cm in length along the longest length of the implant, at most about 17.5 cm in length along the longest length of the implant, at most about 17.75 cm in length along the longest length of the implant, at most about 18 cm in length along the longest length of the implant, 18.25 cm in length along the longest length of the implant, at most about 18.5 cm in length along the longest length of the implant, at most about 18.75 cm in length along the longest length of the implant, at most about 19 cm in length along the longest length of the implant, at most about 19.25 cm in length along the longest length of the implant, at most about 19.5 cm in length along the longest length of the implant, at most about 19.75 cm in length along the longest length of the implant, at most about 20 cm in length along the longest length of the implant, at most about 20.25 cm in length along the longest length of the implant, at most about 20.5 cm in length along the longest length of the implant, at most about 20.75 cm in length along the longest length of the implant, at most about 21 cm in length along the longest length of the implant, at most about 21.25 cm in length along the longest length of the implant, at most about 21.5 cm in length along the longest length of the implant, at most about 21.75 cm in length along the longest length of the implant, at most about 22 cm in length along the longest length of the implant, at most about 22.25 cm in length along the longest length of the implant, at most about 22.5 cm in length along the longest length of the implant, at most about 22.75 cm in length along the longest length of the implant, at most about 23 cm in length along the longest length of the implant, 23.25 cm in length along the longest length of the implant, at most about 23.5 cm in length along the longest length of the implant, at most about 23.75 cm in length along the longest length of the implant, at most about 24 cm in length along the longest length of the implant, at most about 24.25 cm in length along the longest length of the implant, at most about 24.5 cm in length along the longest length of the implant, at most about 24.75 cm in length along the longest length of the implant, at most about 25 cm in length along the longest length of the implant, at most about 25.25 cm in length along the longest length of the implant, at most about 25.5 cm in length along the longest length of the implant, at most about 25.75 cm in length along the longest length of the implant, and at most about 26 cm in length along the longest length of the implant. As used herein with respect to implant length dimensions, the term "about" means variations of at least one of 0.1 cm, 0.2 cm, 0.25 cm, 0.5 cm, and 1 cm.

In some embodiments, the unicompartment implant is longer than it is wide, and the longer portion of the implant wraps from the anterior of the condyle to the posterior of the condyle. In some embodiments, the length of the implant is longer on the outer edge of the implant than on the inner edge nearest the trochlear groove (whether used on the lateral or medial condyle). In some embodiments, the trochlear groove per se rather than either the medial or lateral compartment is reconstructed with the implant anatomically to oppose the undersurface of the patella.

FIGS. 12A, 12B, and/or 12C may be used to describe a unicompartment knee implant (unicompartment implant) described herein, having appendages 4 a, 4 c, extending from a balloon 6 and including holes 8 a, 8 b, 8 c, and/or tabs 10 a, 10 b, 10 c, 10 d, 10 e, 10 f which may be used with couplers (not shown) to couple the implant to a bone of the knee joint (which may be the femur, the tibia, or the patella). Features shown in FIGS. 12A, 12B, and/or 12C are common to both the unicompartment knee implant and the patch implant (discussed elsewhere herein), although dimensions may differ as described herein. Thus, FIGS. 12A, 12B, and/or 12C may be used to describe the unicompartment knee implant and/or the patch implant. FIG. 12A depicts a bottom-up view of an embodiment of the implant 2 (unicompartment or patch), the implant having appendages 4 a, 4 c, extending from a balloon 6 and including holes 8 a, 8 b, 8 c, which may be used with couplers (not shown) to couple the implant 2 to the femur of the knee joint. FIG. 12B depicts a bottom-up view of an embodiment of the implant 2 (unicompartment or patch), the implant having appendages 4 a, 4 c, extending from a balloon 6 and including tabs 10 a, 10 b and hole 8 a which may be used with couplers (not shown) to couple the implant to the femur of the knee joint. FIG. 12C depicts a bottom-up view of an embodiment of the implant 2 (unicompartment or patch), the implant having appendages 4 a, 4 c, extending from a balloon 6 and including tabs 10 c, 10 d, 10 e, and 10 f and hole 8 a which may be used with couplers (not shown) to couple the implant to the femur of the knee joint.

In all descriptions provided herein of the unicompartment implant, the implant may instead be configured to couple to the tibia or to the fibula or the patella. It is the intention and understanding that the implant is suited for this purpose in certain embodiments with adjustments to account for dimensional differences of the particular bones. Most descriptions provided herein are directed to embodiments coupling the implant to the femur, however, this is primarily for ease of description and continuity, and does not preclude embodiments wherein the implant is coupled to the tibia (or other bones). Likewise, as noted elsewhere herein, there are embodiments where the implant may be coupled to two bones (at least), for example to both a tibia and a femur.
Meniscal Replacement or Repair, and Solid, Rigid, or Semi-Rigid Components:

Provided herein is an implant having a balloon having a first and second chamber. The implant may be any of the Dual Compartment, Unicompartment, and Patch implants described herein. The second chamber may be configured to replace and/or partially replace fibrocartilage meniscal loss. The implant may have two lobes of chambers which may be alternatively described as two superimposed balloon radii in apposition to each other. The implant may be configured to provide stability between the femur and tibia by providing a meniscus wedge. In some embodiments the implant comprises a portion configured to replace and/or partially replace fibrocartilage meniscal loss. Such an embodiment may not require a second chamber.

In some embodiments a chamber of the implant is configured to receive a solid piece configured to restore joint and/or bone alignment. In some embodiments, the chamber is configured to receive a plurality of solid pieces, each of which can be used to increase the space between a first bone and a second bone in order to restore and/or improve joint and/or bone alignment. The solid pieces may be wedge-shaped, or be provided in various sizes and/or shapes. The solid pieces may individually or together be used in a chamber or multiple chambers of the implant. The solid piece (or pieces) may be used to ratchet adjacent bones to a desired distraction and/or alignment to restore and/or improve joint and/or bone alignment. The solid piece may be put in a chamber of the implant, which may enclose or partially enclose the piece to hold the piece in place. In some embodiments, a block of biocompatible material (such as PMMA or another bone-like substitute) may be provided and may be formed (by carving or other forming method) by the surgeon to a desired shape. The formed piece may then be put in a chamber of the implant, which may enclose or partially enclose the piece to hold the piece in place.

In some embodiments, the inflation medium is a methyl methacrylate or other biocompatible hardening substance which can flow when initially put into the chamber, and hardens to become a rigid piece (or solid piece). The methyl methacrylate or other biocompatible hardening substance may conform to the shape of the chamber, or may conform to the shape of a space between bones and/or other joint structures. The methyl methacrylate or other biocompatible hardening substance may conform to a form chosen by the surgeon using tools and/or pressure to influence the final shape of the rigid piece formed by the methyl methacrylate or other biocompatible hardening substance upon hardening.

The solid piece (whether formed in situ or by a surgeon or pre-formed) may be cushioned by the implant. The implant may comprise an inflatable chamber between the solid piece and the first bone. In some embodiments, the first bone is a femur. The implant may comprise an inflatable chamber between the solid piece and the tibia. The implant may comprise an inflatable chamber between the solid piece and the patella. The implant may comprise an inflatable chamber between the solid piece and the second bone. The implant may comprise a pad between the solid piece and the first bone as a cushion. In some embodiments, the first bone is a femur. The implant may comprise a pad between the solid piece and the second bone as a cushion. In some embodiments, the second bone is a tibia. In some embodiments, the second bone is a patella.

The solid piece may provide at least one of about 1 degree of joint correction, about 2 degrees of joint correction, about 3 degrees of joint correction, about 4 degrees of joint correction, about 5 degrees of joint correction, about 6 degrees of joint correction, about 7 degrees of joint correction, about 8 degrees of joint correction, about 9 degrees of joint correction, and about 10 degrees of joint correction.

With respect to degrees of joint correction, the term "about" can mean ranges of 1%, 5%, 10%, 25%, or 50%.

The implant can be used in a variety of joints where the implant replaces a bone on bone surface and cushions the interaction between the articular ends of any two bones, such as at the femoral tibial and patella femoral knee interfaces. The implant can be used in a variety of joints where the implant replaces a bone on bone surface and cushions the interaction between the articular ends of any two bones, such as at the femoral-acetabular interspace of a patient's hip, the humerus and glenoid scapular component in the shoulder, the replacement of talus bone in the human ankle between the tibia and calcaneus and the like. Where the implant is substituting or enhancing articular cartilage, the rigidity can be reduced or enhanced to maximize conformation changes that arise during motion as enabled by the two opposing walls and intended inner space, coupled with considerations in any joint surgical reconstruction with accommodation to or amplification of the existing joint ligaments, tendons or dearth thereof. The implant 10 may be deflated and removed by minimally invasive surgery, for example, after the implant has served its purpose of regenerating tissue or if another clinical condition warrants its removal. However, it may not be clinically necessary to remove the implant even if inflation is lost, since the two remaining functions of patching the injured cartilage, and delivering restorative cells may justify implant retention.

In many embodiments the implant (or a portion thereof, such as the balloon or balloon) is a weight bearing spacer that allows joint motions to approach normal, whether filling the space left by an entirely collapsed peripheral joint bone or the space of ablated cartilage proximate surfaces diffusely as in osteoarthritis or succinctly as in osteonecrotic defects or localized trauma. The walls may be used as a membrane for holding living cells in proximity of the osteochondral defect long enough for the cells to attach (e.g. 24 hours) or to deeply adhere (up to 28 days) or return to normal (up to one year). Weight bearing may be expected to increase as distal lower extremity joints are treated.

Additional Locations for Use

Shoulder subacromical bursa may be a target joint for an implant as described herein. Rotator cuff tears may be addressed using an implant as described herein—as adjusted for the particular features, loading profile, and geometries of the joint. In shoulders, 85% of octagenians have massive rotator cuff tears and often less than half normal upper extremity abduction and flexion capabilities. There may not be sufficient remnant supraspinatus and other rotator cuff tissues to pull together. Then the humeral head rides up, in a cephalad direction, rubbing the superior bone surface on a frequently spurred and downward sloping acromion. If a subacromial implant as described herein were implanted beneath the lateral (arthroscopically decompressed and prepared) acromion, the pain of bone on bone could be reduced, and the structural anatomy between the ball and socket (humeral head and glenoid fossa) could be improved. In essence then a shoulder implant could cover the humeral head analogous to the hip redundant membrane wherein that membrane replaces a normal subacromial bursa. Optionally, a singular bladder beneath the acromion per se could pad the ball beneath it. For virtually every joint in the body (arms and legs, at least) there are similar potential implant uses.

The distal femur of the knee, and the distal humerus of the elbow are regions that interface each with two opposite joints. That is, an implant for the knee as designed with polymer capping of the femoral condyles and trochlear groove to provide cushioning of the femorotibial and patellafemoral joints. Analogously, in the humerus the distal coverage enables padding restoration of the humeral-olecranon as well as the radio-capitellar (part of the humerus) joint interfaces. Whereas generally the implant may cover the main or primary joint surface of the surgeon's choice contributing to arthritis, consequently reducing symptoms when treated, another alternative would be that the implant can cover any singular surface entirely or partially. It is generally desired that the implant may cover one surface allowing remnant cartilages in other usually opposing or opposite surfaces to glide against the implant polymer with smooth gliding joint motion. This principle allows for retained joint linings or synovium to produce lubricating substances including enzymes for facile joint movement. It also avoids the wear debris that would accrue from polymer rubbing on polymer, as recently recognized in metal on metal prostheses. In certain embodiments, the implant can cover more than one surface in a joint, such as the radio-capitallar joint wherein the distal humerus and the radial head receive prosthetic capping or interpositional application of polymers.

The surgical techniques may be individualized to fit patient need. The implants may be combined with or comprise autologous or allograph tissues such as fascia lata. Surgeons may implant fascia lata above unreconstructable rotator cuff with consequent symptom relief. Polymers can interface with any human tissue and/or with metals or polyethylenes or polyurethanes. Living tissues that can be combined with implants provided herein for repair or reconstruction may be from the same patient (autograph), and cadaver or other member of the same species (allograph) or from another species (xenograph.) Virtually any combination of polymer interpositioning is feasible with the implant concepts provided herein, as anatomy varies among patients in need, and clinical conditions differ with each person. Therefore, although the general or most common construct is expected to cover just one singular and the primary surface of a joint with an implant, any combination of surfaces can be involved allowing versatile custom applications of this implant and method of surgery.

Additionally, whereas implants as noted herein may be available in specified sizes, the material membrane elastic deformation and resilience may allow for calculated malleability toward goodness of fit. In other iterations the fit of implant over the affected joint surface is customized as paring preoperative findings of MRI or CT or PET imaging pathophysiology with intraoperative reconstructive need. Ultimately best fit implants may serve patient restorative requirement with least morbidity.

Locations wherein implants described herein may be additionally or alternatively applicable include all the limb joints of mammals. In the shoulder mainly the glenohumeral joint, though as discussed above the subacromial space are useful loci for renewed padding when pathophysiologies warrant. In the AC or acromioclavicular joint of the shoulder, a Mumford procedure (resection of the distal clavicle) can be avoided by inserted an implant as described herein. Even the TMJ in the jaw may be amenable to therapy using the implants noted herein. Proceeding distally in the aim, the elbow has two relevant joints mentioned earlier, radiocapitellar and ulnohumeral. Depending on 'where the arthritis forms' (as from fracture or disease) the padding should be restored toward normal. Wrist, thumb and finger joints are many and may respond to vesicular implants with better durometry and vicsolubricant delivery than tradition metal or silicon prostheses. Legs started at the hip joint have been shown via Hip implant prototypes to be amenable to polymer capping. Variations per surgeon's choice could evoke special uses as for coverage of trochanteric bursae.

Additionally, the many functions of the implants noted herein may be coupled with cosmetic aspects in order to restore bulk and soft tissue balance after scarring, injury or atrophy, or for purely cosmetic purposes. Treatment for cosmesis especially when coupled with functional or visual injury deficits can provide a reduction in physiological as well as physical pain and discomfort. Therefore the extent minimally invasive implants restore the injured or diseased patient recipient to become hole, they are being used purposefully and as intended.

The knee joint is an initial focus of the figures wherein application to the largest bone (the distal femur) accommodates padding needs for the opposing patella and tibia. The potential use of implants, however, over the contralateral surfaces is an option that should not be ruled out. In the ankle the supratalar, or tibia talar joint will be a useful location as may the subtalar area, depending on pathology present. Indications for use may depend on the patients symptoms, from the history and physical exam, based on studies such as roentgenograms, MRI or CT imaging, and may depend on test result from localized injections. For example, if a talus fracture pain were alleviated by sinus tarsi injection then implant insertion into the subtalar joint would be preferred. The talonavicular and other foot/toe joints are all amenable to renewed padding via an implant noted herein.

Pets, or other animals, such as cows, dogs, and horses, may be served better by polymer joint capping than hip replacement for congenital dysplasia. The successful treatment and rehabilitation of animals can favorably affect the implant recipient and animal's owner, as pets can provide functions necessary for activities of daily living (as a horse helping to plow a field) or an animal relieved of pain from injury or arthritis can also be a comfort to its owner.

Kits

Provided herein are kits comprising multiple implants described herein. A kit may comprise multiple sizes of a single type of implant. A kit may comprise various implant types, such as the patch, the unicompartment, and/or the dual compartment types of implants described herein. A kit may comprise various couplers, which may be selected by the surgeon depending on his comfort and expertise, and/or based on the particular patient anatomy and/or needs. The kit may further comprise any insertion tools and/or surgery tools that may uniquely assist in implanting the implant in the patient.

In addition to kits involving reparative implants, and insertional tools, there may also be included software for translation of pre-injury data and/or postoperative data collection and analysis, as well as custom implants may be provided.

Implantation Methods

Implantation of implants provided herein may depend on the size of joint surface intended for reconstruction by use of the implant. This may be based upon the nature and extent of injury, and upon the expectations of the patient and surgeon. In some embodiments, an arthroscope can be inserted in one side of the knee joint through a 0.5 cm wound, while the implant is inserted into the opposite joint line wound from 1-10 cm in size. The joint may be first inspected and debrided, performing an arthroscopic synovectomy, chondroplasty, and meniscectomy as needed. Additional distraction under general anesthesia with the knee at variable degrees of flex may allow for implant introduction, systematic peripheral attachment, balancing, and inflation, if warranted.

In some embodiments, the implant may be selectively inflatable depending on the particular needs of the patient. In some embodiments, the filler of the interior of the implant may be rigid, semi-rigid, fluid, air, or combinations thereof, as described herein. In some embodiments, the implant may be used in conjunction with fibrocartilage repair or replacement. In some embodiments, the implant may be used without fibrocartilage repair or replacement. In some embodiments, the implant may be used in conjunction with boney osteotomy. In some embodiments, the implant may be used without boney osteotomy.

The posterior of the knee can be difficult to access without disturbing joint components (or in order to minimize such disturbance) such as tendons, ligaments, etc. Thus, in some embodiments, the method comprises providing an implant comprising strings, reigns, lassos, and/or lanyards that may pass from the posterior of the implant via the intercondylar notch anteriorly to join with themselves and/or other coupling devices. In some embodiments, posterior reigns or suture-like lanyards cinch up the implant from inside the posterior intercondylar notch toward another connection site around the femur. In some embodiments, the methods comprise conforming the implant posterior to the condyle by pulling the strings (or reigns, or lassos, or lanyards or the like) of the implant. Such couplers (strings, reigns, lassos, lanyards, etc) may comprise suture materials and/or wire materials.

These couplers (i.e. strings, reigns, lassos, lanyards, etc) may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is premolded, the coupler as described are adapted to move the implant to its final position with conformity to the condyle's posterior with minimal disturbance to the joint structures at the joint's posterior (minimal cutting, minimal moving, and or minimal detachment, for non-limiting example). In some embodiments at least a portion of the ligamentary structure of the knee is spared.

In some instances, the implant is inserted arthroscopically through a cannula about 10 mm in diameter with the implant in the deflated construct, and once inside the prepared joint space and secured therein by the skirt or tabs, the implant is distended or inflated with gas, gel, fluid or fluid that becomes a resilient solid to fill the original natural space of about 0.5 cm between the bones of the joint (between at least two bones of the joint). If the implant is not inserted through a cannula, it may be inserted through an open incision from one to forty centimeters in length at the surgeon's discretion. Tensioning may be by the surgeon's sense of proper pressure application aided by a gauged syringe for insertion of viscolubricants such as Synvisc, Hyalgan, Supartz and/or analgesics such as lidocaine gel. The insertion of liquids to the joint per se may be directly, through a cannula to the joint space previously in place for debridement, and or via a cannula or tube that is not part of the original implant assembly. Once the joint is cleaned, the implant is inserted and appropriately fixed to avoid extrusion or dislocation thereof. This may be via attachment of the implant tabs and/or by a combination of tab use plus intended friction created by implant surface coverings (analogous to Velcro) or a draw string at the smaller base of the implant.

In some embodiments the attachment tabs are positioned on the implant to both secure the implant to the joint components, and to enable a physician to ensure the implant has a minimum amount of slack that could create wrinkles or loose areas to avoid unnecessary friction and/or wear of the implant of the patient's anatomy. Figures depicted herein show examples of properly situated attachment tabs configured for these dual purposes. In some embodiments, fewer tabs are needed to achieve these goals.

In some embodiments, where slack or voids exist, the balloon under compression may fill such areas. The implant in some embodiments is configured to allow hyaline and/or cartilage cells to fill any irregularities or craters in the joint components and grow to refurbish natural joint contour. When the implant implantation is combined with, for example, movement of the treated joint in a constant passive motion machine for 12 hrs a day for 6 weeks after surgery implanting the implant, cell growth may create renewed hyaline cartilage, and/or blood/fibrin and scar to create fibrocartilage filler material.

Each attachment tab insert site may be clinically determined centripitally around the implant during surgery, driving slots or holes sequentially with an osteotome or drill immediately followed by insertion of the triangled tab extension into the bone slots or screw respectively. For example, if the implant were viewed like a clockface the first tab could be tacked/tapped in a 2 o'clock, then 7, 10, 4, 11, 5, 12, 6 (wherein #2, 7, 10, 4 are over the bilateral femurs superior/inferior to collateral ligaments, 11, 12 are superior at the distal anterior femur beneath the upper patella, and 5, 6 are inside the intercondylar notch anterior to cruciates). This can be like putting a saddle on a horse, going around the knee end with a grasper, to tug the polymer toward fit, tapping a slot over the side of the femur with a thin one-half inch osteotome, angling cuts distally, one by one, as if to pull the implant (or saddle) into its angle of repose, seating ideally over the condyles and ridings nicely in the trochlear groove.

In some embodiments, the metal clips could be set angled at about 120 degrees, as greater than 90 can favorably distract/hold the implant to tighter fit analogous to a mylar compliant balloon or stretch sock fitting over a protuberance as opposed to a piece of (non-compliant) paper that results is wrinkles and areas of incongruence between the implant and bone end. Reducing dislodgement tendency and snugging the polymer once stretched to best fit may avoid the failure history as illustrated in the Danish Polymer hip cap solid crescent shaped hip resurfacing implants which lacked inflation, surface stability, accommodation, and fixation.

Inflation may also be specified by clinical need, and modifications in the implant multi-cell (multi-compartment) construction allows for selective inflation with substances ranging from gas to solid, including gels or semi-solids that can as part of material layered integrity either provide calculated hardness (durometer) to overcome and resist limb adjacent bone mal-alignment, and/or to deliver new regenerative tissues for restoration of natural anatomy of time. That is, certain sections of the implant may be electively inflated of left without expansion, to adjust to fit as matching a normal or uninjured contralateral limb for the involved patient.

Indeed, patient interaction and feedback may be sought so as to bring to orthopedic conceived art and science the individual's own needs and concerns. It is said that for patients who have anterior cruciate injuries, one third require reconstruction for knee joint stabilizer, one third do not—living with a reduced activity level, and one third deliberate extensively until a choice between the two continuum options is made.

A goal of embodiments of implants described herein is to maintain remnant living tissue by using minimally invasive technologies, smaller incisions when they serve the patient equally to larger, sacrificing the least normal tissue as possible. Implants described herein assist and improve on current treatment options available by avoiding as much as possible the ablative bone and cartilage resecting, ligament removing total knee arthroplasty and instead to restore the padding lost in injury or disease or surgery.

Examples from within the techniques include electing to repair rather than reconstruct anterior cruciate ligaments in certain situations, proved warranted and effective at a $p<0.3$ statistical level. Whereas Carticel chondrocyte implantation is useful to enable articular surface regrowth with hyaline, rather than scar/fibrocartilage from picking/drilling, the massive morbidity from periosteal harvesting is unnecessary. This is because it takes only 24 hours for the cartilage cloned chondrocytes to attach to the prepared joint surface, and the polymer membrane (patch implant described herein, for example, or use of chondrocytes on surfaces of the dual compartment implant or the unicompartment implant) over the prepared defect (like a manhole cover) can adeptly substitute for periosteum.

With these concepts in mind in is the overall intent to do what is necessary to restore function and nothing more in order to spare the patient removal of injured tissues that may recover or regrow, by implementing a common sense approach to limb repair and reconstruction with the implant and methods of use thereof. In animals as horses and dogs, where recovery instructions are even less likely to be followed than with humans, implanting secure restorative implants for joint surface refurbishment may offer renewed function and save lives that would have otherwise been sacrificed.

Rehabilitation of knee implant treated patients may engage prudent early motion. The amount of weight bearing allowed may be analogous to the procedures written by this primary surgery for Carticel implanted cases, following the principles that excessive amounts and repetitions of stress upon reconstructed areas should be avoided for 6-12 weeks after surgery. However, the knee implant surgeries per se are expected to take less than one hour, involve less than 1 cc blood loss, require wounds less than or equal to 10 cm overall (depending on the embodiment of the implant), and the end result intends to permit early full weight bearing. Zealous sports activities may be restricted until the bone in-growth and cartilage renewal is reasonably expected, between 2 and 12 months after surgery depending upon the amount of joint tissue replaced.

In some situations, the removal of the implant may be needed, and embodiments of the implants described herein are configured for removal arthroscopically, and with the allowance to perform all regular older routine accepted techniques ranging from joint debridement to drilling, partial or total replacement. In some embodiments the implant is configured for removal and replacement with a replacement implant—either immediately (within a week), or after a period of longer time (for example, after about 6 weeks to 1 year in the case of infection once all foreign bodies are removed and depending upon the surgeon's and/or infectious disease consultant's opinion Specific surgical decisions related to size matching, fixation and or concomitant osteotomy warranted reconstruction are left to the primary surgeon and patient in each case.

The implant is inserted by minimally invasive surgery, in some embodiments; however, in other embodiments, the implant may not be inserted by minimally invasive surgery. In some embodiments, the implant is delivered through an incision that is about 0.5 inches long. In some embodiments, the implant is delivered through an incision that is about 1 centimeter long. In some embodiments, the implant is delivered through an incision that is at most about 1 inch long. In some embodiments, the implant is delivered non-arthroscopically through an incision that is at least 1 centimeter long. In some embodiments, the implant is delivered through an incision that is at most about 0.75 inches long. In some embodiments, the implant is delivered through an incision that is at most about 0.5 inches long. In some embodiments, the implant is delivered through an incision that is about 8 centimeters long. In some embodiments, the implant is delivered through an incision that is about 9 centimeters long. In some embodiments, the implant is delivered through an incision that is about 10 centimeters long. In some embodiments, the implant is delivered through an incision that is about 11 centimeters long. In some embodiments, the implant is delivered through an incision that is about 12 centimeters long. In some embodiments, the implant is delivered through an incision that is over about 10 centimeters long. In some embodiments, the implant is delivered through an incision that is at up to about 40 centimeters long. In some embodiments, the implant is delivered through multiple incisions. In some embodiments, the implant is delivered non-arthroscopically. In other embodiments, the implant is delivered arthroscopically. With respect to incision length, the term "about" can mean ranges of 1%, 5%, 10%, 25%, or 50%.

In some embodiments the implant is configured to be delivered to the joint arthroscopically. In some embodiments, the implant is configured to fit within a cannula having a distal end inner diameter of at most about 10 millimeters. In some embodiments, the implant is configured to fit within a cannula having a distal end inner diameter of at most about 9 millimeters. In some embodiments, the implant is configured to fit within a cannula having a distal end inner diameter of at most about 5 millimeters. With respect to cannula distal end inner diameter, the term "about" can mean ranges of 1%, 5%, 10%, 25%, or 50%.

In some embodiments, the implant is configured to fold in order to fit within a cannula having a distal end inner diameter of at most about 10 millimeters. In some embodiments, the implant is configured to fold in order to fit within a cannula having a distal end inner diameter of at most about 9 millimeters. In some embodiments, the implant is configured to fold in order to fit within a cannula having a distal end inner diameter of at most about 5 millimeters. With respect to cannula distal end inner diameter, the term "about" can mean ranges of 1%, 5%, 10%, 25%, or 50%.

In some embodiments, the implant is configured to be delivered to a joint through a cannula having a distal end inner diameter of at most about 10 millimeters. In some embodiments, the implant is configured to be delivered to a joint through a cannula having a distal end inner diameter of at most about 9 millimeters. In some embodiments, the implant is configured to be delivered to a joint through a cannula having a distal end inner diameter of at most about 5 millimeters. With respect to cannula distal end inner diameter, the term "about" can mean ranges of 1%, 5%, 10%, 25%, or 50%.

In some embodiments the implant may be provided as a deflated balloon for insertion into the joint space. In some embodiments the implant may be provided as folded balloon that may be collapsed like an umbrella for insertion into the joint space. In some embodiments the implant may be provided as collapsed balloon that is of an irregular folded pattern to minimize its folded (or collapsed) size for insertion into the joint space. In some embodiments, the implant is configured to blow up (or expand) to take the form of the expanded, distracted, debrided joint.

In some embodiments, the implant replaces periosteum.

In some embodiments, the implant is implanted to preserve bone as compared to a typical arthroplasty procedure of the joint. In some embodiments, the implant is implanted to preserve cartilage as compared to a typical arthroplasty procedure of the joint. In some embodiments, the implant is implanted with minimal soft tissue dissection as compared to a typical arthroplasty procedure of the joint. In some embodiments, the implant is implanted without joint dislocation. In some embodiments, once implanted, the joint is adaptable to revision surgery. In some embodiments once implanted, the joint retains at least one of: about 90% of normal joint function, about 95% of normal joint function, about 85% of normal joint function, about 80% of normal joint function, about 75% of normal joint function, about 70% of normal joint function, about 65% of normal joint function, about 60% of normal joint function, about 55% of normal joint function, about 50% of normal joint function, at least 95% of normal joint function, at least 90% of normal joint function, at least 85% of normal joint function, at least 80% of normal joint function, at least 75% of normal joint function, at least 70% of normal joint function, at least 65% of normal joint function, at least 60% of normal joint function, at least 55% of normal joint function, at least 50% of normal joint function, about 50%-about 75% of normal joint function, about 50%-about 70% of normal joint function, about 60-about 70% of normal joint function, about 70%-about 80% of normal joint function, about 70%-about 90% of normal joint function, about 80%-about 95% of normal joint function, about 80%-about 90% of normal joint function, and about 90%-about 95% of normal joint function. As used herein with respect to percentage of normal joint function, the term "about" can be ranges of 1%, 5%, 10%, or 25%. For example, a range of 1% with respect to about 90% of normal joint function covers 89% to 90% of normal joint function.

In an example of a hip implant, an upper portion of the implant has a first wall, a second wall and a side wall which define at least in part the interior. A skirt depends from the first wall and secures the first wall to the end of the patient's femur. An upper portion may be configured to engage the corresponding acetabulum of the patient's pelvic bone. The skirt surrounds the head of the patient's femur and secures the implant thereto. In this embodiment, the upper portion of the implant creates overlapping layers, like a redundant membrane, in the side wall between the first and second walls and to accommodate the normal movement of the first or second. This provides greater motion between the femur and the acetabulum and also provides implant stabilization over the head of the femur. This structure also accommodates variation in individual joints that occur from patient to patient.

In an embodiment, the first wall does not extend across the entire end of the patient's femur. However, the implant may be designed so that first wall may extend over the head of the femur. The second wall and the side wall tend to roll as the femur moves within the acetabulum.

In some embodiments, prior to deploying the implant embodying features of the invention, the cartilage lining the joint is prepared by removing hyaline or fibro cartilage flaps or tears, and areas of chondral advanced fissuring are excised or debrided to create precisely defined defects surrounded by stable normal remnant hyaline cartilage with vertical edges in relation to the damaged surface. It is these defects of the cartilage previously normal surface into which new living cells may be injected or otherwise inserted, and allowed to aggregate by the implant interpositional arthroplasty proximate expanded compressive external wall material. Synovitis invading the joint periphery may be vaporized and extracted conventionally or by the use of steam. Areas of greater cartilage damage are removed for subsequent regeneration and the less afflicted areas having stable cracks are treated to seal or weld the cracks. Areas where the tugor or consistency or minimally damaged cartilage can be preserved are intentionally saved rather than destroyed so as to support the normal spacing and gliding opportunity of the more normal joint interface. Thus, normal cartilage is left behind and abnormal cartilage is removed with the implant making up for the deficiencies. With the present invention, it is preferred in some embodiments to avoid joint dislocation so as to preserve natural innervations and vascularity and thus preserving the blood supply.

Joint preparation is usually performed under a brief general anesthetic of outpatient surgery. A muscle relaxant combined with traction (e.g. 60 pounds force for a hip implant) may be employed to opens the joint wider to permit improved visualization for joint preparation and implant installation, increasing the space between the remnant cartilage from about 3 up to about 12 mm. Increasing the joint space may be necessary and allows the surgeon to wash out noxious enzymes, to remove invasive synovitis, to remove loose bodies, to prepare osteochondral defects ideally and otherwise prepare the joint for the implant. Partial or complete inflation of the implant may precede release of traction in some embodiments. In some embodiments, regeneration agents or cells are inserted with the implant or as a fluid or 3-D template prior to release of traction and wound closure. It is preferred, in some embodiments, to perform joint debridement, implant deployment and application of cell regeneration agent, e.g. stem cell application, under the same anesthetic. As described by several companies in the Stem Cell Summit held in New York, N.Y. on Feb. 17, 2009, it is desirable to obtain an aspiration of the patient's bone marrow from the iliac crest after anesthesia sterilely at the beginning of the operation. The intraoperative technologist may "dial in the cells" to regenerate areas of maximum pathophysiology while the surgeon debrides or otherwise prepares the joint and inserts the implant, placing the cells at the best time. Cell implantation may also occur as a secondary or tertiary reconstructive treatment adjunct. An example resilient implant may be deployed within a patient's hip structure comprising the head of the patient's femur and the acetabulum of the patient's pelvic hip bone. The resilient implant embodying features of the invention is disposed within the space between the femur and the acetabulum. The implant is shaped like a half an orange rind or a hemisphere for a hip joint. The implant has a first wall which is secured to the head of the femur by a plurality of depending tabs (or appendages). The tabs may be attached to the femur by a suitable adhesive or mechanically such as by a screw or pin or snap. The second wall the implant engages the acetabulum, but it also may be provided with tabs and the like for securing the second wall the acetabulum.

The side wall extends between the first and second walls to form an interior which receives filling material through tube (also called a conduit herein, or may be called an inflation port). The implant would also be appropriate for the humeral head in the shoulder or one condyle of the knee or of the humerus, but other shapes may be desired for other joint configurations whether relatively flat as in the thumb base, or more inflated toward a ballooning construct as in the ankle when the talus bone is collapsed.

In many embodiments the implant (or a portion thereof, such as the balloon) is a weight bearing spacer that allows joint motions to approach normal, whether filling the space left by an entirely collapsed peripheral joint bone or the space of ablated cartilage proximate surfaces diffusely as in osteoarthritis or succinctly as in osteonecrotic defects or localized trauma. The walls may be used as a membrane for holding living cells in proximity of the osteochondral defect long enough for the cells to attach (e.g. motion is believed to be primarily between the spaced walls (or portions) of the implant peripherally secured to joint structures, although some motion may occur between the implant and the joint surfaces (as with current bipolar hip hemiarthroplasties)). The implant may be provided with a slot extending from the periphery of the implant to a centrally located passage through the implant to accommodate the ligament of the head of the femur for hip implants. Knee implants may have two slots leading to separate passages for receiving the anterior and posterior cruciate ligaments. Implants for other locations may have similar variable structures to accommodate anatomical features. Implant walls should have sufficient inherent flexibility to mold to the existing deformities imposed by either natural ligament, bone, tendon or remaining cartilage deformities of the internal joint space, and thus filled as a cushion. A separate portal or tube (not shown) or the existing conduit (tube or valve), may be used to extract noxious inflammatory enzymes that can be aspirated at appropriate clinical intervals. Viscolubricants can be injected into the interior of the resilient arthroplasty device through existing conduit or through a long needle to aide in distension, expansion, and/or lubrication (with predetermined microporosity).

The ankle version of the arthroplasty implant of the present invention comprises a square transverse cross-section that must take into account supratalar ankle dorsi/plantar flexion, subtalar eversion/inversion motions, ligament fixation-needs, and the accommodation to existing bony architecture as implant variables accounting for the ipsilateral joint pathophysiology. The implant has a first wall, a second wall and a side wall which extends between the first and second wall. The exterior of the implant may have a mesh material with a plurality of chords (or appendages) for securing the implant to adjacent bones or to remnant ligaments which are attached to adjacent bones.

The implant may be inflated with gas and/or liquid to open wider the space between the tibia above and the calcaneus below to accommodate collapse of the talus bone as in the flattening which succeeds talus fracture with avascular necrosis, or it may be filled with a liquid that becomes a resilient solid. The instant center of the implant's rotation will be constantly changing, with the talus implant mainly stable and with the tibia moving over it. Deformation with weight bearing during the average human's 10,000 daily steps or 2-4 million annual gait cycles required by the stance and walking of normal activities of daily living, must be balanced between sufficient solidarity of the implant to maintain axial load, avoiding circumferential stress, and shear forces imposed by the tibia distal plafond on the dorsal ankle implant allowing stance and gait of the patient while avoiding implant migration or failure. Further accommodation to lateral forces imposed by the boney medial and lateral malleoli need to be endured through the cyclic load of walking, while collapsing with enough give to absorb shock and to match the shape of surrounding structures of bone and ligament tissue. Whereas the axial load between the distal tibia through the talar implant to the dorsal calcaneus may be loaded during stance and especially while walking on a level plane for supratalar motion, the lateral forces may be loaded particularly with subtalar motion while walking on an uneven plane or with inversion/eversion.

In some embodiments, the first inflation medium imparts rigidity in the implant. In some embodiments, the first inflation medium imparts cushion in the implant. In some embodiments, the inflation medium chosen for the first inflation medium, and/or the particular choice of chamber (in embodiments having multiple chambers) filled with such first inflation medium aligns the joint. In some embodiments, the inflation medium chosen for the first inflation medium, and/or the particular choice of chamber (in embodiments having multiple chambers) filled with such first inflation medium aligns the bones of the joint. In some embodiments, the inflation medium chosen for the first inflation medium, and/or the particular choice of chamber (in embodiments having multiple chambers) filled with such first inflation medium changes the bone alignment. In some embodiments, the inflation medium chosen for the first inflation medium, and/or the particular choice of chamber (in embodiments having multiple chambers) filled with such first inflation medium improves joint alignment. In some embodiments, the inflation medium chosen for the first inflation medium, and/or the particular choice of chamber (in embodiments having multiple chambers) filled with such first inflation medium restores, at least in part, joint alignment. In some embodiments, individual chambers of the interior are selectively inflated with a first inflation medium and/or a second inflation medium. In some embodiments, individual chambers of the interior are selectively inflated with a first inflation medium and/or a second inflation medium in order to reconstruct the joint and/or bones of the joint.

In some embodiments, the interior comprises a honeycomb structure. In some embodiments, the interior comprises a mesh structure. In some embodiments, the interior comprises a sponge structure.

The dimensions of the various implant walls may vary depending upon the material properties thereof as well as the needs for a particular joint. The spacing between the first and second wall within the interior can vary from about 0.5 mm to about 5 mm for most joints (except for the implant for an ankle when an entire collapsed bone space is being replaced), preferably about one to five centimeters to fill between the tibia and calcaneus. In the ankle invention version of the implant, the amount of inflation of the implant per se may be directly proportional to the amount of talus bone collapse between the distal tibia and proximal calcaneus—thus as much as 5 cm implant distension or expansion may be required to be maintained between superior and inferior surfaces of the talus, while as much as 10 cm anterior and posterior expansion may be required for the ankle implant between the posterior soft tissues such including the Achilles tendon and the anterior navicular bone as relates to the talus.

The method of insertion for the hip joint invention may be a minimally invasive approach, ideally arthroscopically facilitated, as long as the surgical timing and result quality permit smaller incisions. The hip patient may be placed in the lateral decubitus position (lying non-operative side down on the operating table) with a stabilizing operating table pole and pad apparatus positioned to fix the pelvis. The external stabilizing table and attachments may include a padded metal pole beneath the pubis or pelvic bone from posterior to anterior, along with other external anterior and posterior pelvic stabilizing paddles. The affected leg may be attached beneath the knee with a distracting mechanism that applies about 60 pounds of distal force to open the hip joint about 1 cm once the patient is under general anesthesia. The hip joint is arthroscopically debrided through at least one anterior 0.5 cm incision and one posterior 0.5 cm incision, to remove from the femoral head acetabular (ball and socket) joint arthritic debris such as synovitis, loose bodies and noxious inflammatory enzymes. In certain cases a larger open incision may be needed. A smoothing or electronic/ultrasonic/steam or other chondroplasty method may be performed to make the remaining cartilage smoother to better accommodate the hip implant, and protuberant osteophytes or lateral bone overgrowths may be arthroscopically removed or if needed by open excision. A lateral hip incision may be required between 2 and 10 centimeters in length to deal with deformities and/or to insert the implant. In cases of major deformities appropriate reconstruction may add to the basic procedure.

Once the joint is open and cleared, the hip implant may be inserted laterally and fixed via the skirt or tabs or at least one appendage to the adjacent structures including the peripheral femoral head and/or acetabular rim. Preferably, the implant is inserted arthroscopically through a cannula about 10 mm in diameter with the implant in the deflated construct, and once inside the prepared joint space and secured therein by the skirt or tabs, the implant may be distended or inflated with gas, gel, fluid or fluid that becomes a resilient solid to fill the original natural space of about 0.5 cm between the upper acetabulum and lower femoral head, covering as much of the upper hip joint as required as the implant expands to fit the space.

The method of insertion of the ankle implant generally may be through an anterior surgical ankle approach or tendon separating incision from the distal tibia to the proximal talus (or calcaneus if the talus is absent), removing and reconstructing portions of the superior and inferior ankle extensor retinacula only to the extent required to gain access to the cleared tibiotalar space. Analogous to the hip joint insertional method, the ankle joint may be prepared arthroscopically under general anesthesia, and may benefit from distal distraction as in total ankle joint replacement surgeries with the DePuy Agility technique pinning above and below the ankle joint and then distracting it. The degree of distraction required in all joints to which this invention is applied, including but not limited to those of all appendicular skeletal structures such as the shoulder, elbow, wrist, phalanges, hip, knee, and ankle, may depend both on the nature anatomy and located pathophysiology that must be accommodated on a case by case basis and said distraction may be a combination of body position using gravitational forces and/or superimposed distracting devices. In the ankle, the surgeon may be developing the interval between the extensor hallucis longus and anterior tibial tendons. Injury tissue is removed, and the implant inserted fitting as preplanned. The implant surface may be provided with roughness, e.g. external mesh, to control movement by friction as described above for the hip joint, and/or attached fixation cords or tabs to connect to proximate ligaments or adjacent boney structures may be used at the surgeon's discretion to balance implant location stability and integrity, with the need for functional joint movements.

Provided herein is a method for restoring a joint comprising: providing an implant configured for deployment between a first bone and at least one second bone of a joint, the implant further comprising a balloon comprising a first portion that is configured to engage the first bone of the joint, a second portion that is configured to engage at least one second bone of the joint, a side portion connecting the first portion and the second portion, in which the side portion facilitates relative motion between the first portion and the second portion, and an interior that is optionally inflatable with a first inflation medium; and coupling a first appendage of the balloon to the first bone of the joint. In the case of a knee device, the first bone may be one of a tibia, a femur and a patella. In the case of a knee device, the second bone may be one of a tibia, a patella and a femur.

In some embodiments, at least two of first portion, the second portion, and the side portion are contiguous. In some embodiments, the first portion comprises a first wall, the second portion comprises a second wall, and the side portion comprises a side wall.

In some embodiments the method comprises providing an in-growth patch on at least one of the first portion configured to engage the first bone (e.g. a femur, a tibia, or a patella, in the case of the knee device), the second portion configured to engage the second bone, the side portion, and the appendage. The in-growth patch may be configured to encourage and/or promote tissue in-growth, such as bone in-growth, for non-limiting example. The patch may be as large as the portion itself (whether the first portion the second portion, the side portion, or the appendage) or may be smaller than the portion (such as in the shape of a strip or other shaped patch). The in-growth patch may comprise a surface irregularity or roughness. The in-growth patch may be Velcro-like. In some embodiments the implant comprises an in-growth patch on the first portion and/or the second portion, from (and in some embodiments including) a first appendage to a second appendage. In some embodiments, wherein the appendages loosen from attachment from the bone (by design and/or from wear and/or over time), the in-growth patch aids in securing the implant to the bone. In some embodiments, the in-growth patch comprises beads and/or bead-like elements attached to the implant. Such an in-growth patch may be configured to simulate trabecular bone space of a normally cancellous latticework. In some embodiments, the beads are sintered beads of various sizes. In some embodiments, the beads are sintered beads about 400 microns in size. With respect to bead size, the term "about" can mean ranges of 1%, 5%, 10%, 25%, or 50%. In some embodiments, the first bone and/or the second bone is roughened to acquire a bleeding bone to facilitate in-growth. In some embodiments, about 0.5 mm of cortical tissue is removed to facilitate in-growth.

In some embodiments, the method comprises coupling a second appendage of the balloon to the first bone of the joint. In some embodiments, the method comprises coupling a second appendage of the balloon to at least one second bone of the joint. In some embodiments, the method comprises coupling a second appendage of at least one of the first portion, the second portion, and the side portion to at least one of the first bone and at least one second bone of the joint. In some embodiments, coupling at least one of the first appendage and the second appendage provides ligamentary-like support to the first bone and at least one second bone of the joint. In some embodiments, coupling at least one of the first appendage and the second appendage provides ligamentary-like support to the joint. In some embodiments, the first appendage and the second appendage are configured to provide tendon-like support to the first bone and the at least one second bone of the joint. In some embodiments, the first appendage and the second appendage are configured to provide tendon-like support to the joint.

In some embodiments, the method comprises providing an inflation port in communication with the interior of the balloon for inflation of the interior of the balloon with the first inflation medium. In some embodiments, the method comprises using an inflation port of the implant that is in communication with the interior of the balloon to inflate the interior of the balloon with the first inflation medium. In some embodiments, the method comprises puncturing the balloon to inflate the interior of the balloon with the first inflation medium. In some embodiments, the method comprises providing a balloon having self-sealing capability. In some embodiments, the method comprises providing a balloon having self-sealing capability upon inflation of the interior of the balloon with the first inflation medium. In some embodiments, the method comprises providing a balloon comprising a seal capable of closing the interior of the balloon.

In some embodiments, the method comprises providing a balloon having an interior comprising a plurality of inflatable chambers. In some embodiments, the interior comprises a plurality of individually inflatable chambers. In some embodiments, the method comprises inflating a first chamber of the plurality of inflatable chambers with a first inflation medium. In some embodiments, the first chamber and the inflation medium is selected based on the particular needs of the patient. For non-limiting example, if the patient has bone loss due to an injury, the chamber may be selected at the location of the missing bone, and may be filled with a rigid inflation medium (or one that becomes rigid once in the chamber) in order to replace the missing and/or damaged bone. Alternatively, or in addition, a chamber may be chosen to restore alignment of the joint, and inflated with an appropriate inflation medium to impart both alignment and cushion to the joint. In some embodiments, the method comprises inflating a second chamber of the plurality of individually inflatable chambers with a second inflation medium.

In some embodiments, the balloon is a composite structure. In some embodiments, the balloon comprises layers of porous and/or non-porous materials, or otherwise contains treatment or cell regeneration agents. In some embodiments, a first layer of the balloon is a thin, but strong layer of a thermoplastic, such as a thermoplastic polyurethane, for non-limiting example, which has microporosity sufficient to allow passage or egress of treatment or cell regeneration agents from a second layer. The second layer may be a central layer (which lies between the first layer and a third layer or a fourth layer or more layers). The first layer may comprise a bone engaging surface in some embodiments. The degree of microporosity to enable egress of treatment or cell regeneration agents from the second layer is found in polymer layers such as Chronoflex (e.g., ChronoFlexAR®, ChronoFlex AL®, ChronoFlec C®) or BIONATE (e.g., BIONATE I, BIONATE II, BIONATE 55D, BIONATE 65D, BIONATE 75D, BIONATE 80A, BIONATE 90A, BIONATE 55 or BIONATE 80). The bone engaging surface of the implant may be coated and/or impregnated with a latticework of polymer that is surface sprayed or layered on the bone engaging surface of the implant to promote cartilage tissue regeneration. This bone engaging surface coating may contain living chondrocytes (for example, as is provided in the Carticel procedure by the Genzyme company), and/or may contain stem cells with directed gene mutations to enhance adherence of the coating to the implant. The bone engaging surface may comprise peaks and troughs. The living cells may be provided in troughs while the surface peaks may be used for at least one of: space validation, traction, and cell protection.

In some embodiments, the first inflation medium imparts rigidity in the implant. In some embodiments, the first inflation medium imparts cushion in the implant. In some embodiments, the inflation medium chosen for the first inflation medium, and/or the particular choice of chamber (in embodiments having multiple chambers) filled with such first inflation medium aligns the joint. In some embodiments, the inflation medium chosen for the first inflation medium, and/or the particular choice of chamber (in embodiments having multiple chambers) filled with such first inflation medium aligns the bones of the joint. In some embodiments, the inflation medium chosen for the first inflation medium, and/or the particular choice of chamber (in embodiments having multiple chambers) filled with such first inflation medium changes the bone alignment. In some embodiments, the inflation medium chosen for the first inflation medium, and/or the particular choice of chamber (in embodiments having multiple chambers) filled with such first inflation medium improves joint alignment. In some embodiments, the inflation medium chosen for the first inflation medium, and/or the particular choice of chamber (in embodiments having multiple chambers) filled with such first inflation medium restores, at least in part, joint alignment. In some embodiments, individual chambers of the interior are selectively inflated with a first inflation medium and/or a second inflation medium. In some embodiments, individual chambers of the interior are selectively inflated with a first inflation medium and/or a second inflation medium in order to reconstruct the joint and/or in order to reconstruct bones of the joint.

Over time, in-growth of repair tissue aids in fixation and stability externally to the implant, while the soft cushioning implant interior may absorb forces across the joint surfaces and permit proper motion. The turgor or wall tension of the implant as well as the inside distension of the implant per se can be adjusted by adding or removing the inflation substance to the implant's interior space.

Accordingly, the present invention provides a new approach to arthroplasty that involves a resilient implant deployed between bones of the knee joint. In some instances, a joint is comprised of the interface between (a) a first bone and a first cartilage; and (b) a second bone and a second cartilage, wherein the first cartilage is separated from the second cartilage by a space (e.g., joint space) and the cushion expands to fit the joint space. In some instances, where the first cartilage and/or second cartilage is damaged or absent, the cushion expands to fit the joint space between the first bone and second cartilage or the first bone and second bone. In certain joint spaces such as the knee, the cushion expands to fit the spaces of the "knee joint" or "knee joints". For example, the cushion may expand to fit the spaces of the femoral tibial involved on standing or walking on a level plane, and the cushion may expand to fit the spaces of the patella femoral bones of the knee more involved on stair ascent and descent. For example, pressures behind the knee cap or patella when lying are zero, when standing are 0.7 times body weight, and when going up and down the patella femoral pressures are 3-4 times body weight. Thus, in some instances, the implants accommodate some or all of the normal body functional pressures and complex space movements, as described above, and can also be used in other joints such as the elbow, ankle, or hip. When in the hip joint, the normal flexion up to 120 degrees, extension of 20 degrees, abduction of 50 degrees, internal and external rotation of 45 degrees may produce variable axial, shear, and cyclic loads which the implant by design may accommodate and endure as up to 6 times body weight, consistent with a tire on a car that allows for cyclic loads different when driving straight or turning corners. The implant embodying features of the present invention provides more physiologic motion and shock absorption within the joint and has combined characteristics of anatomic design symmetry, balanced rigidity with sufficient attachment connections to adjacent normal structures, and durability that meet the needs of joint reconstruction.

The opposing internal surfaces of the first and second walls of the invention may either move together in synchrony or in opposite directions from one another (e.g. the superior wall moving medially in the hip and the inferior wall moving laterally). Optionally, the implant may be fixed to a concave surface of the joint (e.g., the acetabular hip cup) or to a convex surface of the joint (e.g. the dorsal femoral head surface), to both, or to neither (e.g., having an interference fit within the joint with an expanding balloon or cushion that fills the existing space). The implant may be inserted arthroscopically like a deflated balloon and then inflated through a cannula into the ankle or hip (or other joint structure) to act as a cushion or renewed interface for painless and stable limb motion. When feasible, joint capsular and adjacent ligament tissue as well as bone may be left in place to preserve the natural body, unless interfering with reconstructed limb function.

The application of steam in addition to removing damaged debris, can smooth out and reform the joint surface. The high temperature of the steam tends to weld cracks or fissures which can be present in the cartilage surface of a damaged joint. Smoothing of joint surface cartilage with steam welds or seals existing cracks or flaps in the cartilage, especially superficially as the lamina splendors, which melt together to provide a white shiny gliding joint surface. In cases where bone is exposed, the steam can be used to stabilize the periphery of the defect in the joint surface via capsulorrhaphy or joint tightening. Open mechanical and chemical debridement may also be employed to prepare the surfaces for the implant.

Once the implant is secured to the femur by means of the skirt or tabs or using other couplers, an impregnated transfer medium or cell template may be used, as described by Histogenics and Tygenix chondrocytes delivery systems wherein the position of concentrated cells is mechanically placed about the implant at areas of greatest cartilage damage to promote regrowth, or as in Carticel wherein watery cells are implanted beneath a periosteal membrane (a wall of the implant serving as the membrane), prior to completion of the inflation or expansion of the implant. A syringe or gauged device with measured screw-home pressure is used to inflate the implant.

Once the joint is ready to receive the implant, the deflated implant is advanced through the diaphragm of a delivery cannula (such as the Acufex from Smith & Nephew) or through the open incision site into the joint. It can be inflated by the attached cannula using a common syringe, inserting several cc's of filler material. Inserted contents and locations of cell placements depend on areas of need and joint size. In some embodiments of the methods several cc's of filler material and a viscolubricant in the interior of the implant allows distension, cushioning, and gliding movements. Cell regeneration agents are placed in the areas of greatest need.

Methods of living cell (e.g., stem cell, differentiated cell, pluripotent cell, post-mitotic cell) or chondrocyte placement depend on the lesions and specific implant construct. Direct infusion into the joint with completion of implant inflation may press the cells into the hyaline surface, whereupon they attach within the first 24 hours. As a result, the patient may be forced to remain sedentary and the joint where the implant is deployed, non-weight bearing for the first day after surgery. Deeper osteochondral defects can be treated by 'hyper-perfusion of cells' via either 3-D cell transfer templates, or microneedle injection as used in treatment of diabetic patients for blood sugar testing and insulin/transdermal drug delivery. In cases of osteochondritis dissecans or localized both cartilage and bone lose, bone graft may be packed into the base of the defect followed by addition of a cell/tissue application. The cannula attached to the implant may be sealed and detached, or left in place for periodic aspiration of noxious enzymes as for the Cox-1, Cox-2, and 5-Lox systems, followed by reinsertion of activated substances including viscolubricants, or even more cells (e.g., stem cells, differentiated cells, pluripotent cells, post-mitotic cells).

Implants embodying features of the invention may be designed for permanent or temporary deployment within a joint structure. Moreover, the implant may be formed of suitable bioabsorbable materials so that the implant may be absorbed within a particular predetermined time frame. Suitable bioabsorbable materials include polylactic acid, polyglycolic acid, polycaprolactone, copolymers, blends and variants thereof. One present method of forming the implant is to apply numerous layers of polymer such as ChronoFlex (e.g., ChronoFlexAR®, ChronoFlex AL®, ChronoFlec C®), ChronoPrene™, ChronoSil®, ChronoThane P™ ChronoThane T™, HydroMed™, HydroThane™, or PolyBlend™ in a solvent and evaporating the solvent after applying each layer.

The coupling aspects (couplers) including but not limited to skirting or fixation tabs of the present implant prevent joint migration during use.

In some embodiments, the implant is adapted to restore natural joint function. In some embodiments, the implant is adapted to preserve viable joint tissue. In some embodiments, the implant is adapted to be placed with minimal surgery as compared to joint replacement therapy currently marketed. In some embodiments, the implant is adapted to permit weight bearing post surgery within at least one of: about 1 week, within about 1 day, within about 2 days, within about 3 days, within about 4 days, within about 5 days, within about 6 days, within about 10 days, within about 2 weeks, within about 3 weeks, within about 4 weeks, within about 5 weeks, within about 6 weeks. In some embodiments, the implant is adapted to permit weight bearing post surgery after about 1 day wherein full weight bearing is allowed in about 6 weeks. As used herein with respect to weight bearing timing, the term "about" can be a range of 1 day, 2 days, or 3 days, in some embodiments. In some embodiments, the implant is adapted to allow for faster recovery and resumption of normal activities as compared to joint replacement therapy currently marketed.

In some embodiments, the balloon (or a portion thereof) is adapted to conform to the patient's anatomy. In some embodiments, the implant (or a portion thereof) is adapted to conform to the patient's anatomy. In some embodiments, the inflation medium is adapted to absorb a force (or forces) exerted on the joint. In some embodiments, the inflation medium is adapted to absorb a force (or forces) exerted on the bones of the joint. In some embodiments, the inflation medium is adapted to absorb a force (or forces) exerted on at least one bone of the joint. In some embodiments, the balloon is adapted to absorb shocks exerted on at least one of a bone, multiple bones, a ligament of the joint, ligaments of the joint, a tendon of the joint, tendons of the joint, and the joint in general. In some embodiments, the implant is adapted to restore natural cartilage cushion with cells (e.g., stem cells, differentiated cells, pluripotent cells, post-mitotic cells). In some embodiments, the implant is adapted to restore natural cartilage cushion with stem cells.

In some embodiments, the balloon (or a portion thereof) is adapted to renew joint space. In some embodiments, the balloon (or a portion thereof) is adapted to reduce pain as compared to the pain felt prior to the implantation of the implant. In some embodiments, the balloon (or a portion thereof) is adapted to restore joint function. In some embodiments, the implant (or a portion thereof) is adapted to renew joint space. In some embodiments, the implant (or a portion thereof) is adapted to reduce pain as compared to the pain felt prior to the implantation of the implant. In some embodiments, the implant (or a portion thereof) is adapted to restore joint function.

In some embodiments, the implant is adapted to reverse arthritis in the joint. In some embodiments, the implant is adapted to prevent, reduce, or ameliorate arthritis in the joint. In some embodiments, the implant is adapted to reduce pain associated with arthritis in the joint.

In some embodiments, the balloon (or a portion thereof) is adapted to be placed into a debrided limb joint arthroscopically. In some embodiments, the balloon is adapted to pad cartilage defects. In some embodiments, the balloon is inflated to cushion the joint. In some embodiments the implant is adapted to deliver stem cells to at least one of the joint and a bone of the joint. In some embodiments the implant is adapted to deliver living chondrocytes to at least one of the joint and a bone of the joint. In some embodiments, the implant is adapted to deliver cells to at least one of the joint and a bone of the joint. In some embodiments, the cells are at least one of stem cells, differentiated cells, pluripotent cells, and post-mitotic cells. In some embodiments, the implant is adapted to provide a new articular surface for the joint. In some embodiments, the implant is adapted to act as a spacer in the joint. In some embodiments, the implant is adapted to space the bones of the joint apart for proper joint articulation. In some embodiments, the implant is adapted to space the bones of the joint apart for reduced bone-on-bone rubbing.

In some embodiments, the implant is configured to at least one of: pad cartilage, cushion the joint, deliver a pharmacologic substance, remove noxious enzymes, debride upon implantation, debride the joint following implantation, deliver a therapeutic substance, deliver a biologic substance, and deliver living stem cells. In some embodiments, the implant is configured to deliver a chemotherapeutic agent to a bone or other surrounding tissues. In some embodiments, the implant is configured to deliver an anti-infectious medication to a bone or other surrounding tissues. In some embodiments, the implant is configured to deliver at least one of an antibiotic, antifungals, and analgesics agent.

In some embodiments, the implant is configured to be selectively inflated to realign limbs.

Provided herein is a method comprising: implanting a knee implant as described herein into a subject, wherein the implant reverses arthritis in the subject. Provided herein is a method comprising: implanting a knee implant as described herein into a subject, wherein the implant prevents, reduces, or ameliorates arthritis in the subject. Provided herein is a method comprising: implanting a knee implant as described herein into a subject, wherein the implant reduces pain associated with arthritis in the subject.

Provided herein is a method comprising: implanting a knee implant as described herein into a knee joint of a subject and treating a component of the knee joint of the subject with at least one of an allograph tissue, an autograph tissue, and an xenograph tissue. In some embodiments, the tissue comprises a cell. In some embodiments, the tissue comprises a plurality of cells. In some embodiments, the cell is a stem cell, differentiated cell, pluripotent cell, or post-mitotic cell. In some embodiments, the implanting step is at least one of: prior to the treating step, simultaneous with the treating step, and following the treating step.

Provided herein is a method comprising: implanting a knee implant as described herein into a subject, wherein the implant is configured to at least one of: restore joint function and control arthopathies. In some embodiments, the implanting spares existing anatomy.

Provided herein is a method comprising: debriding a femur condyle of a knee joint of a subject, and implanting a knee implant as described herein into the knee joint of the subject, whereby the implant is configured to anneal to the cartilage of the subject. In some embodiments, the debriding is achieved by steam application.

Provided herein is a method comprising implanting a knee implant as described herein into a joint previously treated with a joint replacement. In some embodiments, the method comprises removing the joint replacement prior to implanting the knee implant. In some embodiments, the method comprises clearing infectious matter from the joint and/or surrounding tissues. In some embodiments, the method comprises implanting a second implant of any implant described herein following removing the implant previously implanted in the joint. In some embodiments, the method comprises replacing the joint of the subject following removing the implant previously implanted in the joint. In some embodiments, the method comprises debriding the bone of the joint, and implanting an implant of any implant described herein. In some embodiments, the method comprises repeating the debriding and implanting steps.

The surgical techniques may be individualized to fit patient need. The implants may be combined with or comprise autologous or allograph tissues such as fascia lata. Surgeons may implant fascia lata above unreconstructable rotator cuff with consequent symptom relief Polymers can interface with any human tissue and/or with metals or polyethylenes or polyurethanes. Living tissues that can be combined with implants provided herein for repair or reconstruction may be from the same patient (autograph), and cadaver or other member of the same species (allograph) or from another species (xenograph.) Virtually any combination of polymer interpositioning is feasible with the implant concepts provided herein, as anatomy varies among patients in need, and clinical conditions differ with each person. Therefore, although the general or most common construct is expected to cover just one singular and the primary surface of a joint with an implant, any combination of surfaces can be involved allowing versatile custom applications of this implant and method of surgery.

Additionally, whereas implants may be available in specified sizes, the material membrane elastic deformation and resilience may allow for calculated malleability toward goodness of fit. In other iterations the fit of implant over the affected joint surface can be customized as paring preoperative findings of MRI or CT or PET imaging pathophysiology with intraoperative reconstructive need. Ultimately best fit implants may serve patient restorative requirement with least morbidity.

The implants may be implanted typically during an outpatient surgery, wherein the joint is first arthroscopically debrided and cartilage prepared, similar to the methods used in a Carticel procedure. Cartilage or osteochondral size defects and alignment problems are studied, and measurements taken. Considerations to materials stretch are acknowledged as polyurethanes gain 50% pliability with 100 hours exposure to serum, and 30% additional malleability by heating to 37 degrees C. Thus, implant presentation in the OR may aim for best fit and accommodate patient need.

Intraoperative hyaline cartilage biopsy acquiring e.g. 400 mg of normal hyaline articular tissue from the intercondylar notch (as would be wasted with notchplasty) or from the joint periphery (outside articulating regions) may allow for chondrocytes autologous acquisition. Currently such specimens may be sent to Genzyme Corp. for 2-4 weeks cloning of cells whereupon 2-3 bottles containing e.g. 1 cc of cells, 93% viability, 12 million cells per bottle, are delivered on an exact day to the operating room for placement in the Carticel cartilage regenerative procedure securing the liquid cells beneath a harvested periosteal membrane. In implant surgery contemplated in certain embodiments, the polymer may substitute for the periosteum thus reducing surgical morbidity markedly and changing an otherwise major open procedure into an arthroscopically facilitated outpatient treatment option through a small arthrotomy.

With outpatient surgeries the intraoperative biopsy may be given to the technician in the operating room in early surgery, for insertion into the stem cells generation machine. In 30-40 minutes living autologous chondrocytes may be 'spun down' and separated, then returning the living cells to the primary surgeon. By this time, the implant has been pulled up over the prepared defects and sufficient fixation sites have been locked into place so that the implant is secure in its general location over the distal femoral surface, for example. An unattached portion of the implant is lifted, the newly procured cells inserted potentially on a soft matrix to hold cells inside the prepared defect, and the implantation is completed sealing the living cells for the purpose of articular surface regeneration. After 24 hours the cells are fixed as the aggregate to the surface of the defect into which they were introduced. This begins a one year period of regrowth of the new joint surface. Concurrently the arthritis osteochondral defect so treated is padded by the implant, and the joint cushioned is mechanically restored. Said cushioning is by nano and/or macro inflation and/or by use of polymers with variable compliance. Immediate fixation and the opportunity for a regenerated joint are thus accomplished in the operating room. This may use either the implant matched to size by preoperative planning via X-rays considering the magnification factors, by using one of the other scanning methods available, or by custom generation ultimately of implant partial or entire coverage options in the same surgery.

Once the implant is secured circumferentially and solidly in place with multiple fixation sites verified as patent, one or two forms of orthobiologic activity proceed. Specifically, if chondrocytes were implanted (autologous or potentially allograph) they may mature and in the course of a year the durometry may come to resemble normal hyaline articular cartilage. The other biologic activity promoted during implantation surgery is the bone in-growth onto the tab undersurface and/or periphery. This fixation at the secondary level in proposed to decrease the probability of loosening of the prosthetic implant, one of the two most common causes of implant failure. With the normal 10,000 steps people take per day during normal gait, or 2-4 million cycles per annum, the compressive and shear forces, and cyclic loads can cause micromotion between the implant and natural underlying tissue. This may lead to implant shift, dislocation, and/or hardware backing out if not appropriately secured to the bones. In the implant technique the immediate fixation is achieved through multiple robust circumferential fixation of implant tabs to bone. Each screw and washer secures the mechanically adequate implant tab to bone at over 300 pounds force to failure. Since, depending on the embodiment, there may be ten (10) tab sites intended the sum of 3000 pounds. In some embodiments, fixation comprises bone in-growth. In some embodiments, the fixation comprises bone in-growth as described in Vasanji A, In vivo bone growth assessment in preclinical studies and clinical trials, Bonezone, 2012, p. 12-17, herein incorporated by reference in its entirety.

The methods of surgery may have certain constants and other variables mandated by materials and fixation management versus altering anatomies and joint forces. In each joint a standardized implant method of surgery may be recommended with variations to be determined by the responsible surgeon.

While particular forms of the invention have been illustrated and described herein, it will be apparent that various modifications and improvements can be made to the invention. One alternative implant construction involves the use of an upper portion of the implant having a net-like construction and filled with balls or ball bearing like elements that are larger than the openings in the netting. The balls or ball bearing like elements provide motion to the implant. The netting and ball bearing like elements may include regeneration agents as previously discussed, and the bearing construction may be directed toward favorable implant movement balanced with content disbursement.

The invention is intended primarily for human use but may be extended to mammalian use. Examples of mammals include, but are not limited to, cats, dogs, sheep, horses, pigs, goats, cows, mice, and rats. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be utilized in another embodiment. Moreover, individual features of one embodiment may be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C § 112(6) unless the following claims expressly use the terms "means for" or "step for" followed by a particular function without reference to a specific structure or a specific action. All patents and all patent applications referred to above are hereby incorporated by reference in their entirety.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for restoring a joint comprising: providing an implant configured for deployment between a femur and a tibia of a knee joint, the implant comprising
    a first portion that is configured to directly engage a medial condyle and a lateral condyle of the femur of the knee joint,
    a second portion that is configured to directly engage the tibia of the knee joint,
    a first appendage configured to couple the first portion to a first condyle of the femur of the knee joint, the first appendage having a pre-set curvature configured to simulate curvature of the first condyle and at least one pre-formed hole for securing the first appendage to the first condyle,
    a second appendage configured to couple the first portion to a second condyle of the femur of the knee joint, the second appendage having a pre-set curvature configured to simulate curvature of the second condyle and at least one pre-formed hole for securing the second appendage to the second condyle,
    a slot between the first appendage and the second appendage, and
    a cushioning element within the implant configured to provide a cushion for the femur and tibia, the cushioning element comprising a thermoplastic polyurethane polycarbonate, and
    wherein the first portion, the second portion, the first appendage, and the second appendage together comprise a single contiguous polymer sheet, such that the implant results in the restoration of a joint;
    deploying the implant between the femur and the tibia of a knee joint; and
    securing the implant with at least one coupler wherein the at least one coupler is accommodated by at least one pre-formed hole.

2. The method of claim 1, wherein the restoration comprises an implant provided with orthobiologics.

3. The method of claim 1, wherein the restoration comprises an implant provided with a pharmacologic agent.

4. The method of claim 3, wherein the pharmacologic agent comprises growth factors, antibodies, biomolecules, biologics, chemical compounds, analgesics, antibiotics, anticancer agents, viscolubricants or combinations thereof.

5. The method of claim 3, wherein the pharmacologic agent comprises Gleevac®, Doxorubicine®, NSAIDs, Synvisc®, Hyalgan®, Supartz® or lidocaine.

6. The method of claim 1, wherein the restoration comprises tissue regeneration, reduction of arthritis, amelioration of arthritis or the reduction of pain.

7. The method of claim 6, wherein the tissue regeneration comprises an implant provided with joint tissue regeneration agents.

8. The method of claim 7, wherein the tissue regeneration agents comprise stem cells, living chondrocytes, genes or combinations thereof.

9. A method for restoring a joint comprising: providing an implant configured for deployment between a femur and a patella of a knee joint, the implant comprising
   a first portion that is configured to directly engage at a trochlear groove of the femur of the knee joint,
   a second portion that is configured to directly engage the patella of the knee joint,
   a first appendage configured to couple the first portion to a first condyle of the femur of the knee joint, the first appendage having a pre-set curvature configured to simulate curvature of the first condyle and at least one pre-formed hole for securing the first appendage to the first condyle,
   a second appendage configured to couple the first portion to a second condyle of the femur of the knee joint, the second appendage having a pre-set curvature configured to simulate curvature of the second condyle and at least one pre-formed hole for securing the second appendage to the second condyle, and
      a slot between the first appendage and the second appendage, and
   a cushioning element within the implant configured to cushion the femur and patella, the cushioning element comprising a thermoplastic polyurethane polycarbonate, and wherein the first portion, the second portion, the first appendage, and the second appendage together comprise a single contiguous polymer sheet, such that the implant results in the restoration of a joint; and
      deploying the implant between the femur and the patella of a knee joint; and
      securing the implant with at least one coupler wherein the at least one coupler is accommodated by at least one pre-formed hole.

10. The method of claim 9, wherein the restoration comprises an implant provided with orthobiologics.

11. The method of claim 9, wherein the restoration comprises an implant provided with a pharmacologic agent.

12. The method of claim 9, wherein the restoration comprises tissue regeneration, reduction of arthritis, amelioration of arthritis or the reduction of pain.

13. The method of claim 12, wherein the tissue regeneration comprises an implant provided with joint tissue regeneration agents.

14. The method of claim 13, wherein the tissue regeneration agents comprise stem cells, living chondrocytes, genes or combinations thereof.

15. A method for restoring a joint comprising: providing an implant configured for deployment between a tibia and a patella of a knee joint, the implant comprising
   a first portion that is configured to directly engage at the tibia of the knee joint,
   a second portion that is configured to directly engage the patella of the knee joint,
   a first appendage configured to couple the first portion to a first condyle of the tibia of the knee joint, the first appendage having a pre-set curvature configured to simulate curvature of the first condyle and at least one pre-formed hole for securing the first appendage to the second condyle,
   a second appendage configured to couple the first portion to a second condyle of the tibia of the knee joint, the second appendage having a pre-set curvature configured to simulate curvature of the second condyle and at least one pre-formed hole for securing the first appendage to the second condyle, and
      a slot between the first appendage and the second appendage, and
   a cushioning element within the implant configured to cushion the tibia and patella, the cushioning element comprising a mesh sheet or inflatable chamber, and
   wherein the first portion, the second portion, the first appendage, and the second appendage together comprise a single contiguous polymer sheet, such that the implant results in the restoration of a joint; and
      deploying the implant between the tibia and the patella of a knee joint; and
      securing the implant with at least one coupler wherein the at least one coupler is accommodated by at least one pre-formed hole.

16. The method of claim 15, wherein the restoration comprises an implant provided with orthobiologics.

17. The method of claim 15, wherein the restoration comprises an implant provided with a pharmacologic agent.

18. The method of claim 15, wherein the restoration comprises tissue regeneration, reduction of arthritis, amelioration of arthritis or the reduction of pain.

19. The method of claim 18, wherein the tissue regeneration comprises an implant provided with joint tissue regeneration agents.

20. The method of claim 19, wherein the tissue regeneration agents comprise stem cells, living chondrocytes, genes or combinations thereof.

* * * * *